US012270889B2

(12) United States Patent
Stoev et al.

(10) Patent No.: US 12,270,889 B2
(45) Date of Patent: Apr. 8, 2025

(54) CONTINUOUS WAVE ULTRASOUND OR ACOUSTIC NON-DESTRUCTIVE TESTING

(71) Applicant: ATOMIC ENERGY OF CANADA LIMITED/ÉNERGIE ATOMIQUE DU CANADA LIMITÉE, Chalk River (CA)

(72) Inventors: Krassimir Stoev, Ottawa (CA); Stuart Craig, Deep River (CA); Teguewinde Sawadogo, Petawawa (CA)

(73) Assignee: ATOMIC ENERGY OF CANADA LIMITED/ÉNERGIE ATOMIQUE DU CANADA LIMITÉE, Chalk River (CA)

( * ) Notice: Subject to any disclaimer, the term of this patent is extended or adjusted under 35 U.S.C. 154(b) by 589 days.

(21) Appl. No.: 17/186,921

(22) Filed: Feb. 26, 2021

(65) Prior Publication Data

US 2021/0293947 A1    Sep. 23, 2021

Related U.S. Application Data

(63) Continuation-in-part of application No. PCT/CA2019/051207, filed on Aug. 29, 2019.

(Continued)

(51) Int. Cl.
*G01S 13/32* (2006.01)
*G01N 29/04* (2006.01)
(Continued)

(52) U.S. Cl.
CPC .......... *G01S 13/32* (2013.01); *G01N 29/041* (2013.01); *G01N 29/348* (2013.01);
(Continued)

(58) Field of Classification Search
CPC .......... G01S 13/32; G01S 7/534; G01S 15/34; G01S 15/88; G01N 29/041; G01N 29/348;
(Continued)

(56) References Cited

U.S. PATENT DOCUMENTS 2,769,158 A    10/1956   Schultz
3,332,278 A    7/1967    Wood
(Continued)

FOREIGN PATENT DOCUMENTS

CA    1074002    3/1980
CA    2314305    1/2002
(Continued)

OTHER PUBLICATIONS

Extended European Search Report for EP19854893.5, mailed Mar. 23, 3022.
(Continued)

*Primary Examiner* — Daniel Pihulic
(74) *Attorney, Agent, or Firm* — Joseph C. Zucchero; Carolyn S. Elmore; Elmore Patent Law Group, P.C

(57) ABSTRACT

A method of determining a distance to a discontinuity within an object may include the steps of: a) generating a continuous, frequency modulated input signal having a predetermined frequency range and a frequency ramping speed using a signal generator and splitting the input signal into at least a test signal and a reference signal; b) generating an input sound wave based on the test signal and continuously introducing the input sound wave into the object using a transmitter and simultaneously receiving a reflected sound wave reflected by a discontinuity within the object and generating a corresponding return signal using a receiver; c) determining a frequency difference value based on a comparison of the reference signal and the return signal using a (Continued)

controller; and d) automatically determining a distance from the transmitter to the discontinuity within the object based on at least the frequency difference value and the frequency ramping speed.

9 Claims, 59 Drawing Sheets

Related U.S. Application Data

(60) Provisional application No. 62/724,951, filed on Aug. 30, 2018.

(51) Int. Cl.
 *G01N 29/34* (2006.01)
 *G01N 33/2045* (2019.01)
(52) U.S. Cl.
 CPC . *G01N 33/2045* (2019.01); *G01N 2291/0234* (2013.01); *G01N 2291/0423* (2013.01); *G01N 2291/101* (2013.01)
(58) Field of Classification Search
 CPC ....... G01N 33/2045; G01N 2291/0234; G01N 2291/0423; G01N 2291/101; G01N 2291/0289; G01N 29/069; G01N 2291/044; G01N 29/345; G01N 29/4436; G01N 29/4454; G01N 29/46
 See application file for complete search history.

(56) References Cited

U.S. PATENT DOCUMENTS

| | | | |
|---|---|---|---|
| 3,466,652 | A | 9/1969 | Heyser |
| 3,572,099 | A | 3/1971 | Wieczorek |
| 3,918,295 | A | 11/1975 | Herbertz |
| 4,428,235 | A | 1/1984 | Sugiyama |
| 4,884,246 | A | 11/1989 | Heyser |
| 5,062,296 | A | 11/1991 | Migliori |
| 5,228,004 | A | 7/1993 | Kawasaki |
| 5,303,590 | A | 4/1994 | Modderman |
| 5,351,543 | A | 10/1994 | Migliori |
| 5,591,913 | A | 1/1997 | Tucker |
| 5,631,423 | A | 5/1997 | Rhodes |
| 5,734,588 | A | 3/1998 | Rose et al. |
| 6,148,672 | A | 11/2000 | Cawley et al. |
| 6,261,232 | B1 | 7/2001 | Yokosawa |
| 6,343,510 | B1 | 2/2002 | Neeson |
| 7,114,390 | B2 | 10/2006 | Lizon |
| 7,502,278 | B1 | 3/2009 | Imbornone |
| 7,798,000 | B1 | 9/2010 | Murray et al. |
| 8,170,809 | B2 | 5/2012 | Van et al. |
| 8,323,200 | B2 | 12/2012 | Kunita |
| 2005/0203391 | A1 | 9/2005 | Phelps |
| 2006/0058656 | A1 | 3/2006 | Kristoffersen |
| 2006/0241464 | A1 | 10/2006 | Ohtake |
| 2008/0027323 | A1 | 1/2008 | Freiburger |
| 2008/0269612 | A1 | 10/2008 | Kunita |
| 2009/0097012 | A1 | 4/2009 | Gardner |
| 2009/0099453 | A1 | 4/2009 | Kristoffersen |
| 2009/0150094 | A1 | 6/2009 | Van et al. |
| 2009/0312636 | A1 | 12/2009 | Kunita |
| 2010/0113934 | A1 | 5/2010 | Oguzman |
| 2010/0280387 | A1 | 11/2010 | Schmid |
| 2013/0023767 | A1 | 1/2013 | Mammone |
| 2014/0221842 | A1 | 8/2014 | Castelino |
| 2015/0053009 | A1 | 2/2015 | Yan et al. |
| 2015/0185318 | A1 | 7/2015 | Huang |
| 2016/0139264 | A1 | 5/2016 | Larocque |
| 2016/0202347 | A1 | 7/2016 | Malinovskiy et al. |
| 2018/0113205 | A1 | 4/2018 | Sikdar et al. |
| 2021/0293947 | A1* | 9/2021 | Stoev ................. G01N 33/2045 |

FOREIGN PATENT DOCUMENTS

| | | | | |
|---|---|---|---|---|
| CA | 2780455 | | 6/2011 | |
| CA | 3110818 | A1 * | 3/2020 | ........... G01N 29/041 |
| CN | 102078204 | | 6/2011 | |
| CN | 102865839 | | 1/2013 | |
| CN | 102879309 | | 1/2013 | |
| CN | 103235039 | | 8/2013 | |
| CN | 103297783 | | 9/2013 | |
| CN | 203970415 | | 12/2014 | |
| DE | 3331531 | | 3/1985 | |
| DE | 4116584 | | 11/1992 | |
| DE | 19527779 | | 2/1996 | |
| EP | 1693004 | | 8/2006 | |
| EP | 0932837 | B1 | 7/2012 | |
| EP | 3318869 | A1 * | 5/2018 | |
| EP | 3844530 | A4 * | 4/2022 | ........... G01N 29/041 |
| FR | 2621203 | | 3/1989 | |
| GB | 1313535 | | 4/1973 | |
| GB | 2121174 | | 12/1983 | |
| IT | 1241801 | | 2/1994 | |
| JP | 2000107186 | | 4/2000 | |
| JP | 2013039261 | | 2/2013 | |
| KR | 20120055859 | | 6/2012 | |
| KR | 20120059738 | | 6/2012 | |
| KR | 20130085249 | | 7/2013 | |
| RU | 2107907 | | 3/1998 | |
| RU | 2193208 | | 11/2002 | |
| RU | 2004124905 | | 1/2006 | |
| WO | 9502819 | | 1/1995 | |
| WO | 9612951 | A1 | 5/1996 | |
| WO | 9622527 | A1 | 7/1996 | |
| WO | 9725852 | | 7/1997 | |
| WO | 2012006189 | | 1/2012 | |
| WO | 2018043788 | A1 | 3/2018 | |
| WO | WO-2020041891 | A1 * | 3/2020 | ........... G01N 29/041 |

OTHER PUBLICATIONS

International Preliminary Report on Patentability for PCT/CA2019/051207, completed Nov. 16, 2020 and Response to Written Opinion filed Jun. 29, 2020.
Battaglini, et al., "A low cost ultrasonic rangefinder based on frequency modulated continuous wave", 20th IMEKO TC4 International Symposium and 18th International Workshop on ADC Modelling and Testing, Research on Electric and Electronic Measurement for the Economic Upturn, Benevento, Italy, Sep. 15-17, 2014.
Kunita, M. et al., "Range Measurement in Ultrasound FMCW System", Electronics and Communications in Japan, Part 3, 90(1), 2007, 9-19.
Mokhles, et al., "The use of ultrasonic guided waves for extended pipeline qualification prediction", SINCE2013, Singapore International NDT Conference & Exhibition 2013, Jul. 19-20, 2013.
R. C. Heyser, "Acoustical measurements by time delay spectrometry", Journal of the Audio Engineering Society, v. 15, n. 4, p. 370-382 (1967).
P. M. Gammell, "Single transducer swept frequency ultrasonic reflection measurements", Ultrasonics, v.17, p. 183-185 (1979).
G. Ludwig, K. Brendel, "Calibration of hydrophones based on reciprocity and time delay spectrometry", IEEE Transactions on Ultrasonics, Ferroelectrics and Frequency Control, v. 35, n. 2, p. 168-174 (1988).
B. Scheffold, O. Weis, "Frequency modulation-continuous wave method to generate and detect sound beams at 35 GHz", Applied Physics Letters , v. 65, n. 6, p. 688-690 (1994).
P. M. Gammell and G. R. Harris, "Time delay spectrometry for hydrophone calibrations below 1 MHz", J. Acoust. Soc. Am., v. 106, n. 5, p. L41-L46 (1999).
C. Koch, "Amplitude and phase calibration of hydrophones by heterodyne and time-gated time-delay spectrometry", IEEE Transactions on Ultrasonics, Ferroelectrics and Frequency Control, v. 50, n. 3, p. 344-348 (2003).
P. M. Gammell, S. Maruvada, and G. R. Harris, "A Simplified Ultrasonic Time-Delay Spectrometry (TDS) System Employing

(56) References Cited

OTHER PUBLICATIONS

Digital Processing to Minimize Hardware Requirements", AIP Conference Proceedings, v. 820, p. 692-699 (2005).
P. M. Gammell, S. Maruvada, G. R. Harris, "An ultrasonic time-delay spectrometry system employing digital processing", IEEE Transactions on Ultrasonics, Ferroelectrics and Frequency Control, v. 54 , n. 5, p. 1036-1044 (2007).
P. C. Pedersen, A. Grebe, "Application of time delay spectrometry for rough surface characterization", Ultrasonics, v. 39, n. 2, p. 101-108 (2001).
J. Wilhjelm, C. Pedersen, "Target velocity estimation with FM and PW echo ranging Doppler system—part I: Signal Analysis", IEEE Transactions on Ultrasonics, Ferroelectrics and Frequency Control, v. 40, n. 4, p. 366 (1993).
J. Wilhjelm, C. Pedersen, "Coherent FM Doppler system", Proceedings of IEEE Ultrasonics Symposium, v. 2, p. 903-906 (1989).
K. McCarty, J. P. Woodcock, "Frequency modulated ultrasonic Doppler flowmeter", Medical and Biological Engineering, v. 13, n. 1, p. 59 (1975).
M. Kunita, M. Sudo, S. Inoue, M. Akahane, "A new method for blood velocity measurements using ultrasound FMCW signals", IEEE Transactions on Ultrasonics, Ferroelectrics and Frequency Control, v. 57, n. 5, p. 1064-1076 (2010).
R. C. Heyser, D. H. Le Croissette, "A new ultrasonic imaging system using time delay spectrometry", Ultrasound in Medicine & Biology, v. 1, n. 2, p. 119-131 (1974).
R. C. Heyser, J. D. Hestenes, J. A. Rooney, P. M. Gammell, D. H. Le Croissette, "Medical ultrasound imager based on time delay spectrometry", Ultrasonics, v. 27, n. 1, p. 31-38 (1989).
J. A. Rooney, R. C. Heyset, J. D. Hestenes, and D. H. LeCroissette, "Application of time delay spectrometry to medical imaging", J. Acoust. Soc. Am., v. 73, n. S1, p. S9-S9 (1983).
E. Blomme, D. Bulcaen, F. Declercq, "Recent observations with air-coupled NDE in the frequency range of 650 KHz to 1.2 MHz ", Ultrasonics, v. 40, n. 1, p. 153-157 (2002).
T. H. Gan, D. A. Hutchins, and R. J. Green, "A swept frequency multiplication technique for air-coupled ultrasonic NDE", IEEE Transactions on Ultrasonics, Ferroelectrics and Frequency Control, v. 51, n. 10, p. 1271-1279 (2004).
C. R. Cole, "Properties of swept FM waveforms in medical ultrasound imaging" Proceedings of IEEE Ultrasonics Symposium, v.2, p. 1243-1248 (1991).
T. H. Gan, D. A. Hutchins, and R. J. Green, "Swept Frequency Multiplication (SFM) Techniques for Improved Air-Coupled Ultrasonic NDE", AIP Conf. Proc., v. 657, p. 620-627 (2002).
M.J.S. Lowe et al. "Long Range Guided Wave Inspection Usage—Current Commerical Capabilities and Research Directions" (2006).
P. Cawley et al. "Practical Long Range Guided Wave Testing: Applications to Pipes and Rail" Materials Evaluation, Jan. 2003.
J. Li et al. "Excitation and propagation of non-axisymmetric guided waves in a hollow cylinder" J. Acoust. Soc. Am. 109 457-464 (2001).
A. Demma et al. "The effects of Bends on the Propagation of Guided Waves in Pipes" ASME vol. 127, August 328-335 (2005).
D. Zhang et al. "A Magnetostrictive Guided-Wave Nondestructive Testing Method With Multifrequency Excitation Pulse Signal" IEEE Transactions on Instrumentation and Measurement, vol. 63 No. Dec. 12, 2014.
M. Lowe "Plate Waves For The NDT of Diffusion Bonded Titanium" Imperial College of Science, Technology and Medicine, Dec. 1992.
P.C. Pedersen "Application of Time-Delay Spectrometry for Calibration of Ultrasonic Transducers" IEEE Transations on Ultrasonics, Ferroelectrics, and Frequency Control, vol. 35, No. 2 Mar. 1988.
W. Eickhoff et al. "Optical Frequency Domain Reflectometry in Single-Mode Fiber" Appl. Phys. Lett. 39, 693-695 (1981).
B. Golubovic et al. "Opticial Frequency-Domain Reflectometry Using Rapid Wavelength Turning of a Cr4+:forsterite Laser" Optics Letter, vol. 22, No. 22, 1704-1706 Nov. 15, 1997.
B. Soller et al. "High resolution optical frequency domain reflectometry for characterization of components and assemblies" Optics Express, vol. 13, No. 2, 666-674, Jan. 24, 2005.
Y Park et al. "Optical Frequency Domain Reflectometry Based on Real-Time Fourier Transformation" Optics Express, vol. 15, No. 8 4597-4616, Apr. 16, 2007.
Innerspec Document Rev. T-SA-A19.

\* cited by examiner

CONTINUOUS WAVE ULTRASOUND OR ACOUSTIC NON-DESTRUCTIVE TESTING

CROSS REFERENCE TO RELATED APPLICATIONS

This application is a Continuation-in-Part of International Application No. PCT/CA2019/051207, filed Aug. 29, 2019, published in English, which claims the benefit under U.S.C. § 119(e) of provisional application Ser. No. 62/724,951 entitled Method and Apparatus for Continuous Wave Ultrasound or Acoustic Non-Destructive Testing and filed Aug. 30, 2018, the contents of which are hereby incorporated by reference.

FIELD

The present subject matter relates generally to a method and apparatus for non-destructive testing, and specifically to a method of using mechanical waves such as ultrasound or acoustic waves for such testing.

INTRODUCTION

U.S. Pat. No. 6,343,510 discloses an ultrasonic testing method and apparatus which includes synthesizing impulse response images using specially constructed waveforms. The apparatus includes a waveform generator, transducers for transmitting and receiving the ultrasonic signals and a digital signal processor or computer for efficiently processing the captured signal data to form the desired impulse response signals.

Canadian Patent Publication No. 1,074,002 discloses a method and apparatus for determining the flow state of a flowable substance by transmitting ultrasonic or ultrasound waves of constant frequency to a spatial region of the substance, receiving ultrasonic waves back-scattered by the substance, converting the back-scattered ultrasonic waves into a primary signal which is amplitude and phase-modulated in accordance with the backscattering and demodulating the primary signal in order to obtain a modulation signal. This modulation signal can be divided into a spectrum of signal components of different frequency and possessing pseudo periods which are defined as the time intervals between successive momentary values of the modulation signal, such momentary values corresponding to one another. The time duration corresponding to a predetermined number of pseudo periods is compared with a predetermined time duration.

US Patent Publication No. 2013/023767 discloses a system and method for performing ultrasound testing including generating a set of continuous tone signals for injection into an object.

A corresponding set of reflected tone signals in the frequency domain may be received. The set of reflected tone signals may be converted from the frequency domain to the time domain to create a set of time domain signals. At least one region of interest may be identified from the set of time domain signals. A window may be defined around the identified region of interest in the set of time domain signals. The windowed time domain signals may be converted from the time domain to the frequency domain to create a set of windowed frequency domain signals. At least one characteristic parameter may be calculated from the set of windowed frequency domain signals. Information may be output based on the calculation of at least one characteristic parameter.

SUMMARY

In accordance with one broad aspect of the teachings disclosed herein, a method of determining a distance to a discontinuity within an object may include the steps of:
a) generating a continuous, frequency-modulated input signal having a predetermined frequency range and a frequency ramping speed using a signal generator and splitting the input signal into at least a test signal and a reference signal;
b) generating an input sound wave based on the test signal and continuously introducing the input sound wave into the object using a transmitter and simultaneously receiving a reflected sound wave reflected by a discontinuity within the object and generating a corresponding return signal using a receiver;
c) determining a frequency difference value based on a comparison of the reference signal and the return signal using a controller; and
d) automatically determining a distance from the transmitter to the discontinuity within the object based on at least the frequency difference value and the frequency ramping speed using the controller.

Determining the frequency difference value may include multiplying the reference signal with the return signal using a signal multiplier.

Determining frequency difference value may include multiplying the reference signal with the return signal using the signal multiplier to provide a multiplied output signal (MOS), applying a fast Fourier transform (FFT) to the MOS to provide an FFT spectrum and identifying the frequency difference value as a peak on the FFT spectrum.

The method may include filtering the MOS with a filter to filter out at least some frequencies from the MOS to provide a filtered output signal before calculating the FFT.

The filter may include a low pass filter that is configured to filter out frequencies above the minimum frequency generated in step a).

The method may include passing the filtered output signal through a DAQ downstream from the signal multiplier prior to digitizing the filtered output signal prior to calculating the FFT.

The method may include receiving a second reflected sound wave reflected by a second discontinuity within the object and generating a corresponding second return signal using the receiver, and:
step 1c) may include determining a first frequency difference value based on a comparison of the reference signal and the first return signal using the controller, and determining a second frequency difference value based on a comparison of the reference signal and the second return signal using the controller; and
step 1d) may include automatically determining the distance from the transmitter to the first discontinuity within the object based on at least the first frequency difference value and the frequency ramping speed using the controller and automatically determining a distance from the transmitter to the second discontinuity within the object based on at least the second frequency difference value and the frequency ramping speed using the controller.

The method may include identifying the first frequency difference value as a first peak on the FFT spectrum and identifying the second frequency difference value as a second peak on the FFT spectrum.

Determining the distance from the transmitter to the first discontinuity within the object and determining the distance from the transmitter to the second discontinuity within the object may occur simultaneously.

The distance may be determined based on the frequency difference, the frequency ramping speed and a speed of sound within the object.

The distance may be calculated using the frequency difference, the frequency ramping speed and a speed of sound within the object.

The distance may be calculated using the function $$d_i = \frac{v \cdot f_R}{2 \cdot \Delta f},$$

where $d_i$ Is the distance (mm), v is speed of sound within the object (mm/s), $f_R$ is the frequency difference (MHZ) and $\Delta f$ is the frequency ramping speed (MHz/s).

The frequency ramping speed may be between about 0.01 and 1000 MHz/sec, and may be about 20 MHz/sec.

Steps c) and d) may be performed simultaneously with step b).

The input signal may include a sinusoidal signal and the frequency ramp of the input signal is substantially linear.

The method may include amplifying the test signal before it reaches the transmitter using a first amplifier, and amplifying the return signal after it leaves the receiver and before it reaches the signal multiplier.

The frequency range may be between about 1 MHz to about 20 MHz and may be between about 1 MHz and about 4 MHz.

The input signal may have a maximum frequency that is less than about 20 MHz.

The input signal may have an amplitude of less than 20V, and preferably about 2V.

The frequency range of the input signal may be substantially equal to a usable frequency range of the transmitter.

The sound wave may include an ultrasound signal, having a frequency of at least 20 KHz.

The sound wave may include an acoustic signal having a frequency that is equal to or less than 20 KHz.

The discontinuity may include at least one of a flaw within the object, an edge or surface of the object, and an interface between the object and an adjacent object.

The input sound wave may include a bulk body wave.

The input sound wave may include a guided wave and is generated using a guided wave transducer.

The input sound wave may include a Rayleigh-Lamb wave.

In accordance with another broad aspect of the teachings described herein, a system for determining a distance to a discontinuity within an object may include:
a) a signal generator configured to generate a continuous, frequency-modulated input signal having a predetermined frequency range and a frequency ramping speed;
b) a splitter communicably linked to the signal generator and configured to split the input signal into at least a test signal and a reference signal;
c) a transmitter communicably linked to the splitter to receive the test signal and configured to generate an input sound wave based on the test signal and transmit the input sound wave into an object;
d) a receiver configured to receive a reflected sound wave from the object and generate a corresponding return signal, the reflected sound wave being reflected by a discontinuity within the object;
e) a controller communicably linked to the splitter to receive the reference signal and to the receiver to receive the return signal, the controller configured to determine a frequency difference value based on a comparison of the reference signal and the return signal and to determine a distance from the transmitter to the discontinuity within the object based on at least the frequency difference value and the frequency ramping speed The controller may include: a signal multiplier configured to multiply the return signal with the reference signal to provide a multiplied output signal, a low pass filter configured to filter out at least some of the frequencies in the multiplied output signal and provide a filtered output signal; and a data acquisition apparatus configured to digitize the filtered output signal and provide a digitized output signal.

The controller may be configured to determine the frequency difference value by applying a fast Fourier transform to the digitized output signal to provide a FFT spectrum and identifying the frequency difference value as a peak on the FFT spectrum.

The controller may be configured to determine the distance based on the frequency difference, the frequency ramping speed and a speed of sound within the object.

The controller may be configured to calculate the distance using the function $$d_i = \frac{v \cdot f_R}{2 \cdot \Delta f},$$

where $d_i$ is the distance (mm), v is speed of sound within the object (mm/s), $f_R$ is the frequency difference (MHz) and $\Delta f$ is the frequency ramping speed (MHz/s).

The receiver may be configured to receive a reflected sound wave while the transmitter is transmitting the input sound wave into an object.

The transmitter may include a guided wave transducer that is operable to generate a guided wave.

The frequency ramping speed may be between about 0.01 and 1000 MHz/sec, and optionally may be about 20 MHz/sec.

The input signal may include a sinusoidal signal and the frequency ramp of the input signal is substantially linear.

The system may include a first amplifier configured to amplify the test signal before it reaches the transmitter and a second amplifier configured to amplify the return signal after it leaves the receiver and before it reaches the signal multiplier.

The system may include a user output device communicably linked to the controller and configured to display the distance to a user.

In accordance with another broad aspect of the teachings described herein, a method of determining a distance to a discontinuity within an object using a guided wave may include the steps of:
a) generating a continuous, frequency-modulated input signal having a predetermined frequency range and a frequency ramping speed using a signal generator and splitting the input signal into at least a test signal and a reference signal;
b) generating an input guided wave based on the test signal using a guided wave transducer, wherein the frequency range is limited to frequencies for which a phase velocity of the input guided wave is substantially constant;

c) continuously introducing the input guided wave into the object using the guided wave transducer, and simultaneously receiving a reflected sound wave reflected by a discontinuity within the object and generating a corresponding return signal using a receiver;

d) determining a frequency difference value based on a comparison of the reference signal and the return signal using a controller; and e) automatically determining a distance from the transmitter to the discontinuity within the object based on at least the frequency difference value and the frequency ramping speed using the controller.

The guided wave transducer may include an angle beam transducer and the input guided wave is generated using an angle beam method.

The angle beam transducer may generate the input guided wave at an angle of incidence relative to the object and wherein the angle of incidence may remain constant during steps b) and c).

The input guided wave may include a Rayleigh-Lamb wave.

Step e) may include: multiplying the return signal with the reference signal using a signal multiplier to provide a multiplied output signal, filtering the multiplied output signal using a low-pass filter to filter out at least some of the frequencies in the multiplied output signal and provide a filtered output signal; digitizing the filtered output signal using a data acquisition apparatus to provide a digitized output signal; and determining the frequency difference value by applying a fast Fourier transform to the digitized output signal to provide a FFT spectrum, and identifying the frequency difference value as a peak on the FFT spectrum.

Step e) may include determining the distance based on the frequency difference, the frequency ramping speed and a speed of sound within the object.

The distance may be determined using the function $$d_i = \frac{v \cdot f_R}{2 \cdot \Delta f},$$

where $d_i$ is the distance (mm), v is speed of sound within the object (mm/s), $f_R$ is the frequency difference (MHZ) and $\Delta f$ is the frequency ramping speed (MHz/s).

The frequency ramping speed may be between about 0.01 and 1000 MHz/sec and may be about 20 MHz/sec.

DRAWINGS

The drawings included herewith are for illustrating various examples of articles, methods, and apparatuses of the teaching of the present specification and are not intended to limit the scope of what is taught in any way.

Figure 60:
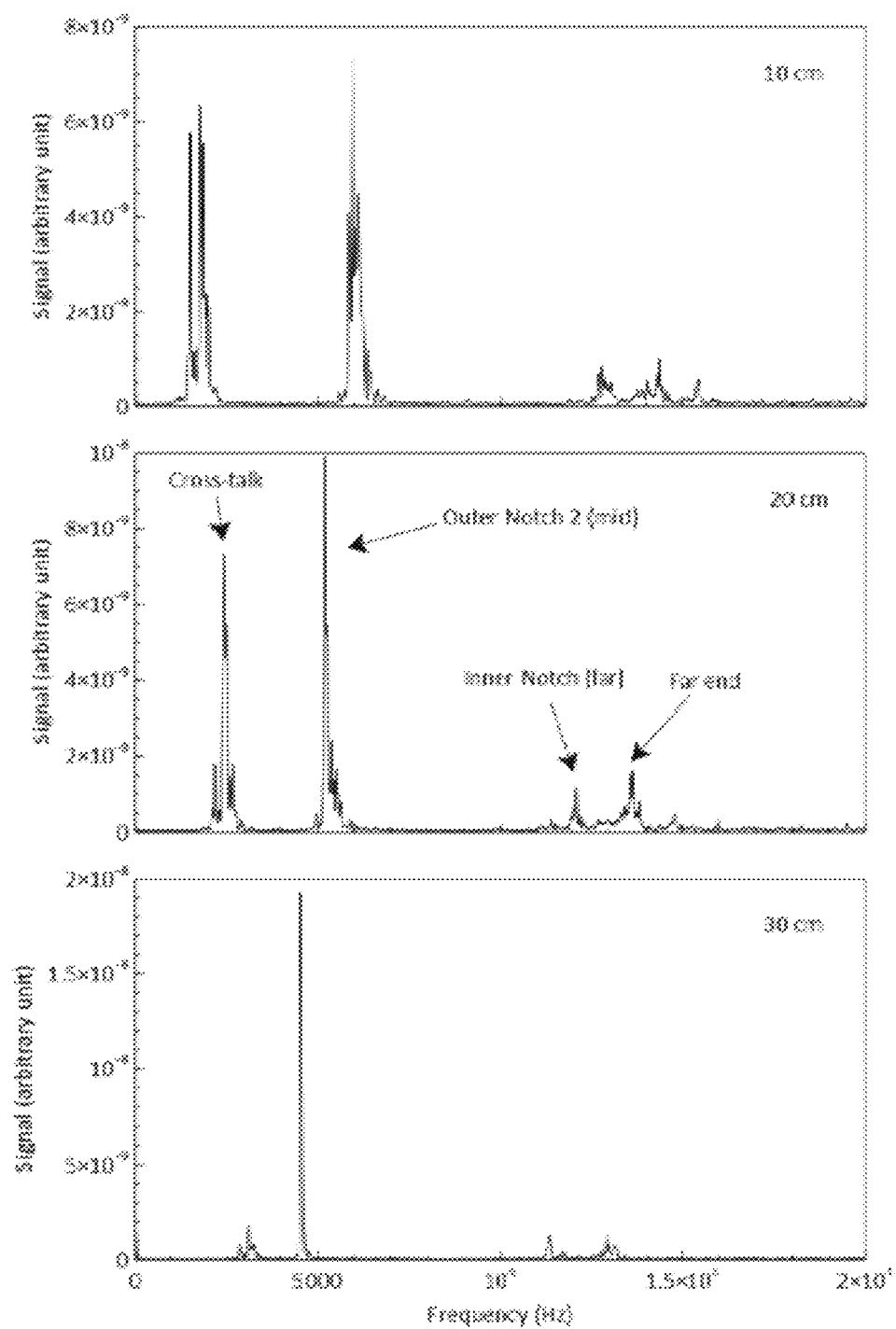
Figure 62:
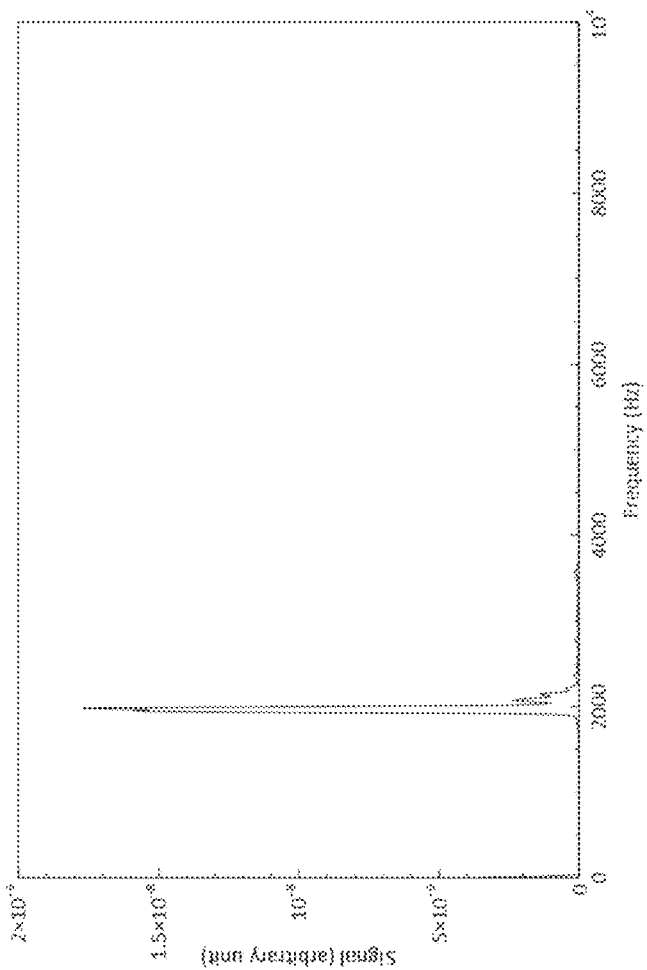
Figure 61:
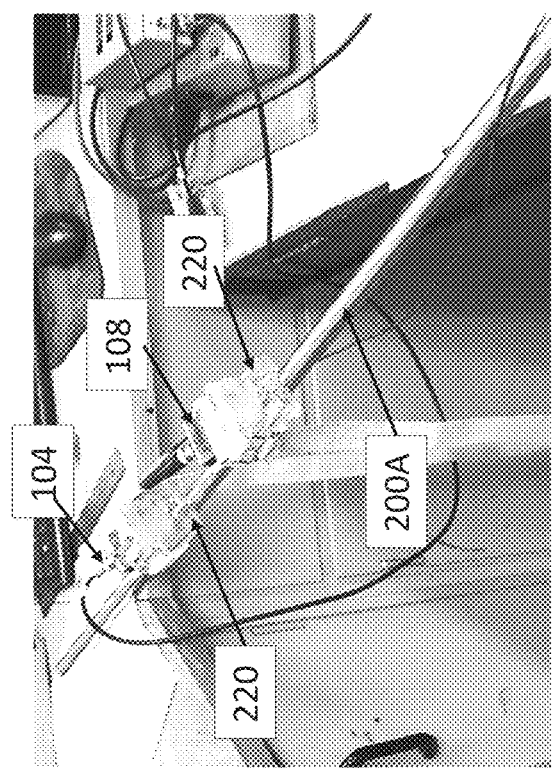
Figures 63, 64:
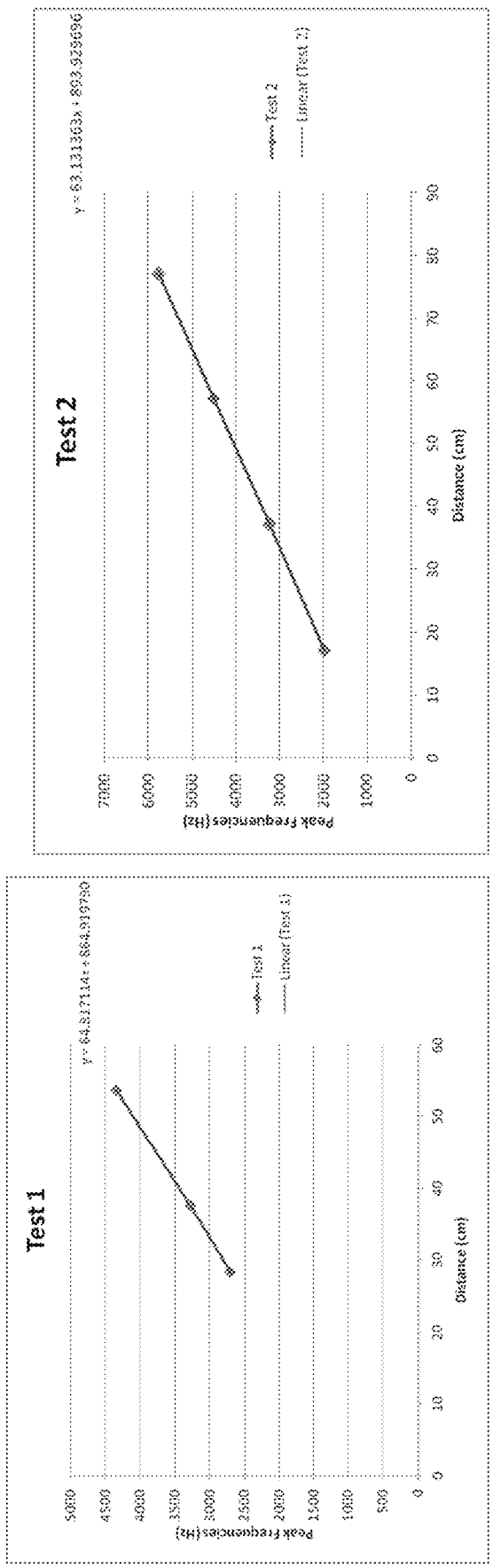

FIG. 60 includes plots of the frequency domain signal for a notch detection test;

FIG. 61 is a photo of a setup for the continuous guided wave testing on an Inconel tube;

FIG. 62 is a plot showing typical continuous wave signal in the frequency domain for wave speed measurement test on the Inconel tube;

FIG. 63 is a plot showing peak frequencies versus transducer separation distance for the wave speed measurement on the Inconel tube for Test 1;

FIG. 64 is a plot showing peak frequencies versus transducer separation distance for the wave speed measurement on the Inconel tube for Test 2.

Figure 65:
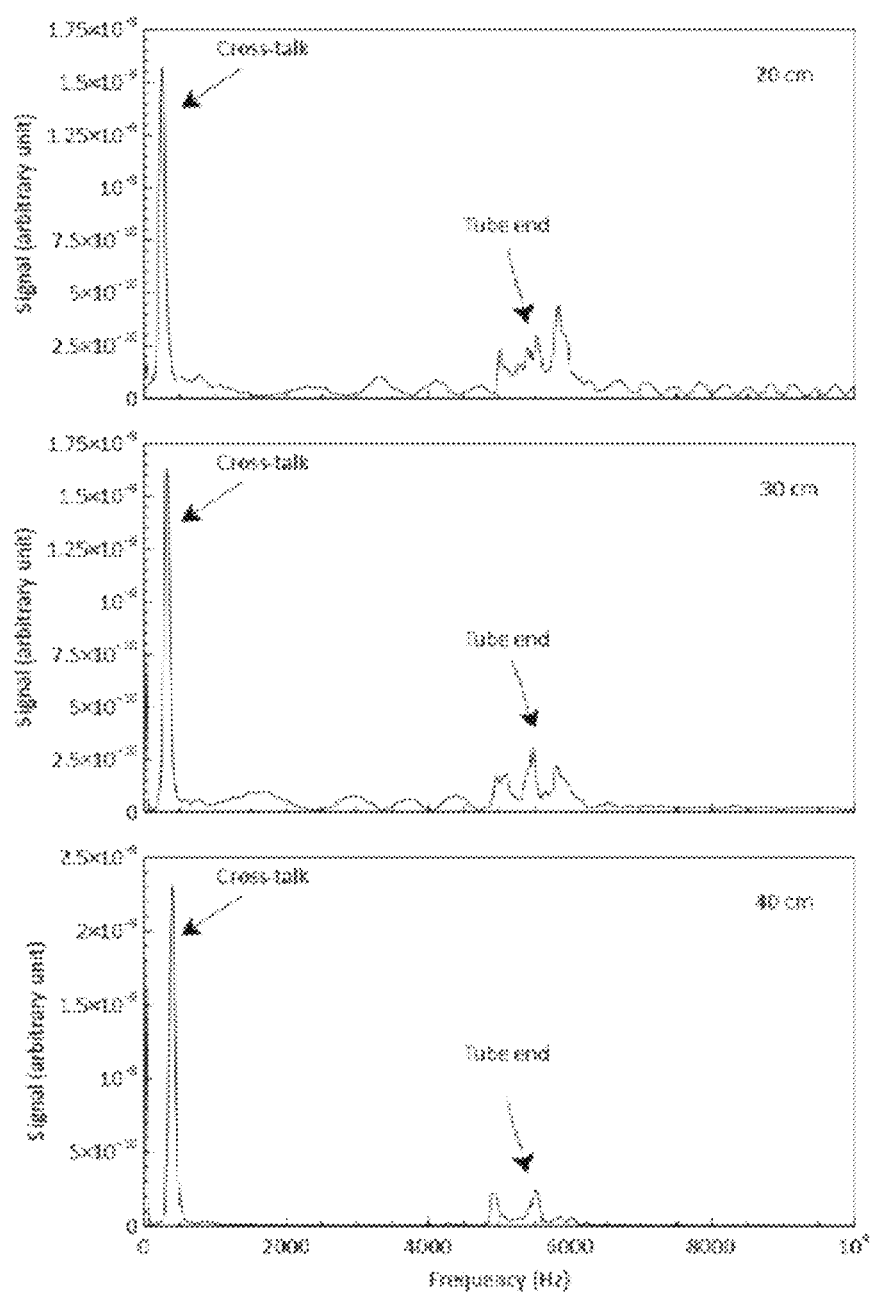
Figure 66:
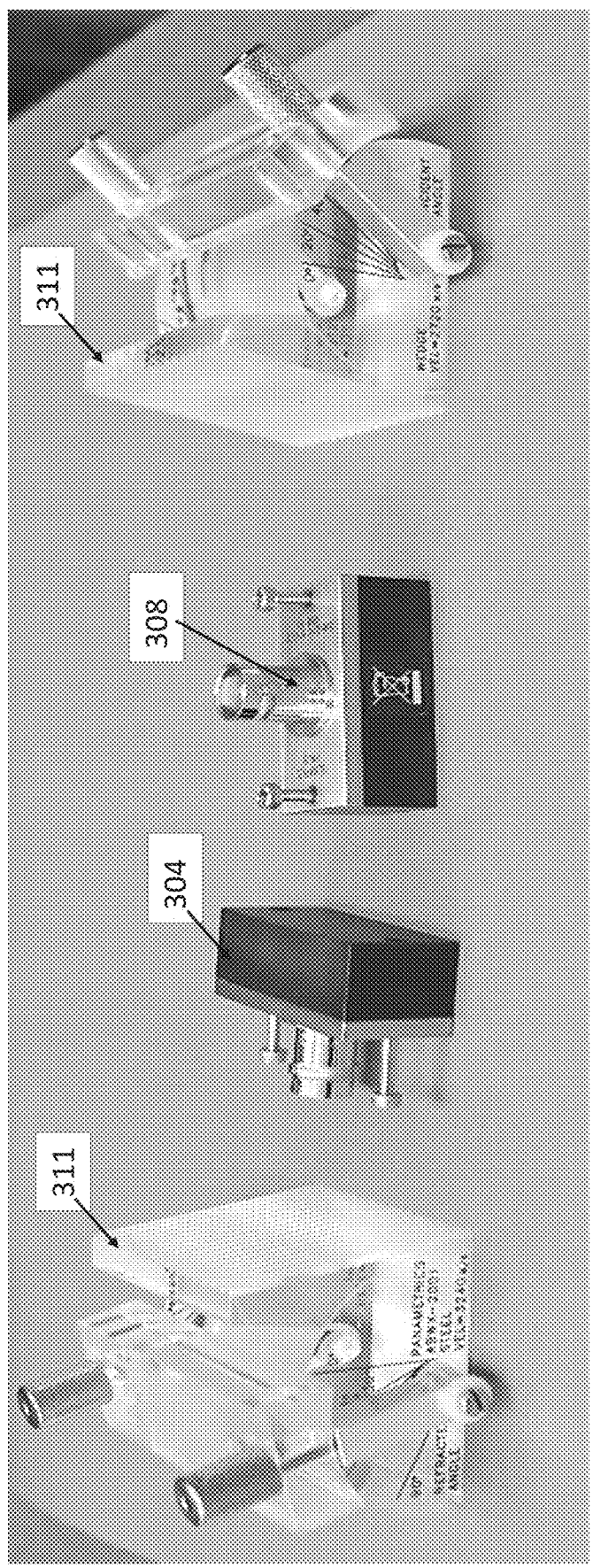
Figure 67:
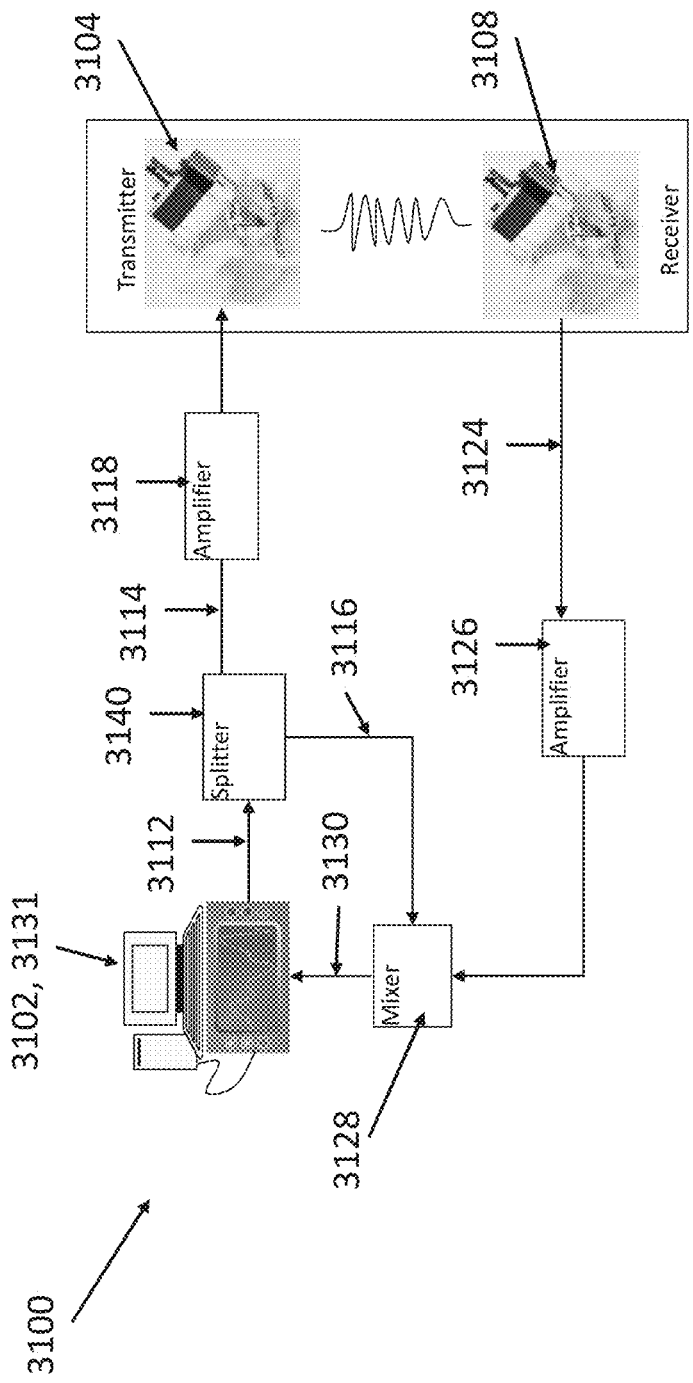
Figure 68:
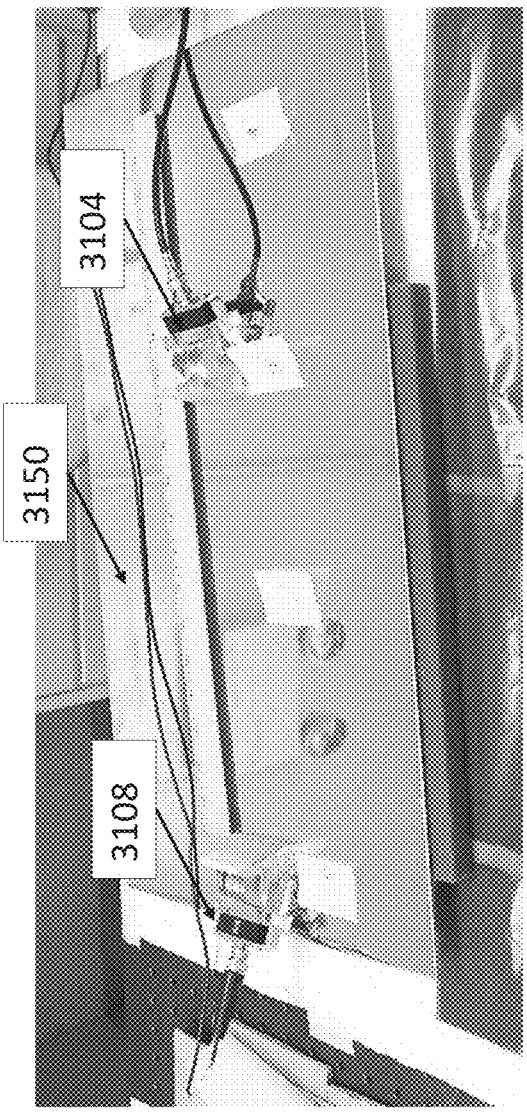
Figure 69:
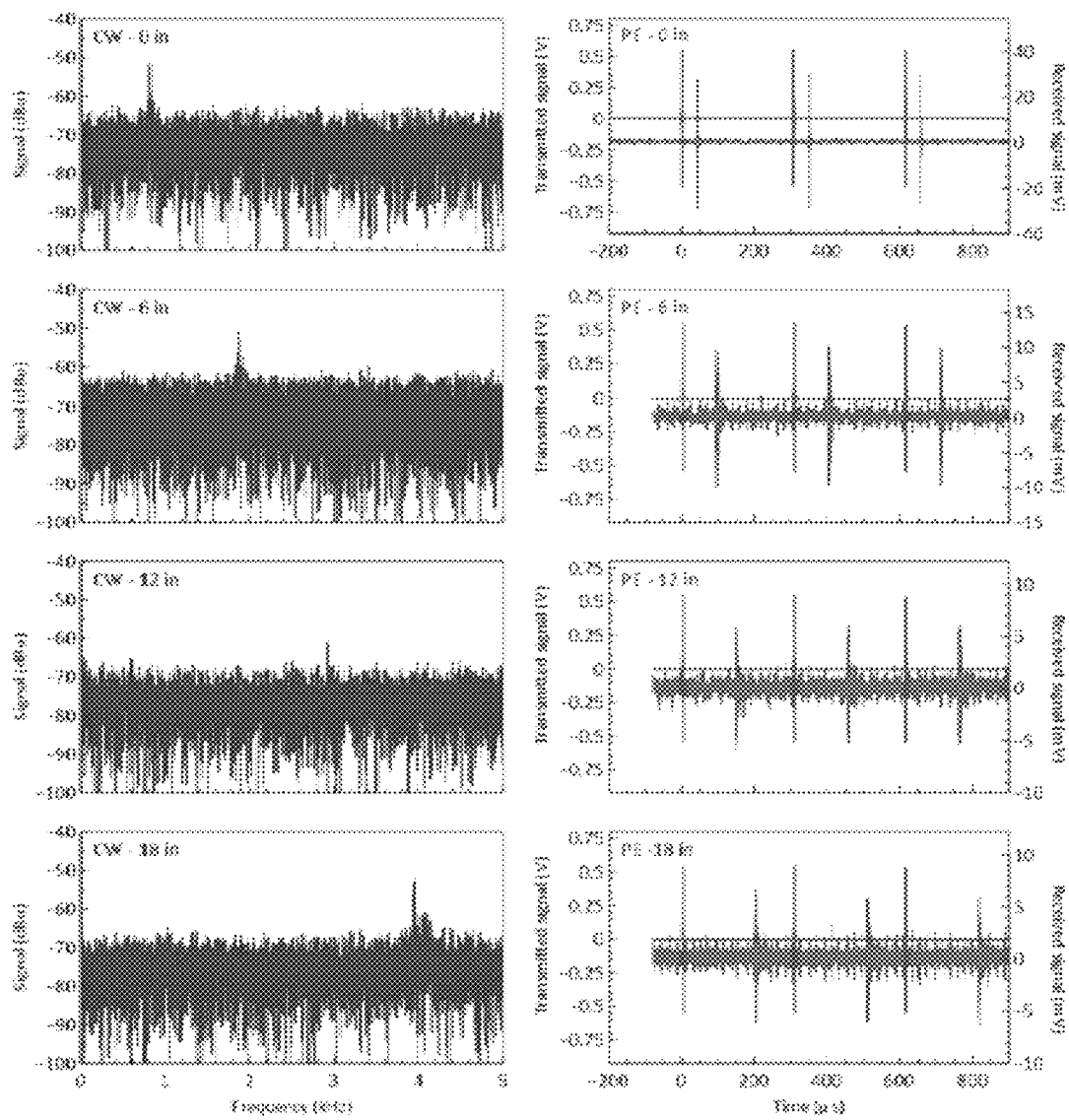
Figure 71:
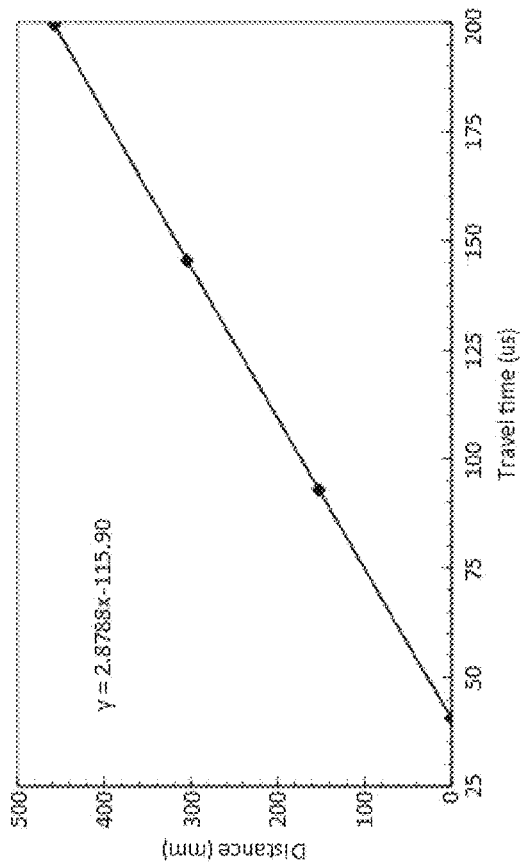
Figure 70:
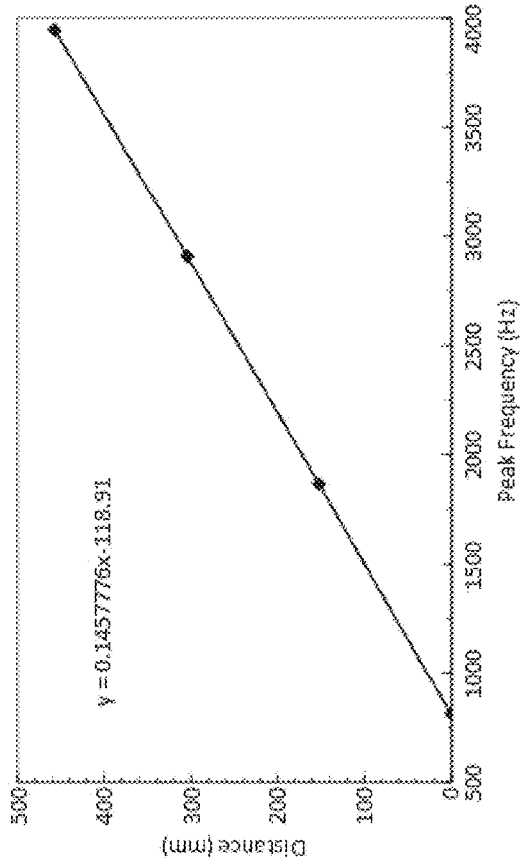
Figure 73:
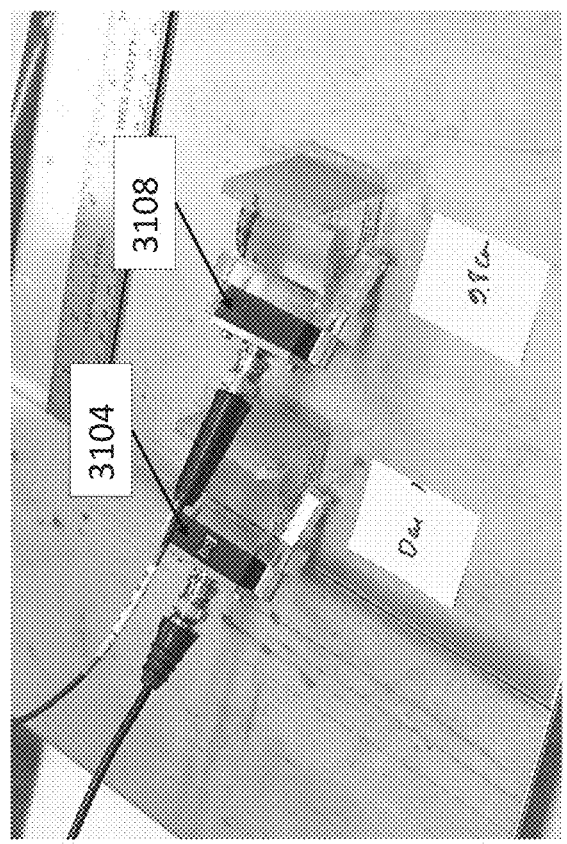
Figure 72:
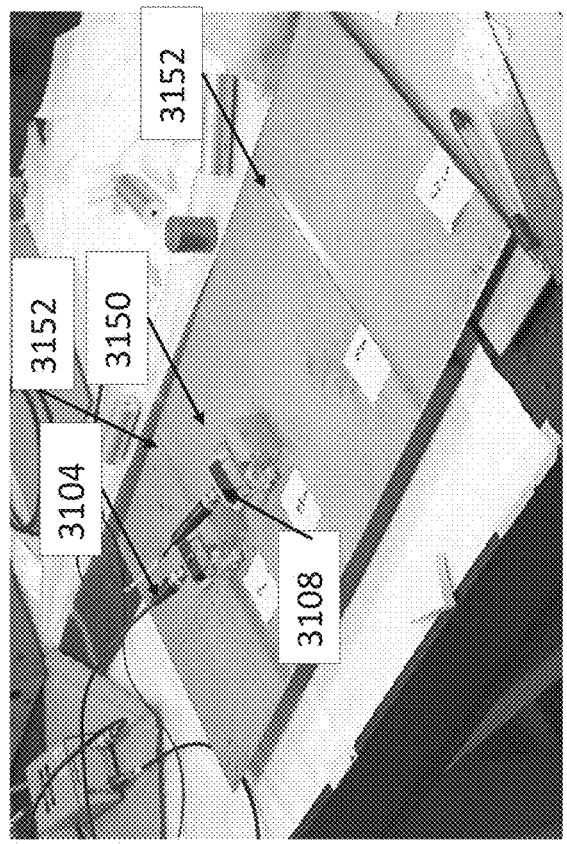
Figure 75:
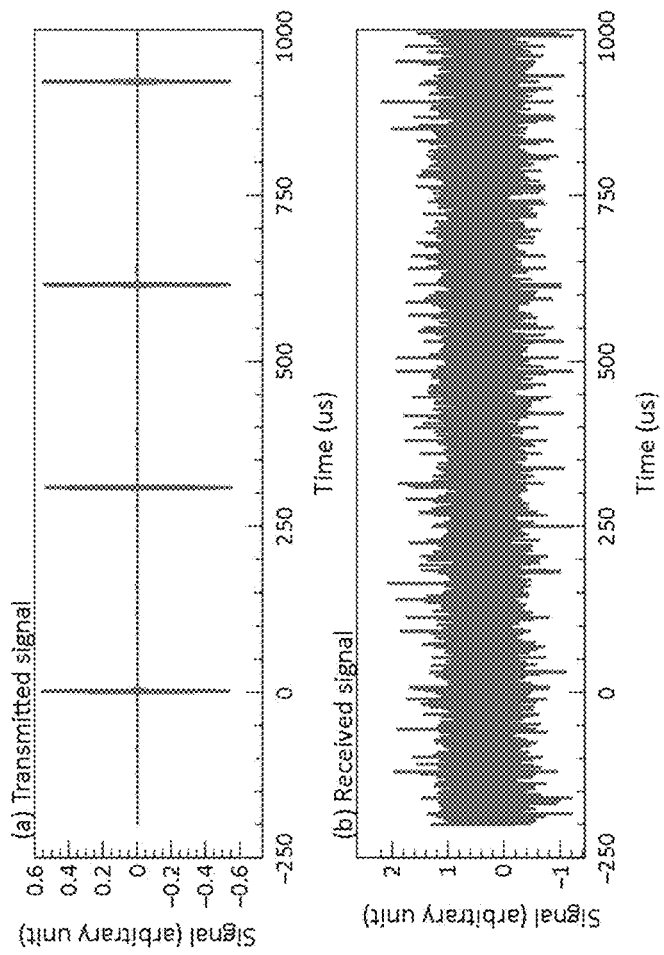
Figure 74:
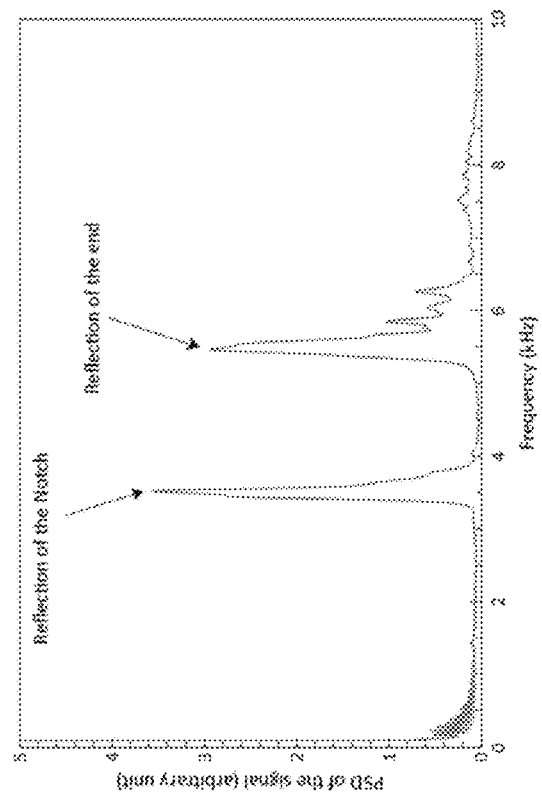
Figure 77:
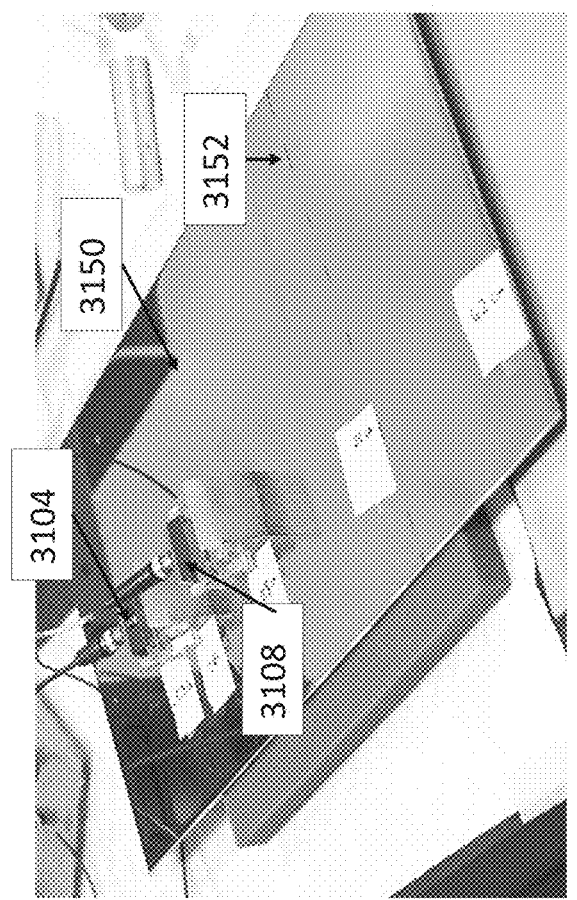
Figure 76:
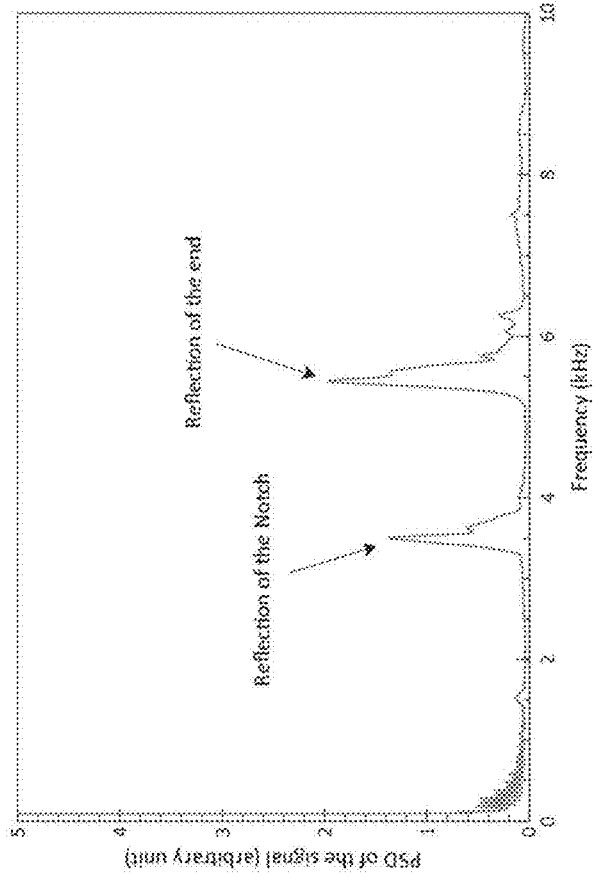
Figure 79:
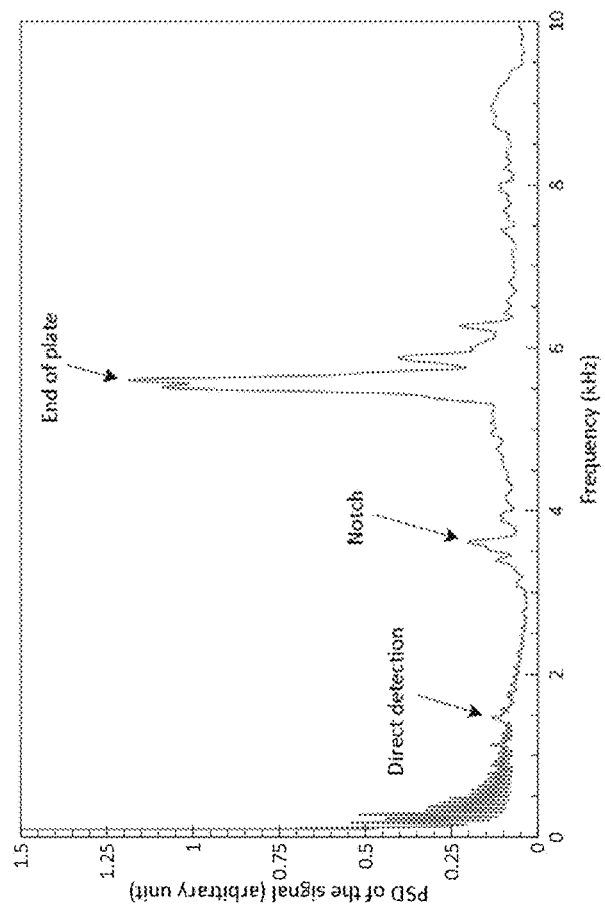
Figure 78:
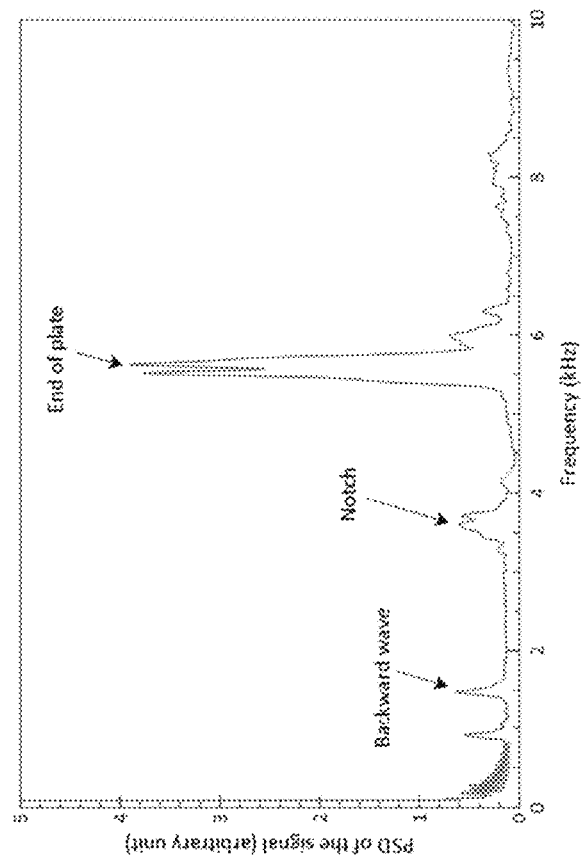
Figure 80:
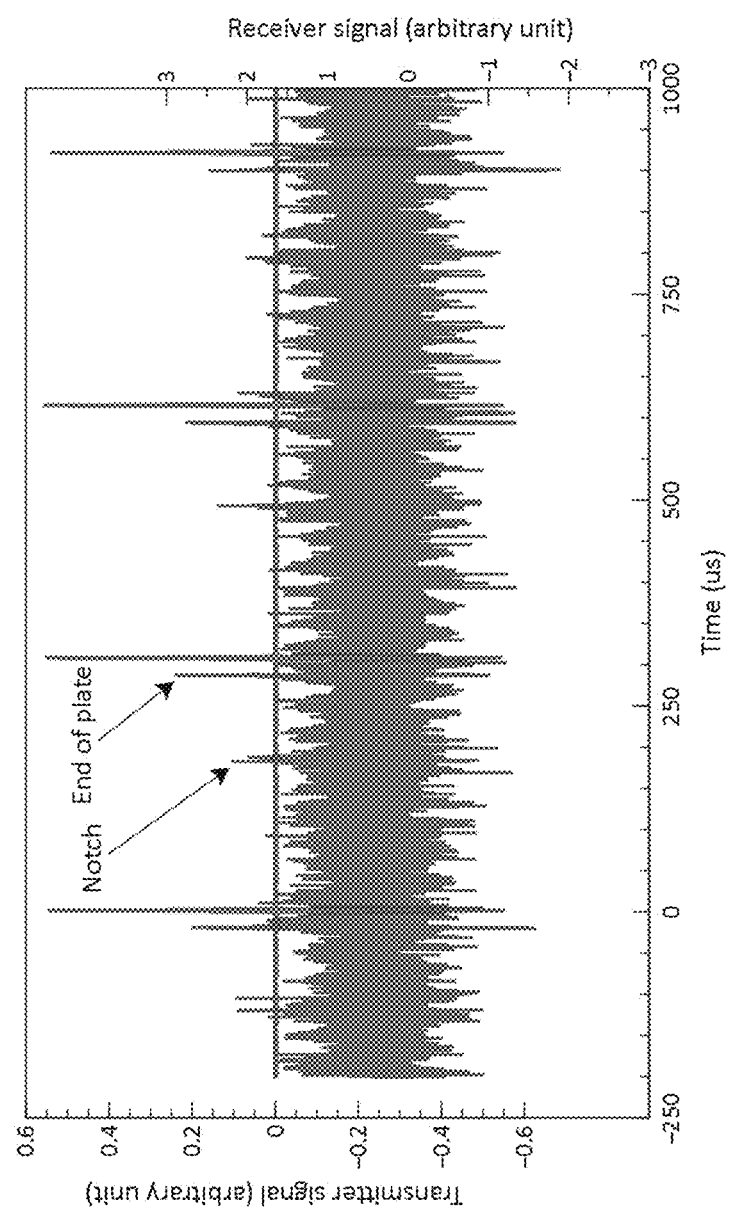

FIG. 65 includes plots of the frequency domain signal for the Inconel tube end reflection test;

FIG. 66 is a photo showing two variable angle wedges and two UT transducers;

FIG. 67 is a schematic diagram of the signal routing system for continuous wave testing on a plate;

FIG. 68 is a photograph of an example of the setup for the through transmission test on a plate;

FIG. 69 includes plots of continuous wave (CW) and pulse signals for various separation distances between transducers;

FIG. 70 is a plot showing wave travel distance versus peak frequency using the CW method;

FIG. 71 is a plot showing wave travel distance versus travel time using the pulse method;

FIG. 72 is a photo of an example of a setup for the reflectors detection test on a plate;

FIG. 73 is an enlarged view of a portion of FIG. 72;

FIG. 74 is a plot showing the continuous wave signal spectrum showing the peak frequencies induced by the reflections;

FIG. 75 is a plot showing pulse-echo signals for transducers located on the same face as the notch (transmitter at the front);

FIG. 76 is a plot showing a continuous wave signal spectrum showing the peak frequencies induced by the reflections;

FIG. 77 is a photo of an example of a setup for the reflectors detection test on a plate;

FIG. 78 is a plot showing a continuous wave signal spectrum for transducers located on the polished face (transmitter at the front);

FIG. 79 is a plot showing a continuous wave signal spectrum for transducers located on the polished face (transmitter at the back);

FIG. 80 is a plot showing pulse-echo signal for transducers located on the polished face (transmitter at the front).

Elements shown in the figures have not necessarily been drawn to scale. Further, where considered appropriate, reference numerals may be repeated among the figures to indicate corresponding or analogous elements.

DETAILED DESCRIPTION

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Mechanical systems (such as buildings, bridges, railways, pipes, boilers, welded structures, etc.) may tend to deteriorate with time. It can be desirable to inspect these systems (both during their production and during their service life) to help ensure that no critical flaws have developed. These inspections can be done using Non-Destructive Testing (NDT) techniques.

In general, a wave can be understood to be a local perturbation of a physical quantity that changes with time as it propagates in space. The perturbation can be of electromagnetic (radio waves) or mechanical (displacement, strain, pressure) nature. Characteristics of a wave such as its amplitude, speed or direction of propagation, may depend on the intrinsic nature of the medium in which it propagates and other factors. As a result, some waves may be at least partially or totally reflected at the interface between two different media, for example due to the change of speed or direction from one medium to the other. These wave properties—reflections and correlations between wave characteristics and material properties—can be used in applications such as underground or underwater probing, flaw detection, position and speed measurement, etc. The term "continuous wave" as used herein can be understood to apply to a variety of waves that have an amplitude and/or frequency for at least substantially the entire time a system is active and can include amplitude- or frequency-modulated continuous waves. This is compared to "pulsed waves" which can be characterized by the presence of "dead time" between pulses while a system is in use. In other words, the continuous wave method is a UT inspection method based on the use of continuous UT waves, generally frequency- or amplitude-modulated. In the continuous wave method, signal analysis techniques are required to extract the wave travel time from the signal. One significant difference between the pulse and continuous wave methods is that for the continuous wave ultrasound method the transmitted and received signals overlap in the time domain, while in the pulsed ultrasound method transmitted and received signals are separated in time.

At least one broad aspect of the teachings herein relates to the use of continuous mechanical waves for ultrasonic inspection. Mechanical waves can be classified into two main categories as used herein: bulk body waves that can propagate deep inside a medium such that the medium can be considered unbounded, and guided waves that tend to see the body as a "whole", and hence, generally satisfy the boundary conditions. Bulk body waves may be suited for local inspection while guided waves may be used for long range inspection due to their extended range of propagation. There is a great variety of guided waves, thanks to the variety of mechanical structures (pipes, rods, plates, etc.). Examples of guided waves include extensional, torsional and flexural waves in slender structures, and surface waves in plate-like structures.

Several NDT techniques are based on the use of pulses to probe the material being tested. Some examples of such techniques include: Ultrasonic Testing (UT), Acoustic Testing, Penetrating Radar, and Pulsed Eddy Current (PEC). Pulsed techniques may tend to have certain limitations, for example: (i) distance measurements and distance resolution may be limited by the propagation speed and the duration of the pulse; (ii) pulsed signals may typically have a relatively low duty-factor, i.e., there may be a limit to the amount of energy used to stimulate the object under test; and (iii) achieving acceptable signal-to-noise ratio (SNR) can sometimes require increasing the amplitude of the pulses, which can lead to reduced life-expectancy of the transducers.

Typically, pulse-based methods (i.e. those using pulsed waves) are generally time-domain back-reflection methods, and time-of-flight is a significant measured parameter.

Ultrasound testing is one example of a known, non-destructive inspection technique that can be used to detect, locate and size discontinuities in a target object. In this method, an electrical signal can be converted to sound/ultrasound energy, which is further inserted into the tested material. Reflected and/or transmitted sound energy is detected and converted into an electrical signal, which can be analyzed. Ultrasound inspection systems of this nature can be based on applying pulsed sound/ultrasound energy to the inspected part and detecting reflected/transmitted pulses. After analysis of the received pulses, different properties of the tested sample and/or the discontinuities present inside the sample can be determined. Usually, the most useful information is the time delay between the transmitted and detected pulse.

Pulsed ultrasound inspection methods can have certain deficiencies in some circumstances. For example, when a single transducer is used for both transmitting and receiving of the pulses, it can be necessary to provide sufficient time between transmitted pulses so that the transducer can receive the reflected pulses. This can limit the overall amount of generated sound/ultrasound energy imparted by the system, which may limit the detectability of some flaws by reducing the signal-to-noise ratio. To help improve the signal-to-noise ratio, the amplitude of the transmitted pulse in such systems is often relatively high, of the order of hundreds of volts. The use of higher voltages of this nature for the pulsed ultrasound technique may reduce the useful lifetime of the transducers and/or may increase the cost of the testing equipment.

In contrast to known, pulsed ultrasound inspection methods and systems, the teachings described herein are related to a continuous wave ultrasound inspection method and systems, which may, in some embodiments, be capable of sufficiently reliable testing of the inspected objects by employing relatively low-voltage signals, and may have relatively improved signal-to-noise ratio of the detected signal as compared to pulsed ultrasound systems. The systems described herein may utilize relatively simplified electronics as compared to known systems.

For example, some embodiments of the continuous wave ultrasound inspection method and systems described herein may be configured to operate in frequency ranges that are relatively lower than the frequency ranges used in pulsed ultrasound systems, which may help to provide a relatively improved signal-to-noise ratio.

The continuous wave ultrasound inspection method and systems described herein may, in some embodiments, be able to operate a relatively lower voltages than conventional systems, which may help reduce the requirement for the voltage applied to the transducer, due to improved signal-to-noise ratio.

The use of a continuous wave ultrasound inspection method and system may help facilitate measurements in relatively highly attenuating materials due, at least in part, to the improved signal-to-noise ratio. This may help provide additional flexibility in configuring the measurements setup, because the interpretation signal may depend not only on the speed of sound, but also on the speed of the frequency ramp and on the bandwidth of the used frequency range in some embodiments.

For example, some embodiments of the continuous wave ultrasound inspection method and systems described herein may be configured to use frequency-modulated ultrasound signals.

This may also help facilitate measurement of relatively short and relatively long distances between the transducers and the flaw, or relatively small and relatively large values of object thickness.

The continuous wave ultrasound inspection systems and methods described herein may be advantageous, when compared to conventional, pulsed systems, in some embodiments because in the continuous wave ultrasound inspection method, the transmitted and received signals may overlap in the time domain, whereas in the pulsed ultrasound inspection method, transmitted and received signals are typically separated in the time domain. In addition, when utilizing a continuous wave ultrasound inspection method, one parameter that can be considered is the difference between the immediate frequency from the function generator and the frequency of the received signal, while in the pulsed ultrasound inspection method, emphasis is usually placed on the time delay between the transmitted and received signals.

Further, the use of pulses may generally require that distances are determined by measuring the time-delay of the transmitted or reflected pulse. In contrast, the continuous wave ultrasound described herein may use a frequency ramp over a broad frequency range (see FIG. 17 and related discussion herein). In such instances, the distances may be determined by measuring the frequency differences. This cannot be done with ultrasound pulses. Changing the speed of the frequency ramp may also allow for additional flexibility to be added which further allows for the control of the interpretation signal outside the speed of sound (while the pulse time delay depends only on the speed of sound in the tested material, the frequency difference depends on both speed of sound in the tested material and on speed of the frequency ramp).

Figure 1:
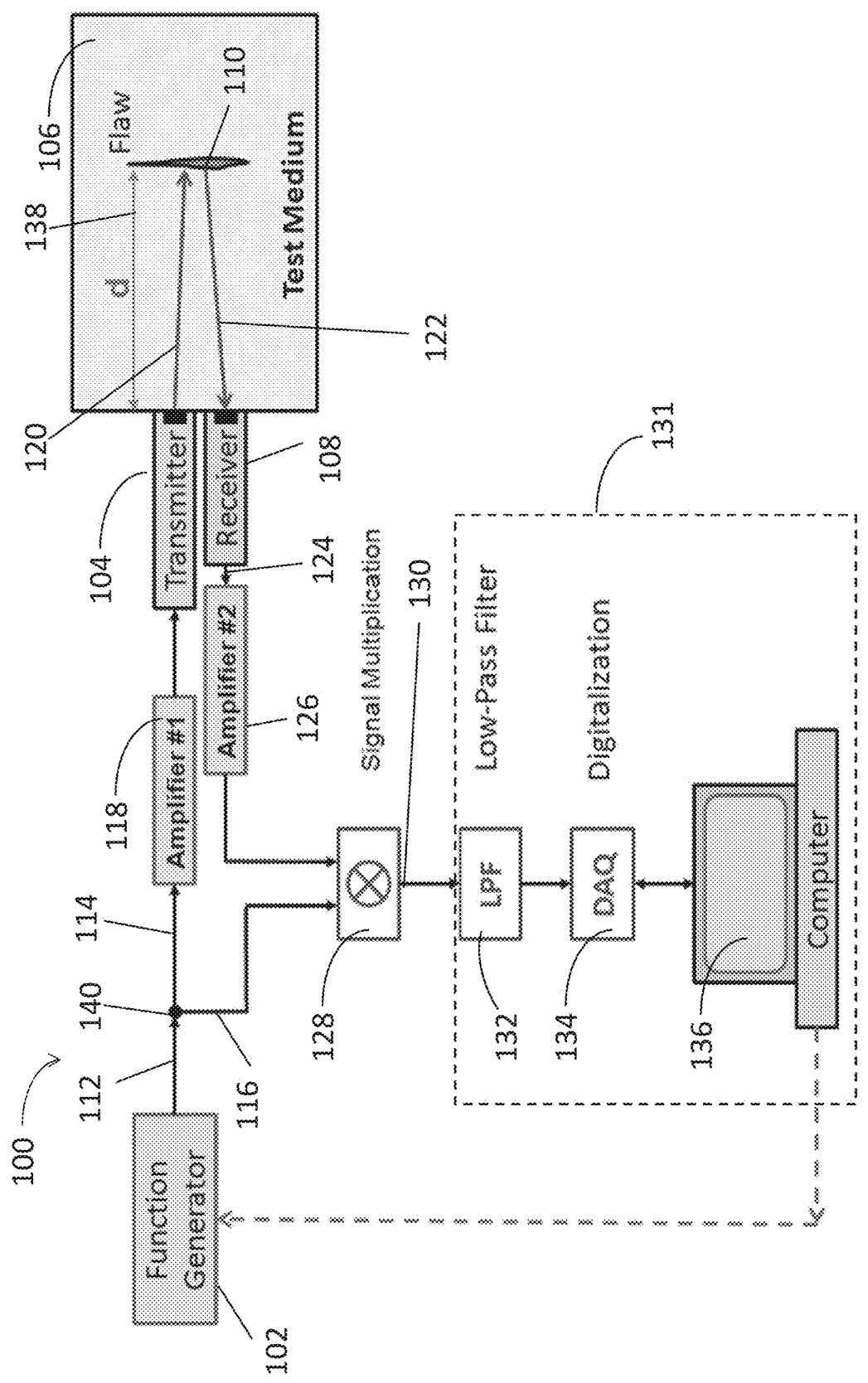
FIG. 1 is a schematic representation of one example of a continuous wave frequency modulated ultrasound inspection system.

Referring to FIG. 1, one example of a continuous wave ultrasound inspection system 100 includes a signal generator 102, a transmitter 104 for introducing a signal into an object 106 and a receiver 108 that is configured to receive a reflection of the signal that has reached a flaw 110 within the object 106.

The ultrasound system 100 may, in some examples, use bulk body waves as the type of mechanical wave that is introduced into the object 106. Such bulk body waves may tend to be bound to satisfy the constitutive equations of the medium in which they propagate. Bulk body waves may tend to propagate "deep in the volume" of a medium such that the medium can be considered "unbounded" or infinite for the purposes of the analysis herein. Systems 100 using bulk body waves may tend to be utilized to conduct local inspections on the object 106. As explained in more detail herein, many aspects of system 100 (and other embodiments described herein) may also be used if the waves generated are guided waves. If the system 100 is configured to utilize bulk body waves, the transmitter 104 may be a bulk wave transducer, such as a piezoelectric UT transducer.

When this embodiment of a system 100 is in use, a frequency modulated (FM) signal can be generated by the function/signal generator 102, which will be further referred to as the generator signal shown as 112. The generator signal 112 may have a frequency range of, for example 20 MHZ, and a frequency ramp speed of between $10^4$ and $10^{14}$ Hz/sec. The FM span of the generator signal 112 can be selected so that it covers the substantially all of the usable frequency range of the transmitter 104. Alternatively, the FM span may cover only a subset of the usable frequency range for a given transmitter 104. In some examples of the systems described herein, the usable frequency span may be selected to be between about 1.5 and about 3 times the transducer centre frequency of a given transducer used, which has been tested for transducers with centre frequencies of between about 0.05 MHz and about 20 MHz.

In this example, the transmitter 104 and receiver 108 have been selected so that they have equal or at least generally similar and/or overlapping frequency ranges.

In the illustrated examples, the signal generator 102 is configured to produce a generally sinusoidal signal with a generally linear frequency ramp, but other types of frequency modulation may be used in other embodiments.

In this embodiment, the generator signal 112 exiting the signal generator 102 is split, by a splitter 140 into a test signal 114 and a reference signal 116. The test signal 114 can then be further amplified by an optional transmitter amplifier 118 and sent to the transmitter 104. Alternatively, in some embodiments, the test signal 114 need not be amplified before being sent to the transmitter 104.

Having received the test signal 114, the transmitter 104 can convert the electrical test signal 114 into a suitable acoustic signal, such as an ultrasound signal 120, and introduce it into the test object 106. The ultrasound signal 120 travels through the object 106 until it reaches an imperfection, such as the flaw 110, the back surface of the object 106 and the like. When the ultrasound signal 120 encounters the flaw 110, at least part of it is reflected toward the receiver 108 as a reflected signal 122.

The receiver 108 can then convert the reflected ultrasound signal 122 back to a corresponding electrical signal 124, which can be referred to as a return signal. The electrical signal 124 exiting the receiver 108 can be further amplified by an optional receiver amplifier 126, as shown in the present example, of alternatively may be directed into the system 100 without further amplification in some embodiments.

The return signal 124 (whether amplified or not) can then be directed into a signal multiplication module 128. The reference signal 116 can also be directed to the signal multiplication module 128 and can be multiplied with the return signal 124. The resulting signal exiting the signal multiplication module 128, annotated as a multiplied signal 130 can be processed using a suitable controller 131 that is configured, as described herein, to determine a distance from transmitter 104 to a feature in the object 106 (such as flaw 110) and back to the receiver 108 (see distance 138). Optionally, the transmitter 104 and receiver 108 need not be at the same distance to flaw 110. For the guided waves tests described herein, the transmitter 104 and receiver 108 were not at the same distance to the flaw 110.

The controller 131 may include a combination of hardware, firmware and/or software (such as a memory, processor, filter, data acquisition apparatus, output device, user input device, user output device or display and the like) and can be configured to process the incoming multiplied signal 130 in the manners described herein to determine and optionally output the desired distance measurements. While shown schematically as including several sub-modules, the controller 131 may be configured as a single device or may include a combination of different devices communicably linked together to provide the desired functions.

For example, in the embodiment of FIG. 1, the controller 131 includes a low-pass filter 132 and a data acquisition apparatus 134 that are communicably linked to processing module 136, which in this embodiment includes a computer (but could include other devices such as other processors, PLCs, tables, smart phones and the like). In this embodiment, the multiplied signal 130 is processed by being passed through a suitable low-pass filter 132 can be digitized using any suitable analog to digital convertor, such as the data acquisition apparatus (DAQ) 134 that is compatible with the processing module 136 that is utilized with the system 100. Optionally, the low-pass filter 132 can be configured to filter out signals that have frequencies below about 1 to about 50 KHz.

Some examples of low-pass filters that can be used with the system 100 (or others described herein) include a hardware low pass filter such as Alligator Technologies USBPGF-S1 programmable low-pass filter and/or a software-based low pass filter such as a Software low-pass filter in Picoscope 2205, Picoscope 2206, Picoscope 5444A and Picoscope 5444B. Some examples of DAQs that are suitable for use with the system 100 (or others described herein) include a computer audio port (24 bits, sampling rate 192 KHz), Picoscope 2205 (8 bits, sampling rate 200 MHz), Picoscope 2206 (8 bits, sampling rate 500 MHZ), Picoscope 5444A (15 bits, sampling rate 125 MHz) and Picoscope 5444B (15 bits, sampling rate 125 MHz).

The processing module 136 may be a computer, as in the illustrated example, but may be another suitable controller having a suitable processor, memory, input/output module and the like.

After the signal 130 has been digitized it can be sent to the processing module 136 for further processing, which may include, for example, applying a Fast Fourier Transform (FFT).

Having converted the signal from the time domain into a frequency domain signal, through application of a time-domain-to-frequency-domain conversion (such as an FFT) for example, the processing module 136 can then automatically determine the distance 138 from the transmitter 104 to the flaw 110 (or to any other feature in the object that generates a reflected signal, e.g., the edge of the object 106) based on the speed of sound, the frequency ramping speed and the measured peak frequency obtained from the FFT. As the speed of sound v and the frequency ramping speed $\Delta f$ are known for a given embodiment, and the frequency $f_R$ is measured during the use of the system 100, the distance 138, represented as $d_i$ in the equations herein, can be determined in accordance with the following function:

$$d_i = \frac{v \cdot f_R}{2 \cdot \Delta f}$$

Figure 21:
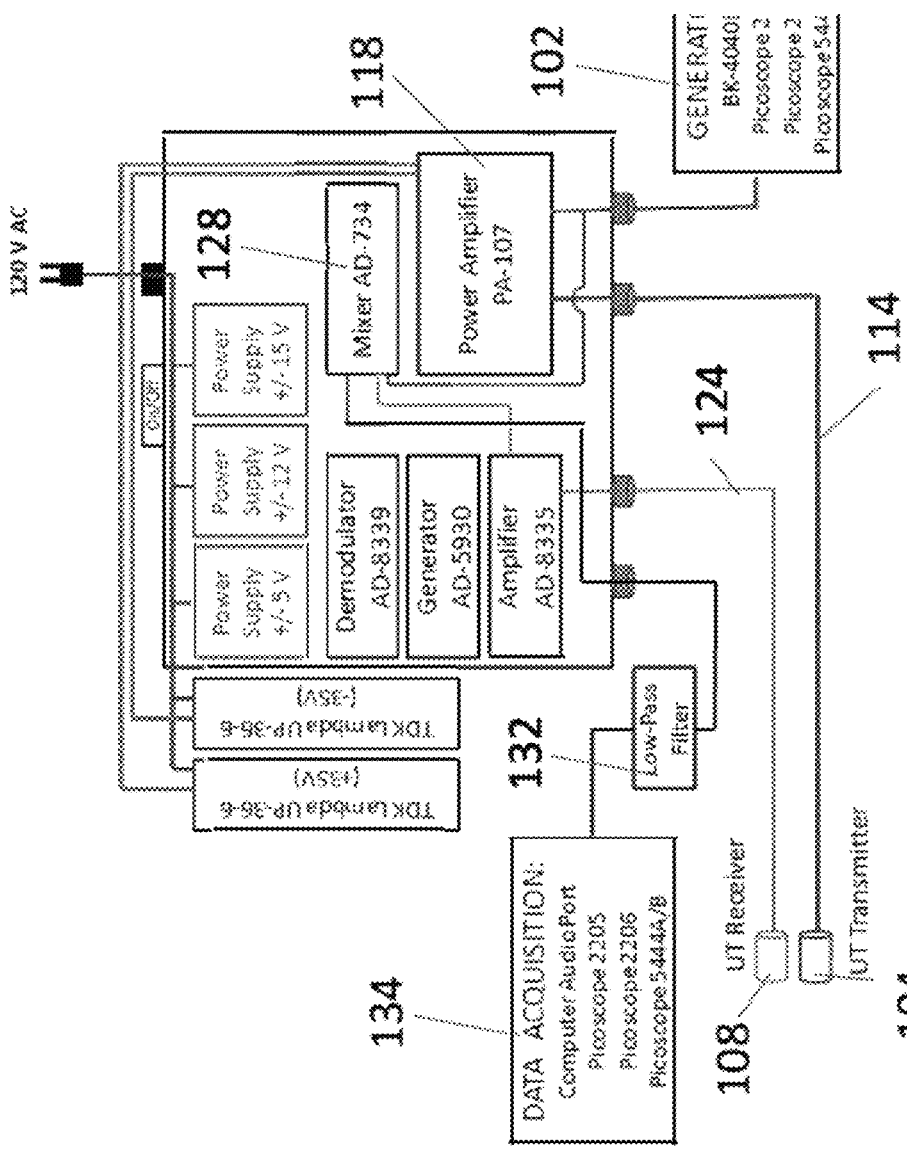
FIG. 21 is a schematic representation of one experimental version of continuous wave frequency modulated ultrasound inspection system.

The system 100 may be configured for use with a relatively low-frequency region of frequency modulation, up to a maximum frequency of about 20 MHZ, with a preferred response of the power amplifier being achieved below about 2 MHZ. The signal generator 102 used may be of any suitable type, including, for example, BK Precision 4040B (up to 20 MHz, up to 5V), Picoscope 2205 (up to 100 kHz, up to 2V), Picoscope 2206 (up to 1 MHZ, up to 2V), Picoscope 5444A (up to 20 MHz, up to 2V) and Picoscope 5444B (up to 20 MHZ, up to 2V). Another schematic representation of some of the features of the system 100 is shown in FIG. 21.

Figure 2:
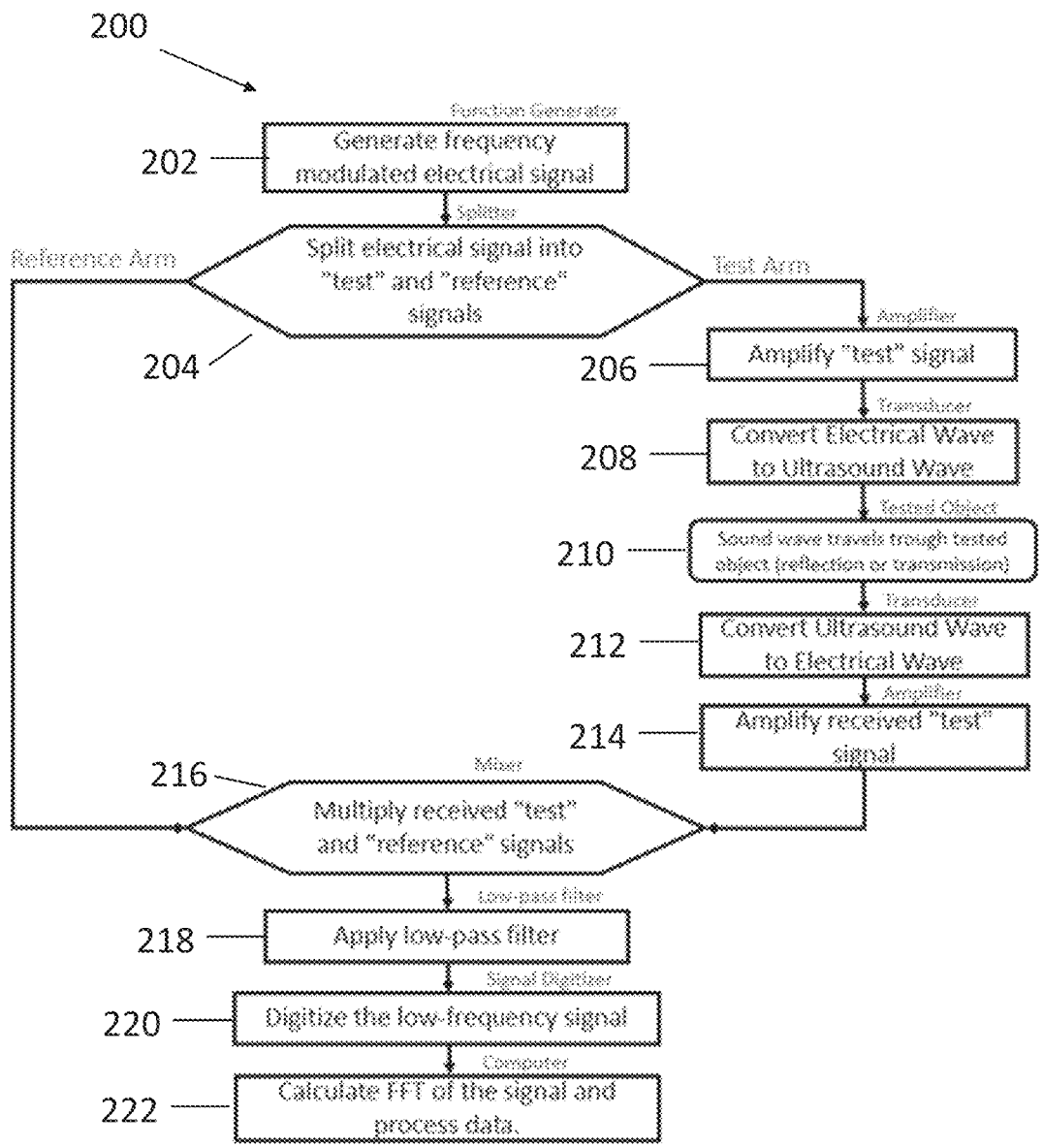
FIG. 2 is a flow chart of one example of a continuous wave frequency modulated ultrasound inspection method.

Referring to FIG. 2, one example of a continuous wave ultrasound inspection method 200 includes, at step 202, generating a frequency-modulated electrical signal 112 with a suitable function generator, such as signal generator 102.

Step 204 includes splitting the frequency-modulated electrical signal into the test signal 114 and reference signal 116.

Having split the generated signal 112, the method 200 can progress to step 206, in which an amplifier is used to amplify the test signal 114. In the illustrated example, the test signal 114 is amplified using the transmitter amplifier 118.

At step 208, the amplified test signal 114 can then be converted to a continuous ultrasound wave 120 using the ultrasonic transmitter 104 that is positioned adjacent the object 106 to be inspected. The transmitter 104 may be any suitable transducer, including those described herein.

At step 210, the ultrasound wave 120 travels through the object 106 and may encounter a flaw 110, if present, within the object 106. The interaction between the ultrasound wave and the flaw 110 can generate a reflection 122 of the ultrasound wave that can travel back toward the receiver 108.

Such reflected sound waves 122 can, at step 212 be received and detected by the ultrasonic receiver 108 (which may be any suitable transducer). The receiver 108 can then convert the reflected ultrasound waves 122 into a corresponding received return electrical signal 124.

At step 214, the return signal 124 is passed to the amplifier 126 which can increase the amplitude of the return signal 124.

The return signal 124 can then be provided as one input into the mixer/signal multiplier module 128 where the amplified return signal 124 signal is multiplied, at step 216 with the reference signal 116 generated at step 204.

The multiplied electrical signal 130 can then be output from the signal multiplier 128 and passed through the low-pass filter 132, at step 218. The output from the low-pass filter 132 can then be digitized, at step 220, using any suitable signal digitizer, such as the DAQ 134. Optionally, these steps may be performed in different order so that the signal may be digitized first (step 220) and then subsequently digitally filtered (step 218).

At step 222, the digitized signal can be provided to the system controller 131, which can include a processor that is configured to apply a Fast Fourier Transform (FFT) of the digitized low-frequency signal 130 and to further process the data. For example, the controller may be configured to calculate the distance 138 between the receiver 108 and the flaw 110, in accordance with the functions and equations described herein.

Figure 3:
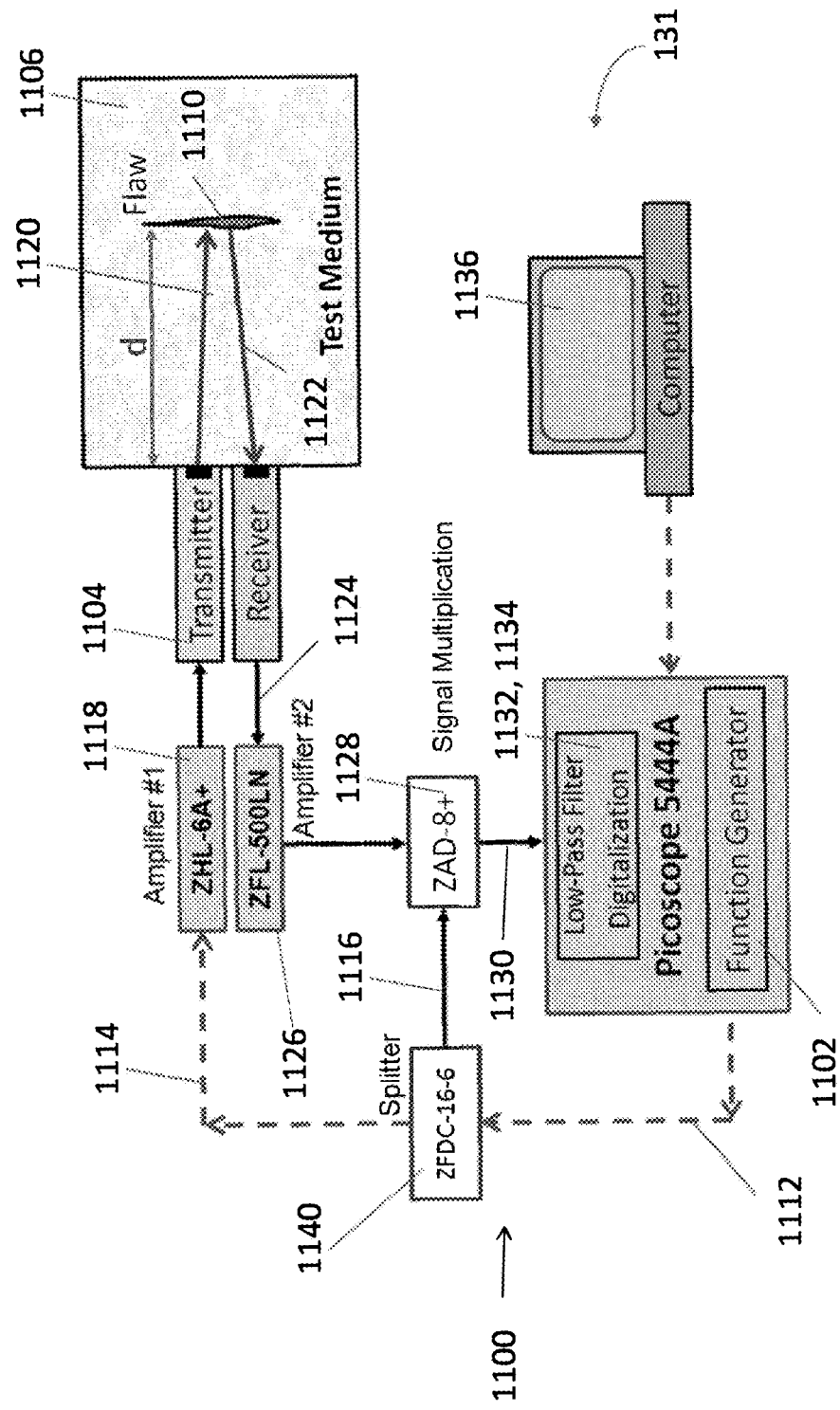
FIG. 3 is a schematic representation of another example of a continuous wave frequency modulated ultrasound inspection system.

Referring to FIG. 3, another example of a continuous wave frequency-modulated ultrasound inspection system 1100 is generally analogous to the continuous wave frequency modulated ultrasound inspection system 100, with like features annotated using like reference characters indexed by 1000. In this embodiment, the system 1100 includes a signal generator 1102 for generating a continuous, frequency modulated electric signal 1112.

In this example, the amplifier 1118 is a Broadband signal amplifier Mini-Circuits ZHL-6+, Gain ×43, Input<0.2 V, output<8 V and the amplifier 1126 is a Broadband signal amplifier Mini-Circuits ZFL-500LN, Gain ×33, Input <0.03 V, output <1 V. The splitter 1140 is a Mini-Circuits ZFDC-16-6 and the signal multiplication module 1128 is a Mini-Circuits ZAD-8+(or ZFY-1+, or ZP-3H+). A Picoscope 5444A is used to provide the signal generator 1102, low-pass filter 1132 and DAQ 1134.

Figure 4:
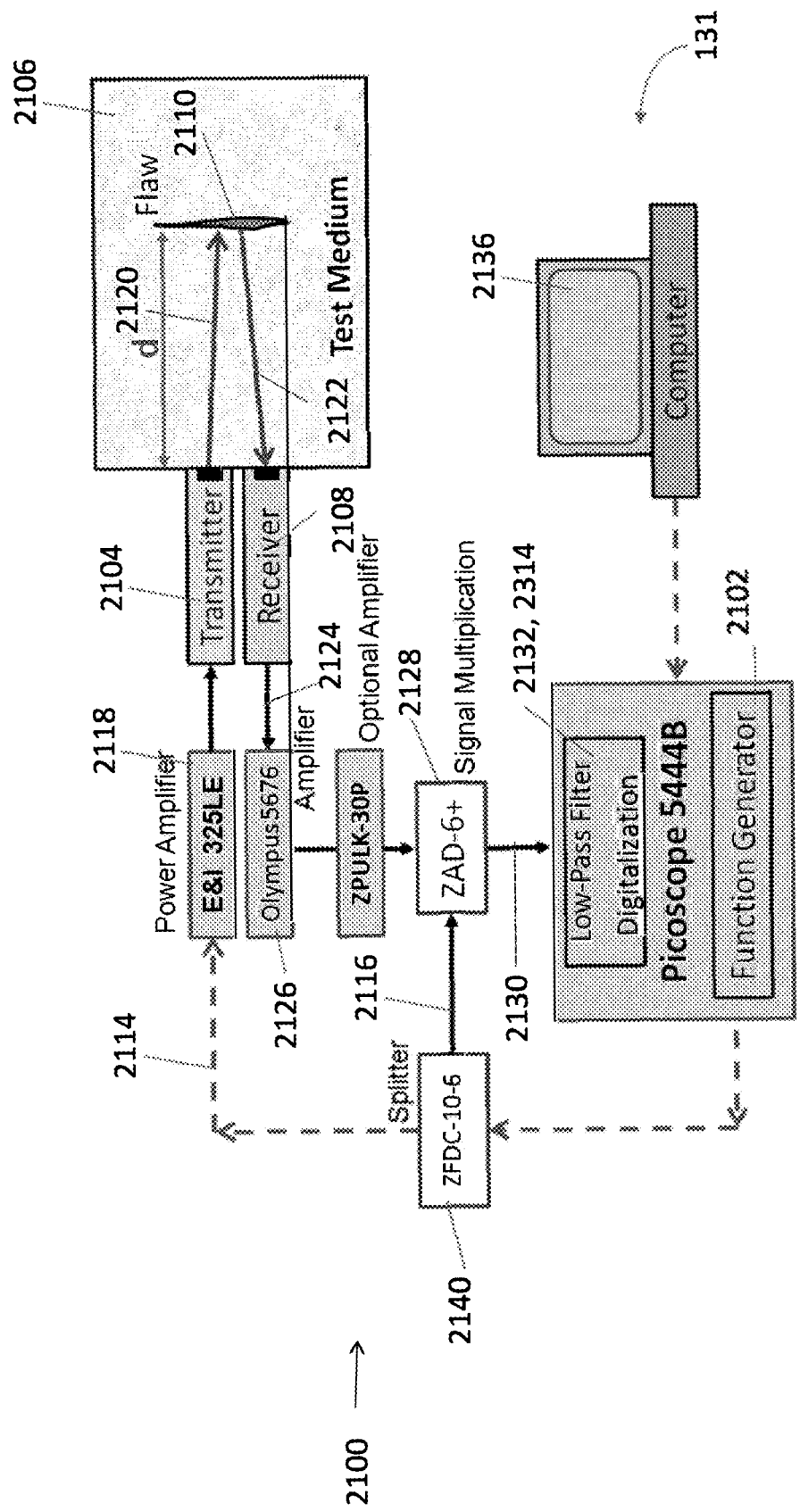
FIG. 4 is a schematic representation of another example of a continuous wave frequency modulated ultrasound inspection system.

Referring to FIG. 4, another example of a continuous wave frequency-modulated ultrasound inspection system 2100 is generally analogous to the continuous wave frequency modulated ultrasound inspection system 100, with like features annotated using like reference characters indexed by 2000. This embodiment is generally similar to the others described herein but has been configured to include relatively more powerful amplifiers which help facilitate use of the system 2100 for waveguide measurements.

In this embodiment, the amplifier 2118 is a Broadband power amplifier E&I 325LA, Gain ×300, Input <0.2 V, output <60 V and the amplifier 2126 is a Broadband pre-amplifier Olympus 5676, Gain ×150, Input <0.03 V, output <5 V. The splitter 2140 is a Mini-Circuits ZFDC-10-6 and the signal multiplication module 2128 is a Mini-Circuits ZAD-6+(or ZAD-8+, or ZFY-1+, or ZP-3H+). The low-pass filter 2132, digitization module 2134 and signal generator 2102 are provided by a Picoscope 5444B.

Optionally, as shown in FIGS. 1, 3 and 4 the transducers (transmitter 104 and receiver 108) can be positioned on the same side of the object being examined. This may be suitable for flaw detection. In other examples, the transmitter and receiver may be positioned on opposite sides of the object being examined, which may be useful for measuring the thickness of the object.

The systems and methods described herein have been at least substantially demonstrated by the inventors, and some examples of the theoretical and empirical support for the described systems and methods follow. The examples and experiments described herein are only some examples of the testing and validation that has been conducted by the inventors.

The description that follows is an explanation of the derivation of the distance function described herein, for a single reflection. In this example, the Linear Frequency Modulation (LFM) can be written as:

$$f(t)=f_0+\Delta f \cdot t \text{ or } \omega(t)=2.\pi.f(t)=2.\pi.(f_0+\Delta f \cdot t) \quad (1)$$

where $\Delta f$ is the frequency ramp [Hz/sec], and $f_0$ is the start frequency at time t=0.

The dependence of the phase of the LFM signal on the time is given as:

$$\varphi(t) = \int_0^t \omega(t) \cdot dt = 2 \cdot \pi \cdot f_0 \cdot t + \pi \cdot \Delta f \cdot t^2 \quad (2)$$

The voltage of the LFM signal coming out from the signal generator 102 can be expressed as:

$$V(t)=V_0 \cdot \sin(\varphi(t)=V_0 \cdot \sin(2.\pi.f_0 \cdot t+\pi.\Delta f \cdot t^2) \quad (3)$$

The reference signal 116 travels directly from the signal generator 102 to the signal multiplication module 128 and will have the same amplitude as V(t). The test signal after the receiver amplifier (e.g. amplifier 126 in FIG. 1) is given as:

$$V_2(t)=k \cdot \sin(2.\pi.f_0 \cdot (t-2.\tau_i)+\pi.\Delta f \cdot (t-2.\tau_i)^2) \quad (4)$$

where:
  k is a proportionality constant (this will depend on gains of the amplifiers, on the absorption of the ultrasound in the test medium, on the amount of energy reflected by the flaw, on temperature, on frequency, etc., but none of these dependencies will have periodic characteristics).

$\tau_i$ is time required for the sound to travel from the transmitter to the flaw.

$$\tau_i = \frac{d_i}{v} \quad (5)$$

$d_i$ is the distance 138 to the flaw 110 "i".

v is the speed of the sound in the test object 106 (assumed to be constant).

Voltages V(t) and $V_2$(t) are introduced at the inputs of the signal multiplication module 128. That is, multiplying two sinusoidal signals with frequencies together. The reference signal 116 will have frequency $f(t)=f_0+\Delta f \cdot t$. The test signal 114 will have frequency $f(t-2.\tau_i)=f_0+\Delta f \cdot (t-2.\tau_i)$, because it was generated at a time $(t-2.\tau_i)$. That is, the system can account for the fact that this signal needs additional "travel" time of $t-2.\tau_i$ to reach the signal multiplication module 128.

The multiplied signal 130 after the signal multiplication module 128 will be:

$$V_M(1)=K.[\sin(2.\pi.f_0 \cdot t+\pi.\Delta f \cdot t^2) \cdot \sin(2.\pi.f_0 \cdot (t-2.\tau_i)+\pi.\Delta f \cdot (t-2.\tau_i)^2)] \quad (6)$$

The new proportionality constant K may depend on previously introduced constant k and on the characteristics of the signal multiplication module 128. As:

$$\sin(a) \cdot \sin(b) = \frac{1}{2} \cdot [\cos(a-b) - \cos(a+b)] \quad (7)$$

$$\cos(-a) = \cos(a)$$

After the signal multiplication module 128 there may be two frequencies: the sum and the difference of the frequencies entering the mixer:

$$V_M(t) = \frac{K}{2} \cdot [\cos(C_{LF}) - \cos(C_{HF})] \quad (8)$$

where $$C_{LF} = 2\pi \cdot [2 \cdot \tau_i \cdot \Delta f \cdot t + 2 \cdot \tau_i \cdot (f_0 - \Delta f \cdot \tau_i)] \quad (9)$$

$$C_{HF} = 2\pi \cdot [2\tau_i \cdot (f_0 + \tau_i \cdot \Delta f) + 2 \cdot (f_0 + \tau_i \cdot \Delta f) \cdot t + \Delta f \cdot t^2] \quad (10)$$

$$f_R = f(t) - f(t - 2 \cdot \tau_i) = 2 \cdot \tau_i \cdot \Delta f = 2 \cdot \frac{d_i}{v} \cdot \Delta f \quad (11)$$

Here $f_R$ represents the frequency difference between the signals 114/116 and 124, and this parameter may be proportional to the distance to the flaw 110. This is the parameter which can be measured by continuous wave frequency-modulated ultrasound inspection system 100. If $\tau_i=0$, then $C_{LF}=0$ and CHF corresponds to doubling the frequency. After the low-pass filter 132, only the low-frequency signal will remain ($\gamma$ is the transmission coefficient of the low-pass filter), i.e.:

$$V_{LPF}(t) = \gamma \cdot \frac{K}{2} \cdot \cos(2\pi \cdot [2 \cdot \tau_i \cdot \Delta f \cdot t + 2 \cdot \tau_i \cdot (f_0 - \Delta f \cdot \tau_i)]) \quad (12)$$

After digitization of $V_{LPF}(t)$, a FFT can be performed on the multiplied signal 130. The Fourier Transform of a cosine function is a delta-function, i.e., in the Fourier spectrum of $V_{LPF}(t)$ we will get a peak at frequency $f_R$ (see Equation 11):

$$\mathcal{F}(A \cdot \cos(2\pi \cdot f_R \cdot t)) = \frac{A}{2} \cdot \delta(+f_R) + \frac{A}{2} \cdot \delta(-f_R) \quad (13)$$

As the speed of sound v and the frequency ramping speed $\Delta f$ are known, and the frequency $f_R$ can be measured, it is then possible to determine the distance 138 to the flaw 110, represented as d as:

$$d_i = \frac{v \cdot f_R}{2 \cdot \Delta f} \quad (14)$$

In addition to the single reflection equation above, a derivation of an equation for use with mixed-reflection terms has also been derived. If an object 106 includes two (2) reflectors (e.g. flaws 110), at different distances 138 from the entrance surface, represented as $d_1$ and $d_2$ in the equations herein, then the system 100 may receive three signals at the signal multiplication module 128. That is, the reference signal 116 from signal generator 102 and two reflected signals 124:

$$V(t) = V_0 \cdot \sin(2 \cdot \pi \cdot f_0 \cdot t + \pi \cdot \Delta f \cdot t^2)$$

$$V_{R1}(t) = K_{R1} \cdot \sin(2 \cdot \pi \cdot f_0 \cdot (t - 2 \cdot \tau_1) + \pi \cdot \Delta f \cdot (t - 2 \cdot \tau_1)^2)$$

$$V_{R2}(t) = K_{R2} \cdot \sin(2 \cdot \pi \cdot f_0 \cdot (t - 2 \cdot \tau_2) + \pi \cdot \Delta f \cdot (t - 2 \cdot \tau_2)^2) \quad (15)$$

Assuming the reflected signals are coherent (i.e., their amplitudes can multiply), there will be a mixed term. After the Low-Pass filter 132, there will be two single-reflection terms (Equations 16 and 17), and one mixed-reflection term (Equation 18):

$$V_{LPF1}(t) \approx \cos(2\pi \cdot [2 \cdot \tau_1 \cdot \Delta f \cdot t + \phi_{R1}]) \quad (16)$$

$$V_{LPF2}(t) \approx \cos(2\pi \cdot [2 \cdot \tau_2 \cdot \Delta f \cdot t + \phi_{R2}]) \quad (17)$$

$$L_{LPF}^{DR}(t) \approx \cos(2\pi \cdot [2 \cdot (\tau_1 - \tau_2) \cdot \Delta f \cdot t + \phi_{12}]) \quad (18)$$

Figure 5:
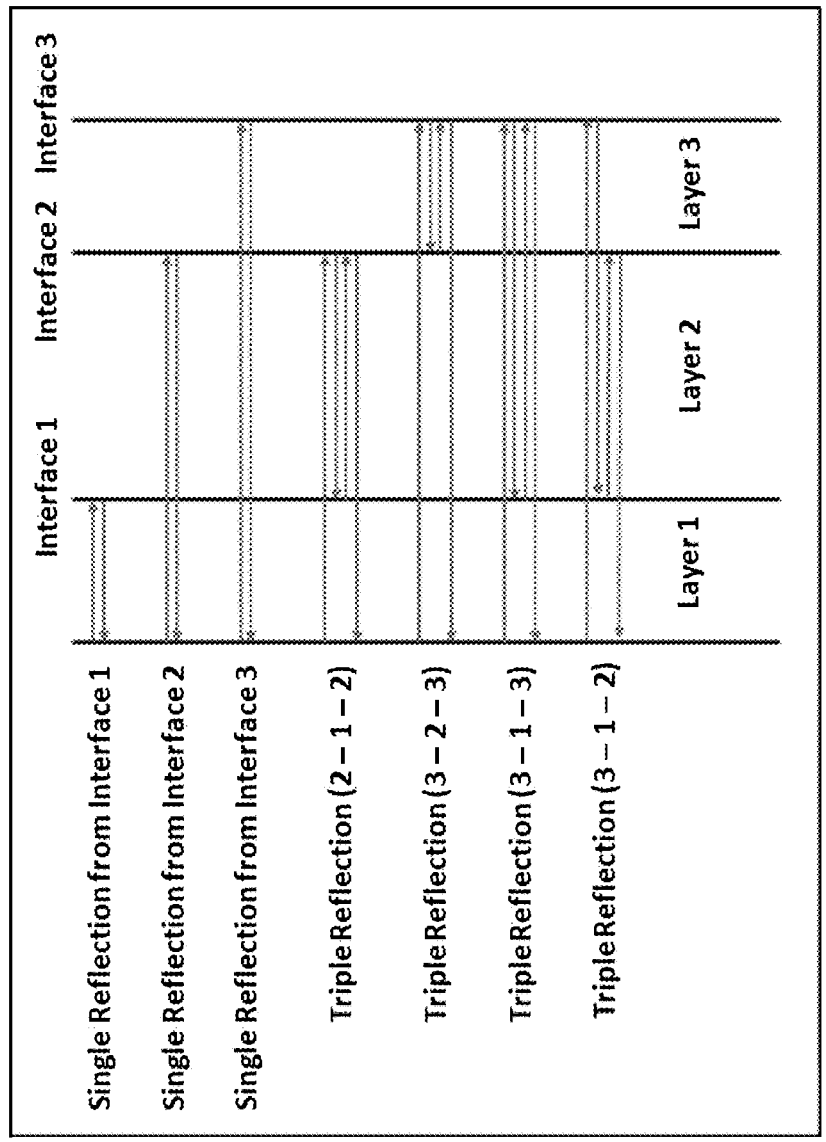
FIG. 5 is a schematic diagram showing triple reflection case for three interfaces.

The inventors have also considered the derivation of an equation for triple-reflection terms. Triple-reflection is multiplication of a beam which is reflected from three interfaces (an odd number of direction changes in order to have back-reflection) with the reference beam. If this multiplication is performed by the signal multiplication module 128, this term may be present. There are several different possibilities for triple-reflections to reach the detector, including those illustrated in FIG. 5. Generally, if "N" is the number of reflecting interfaces, then the calculation of the triple reflection terms can follow the following scheme:

For i=2 to N (first reflection interface)
  For j=1 to (i−1) (second reflection interface)
    For k=(j+1) to N (third reflection interface)
      Calculate Ti (delay to first reflection interface)
      Calculate Tij (delay from first to second reflection interface)
      Calculate Tjk (delay from second to third reflection interface)
      Calculate Tk (delay from third interface to detector)
      Calculate Ai (attenuation to first reflection interface)
      Calculate Aij (attenuation from first to second reflection interface)
      Calculate Ajk (attenuation from second to third reflection interface)
      Calculate Ak (attenuation from third interface to detector)
      Calculate triple-reflection signal
    Next k
  Next j
Next i The triple-reflected test signal after the receiver amplifier 126 may be:

$$V_2(t) = A_i \cdot A_{ij} \cdot A_{jk} \cdot A_k \cdot \sin([2\pi f_0 + \pi \Delta f \cdot (t - T_i - T_{ij} - T_{jk} - T_k) \cdot (t - T_i - T_{ij} - T_{jk} - T_k)]) = A_{jk} \cdot \sin([2\pi f_0 + \pi \Delta f \cdot (t - \tau)] \cdot (t - \tau)) \quad (19)$$

If:

$$A_{jk} = k \cdot A_i \cdot A_j \cdot A_{jk} \cdot A_k.$$

$$\tau = T_i + T_{ij} + T_{jk} + T_k$$

then the low-frequency component for the triple-reflection terms may be proportional to:

$$V_{LPF}^{TR}(t) \sim A_{ijk} \cdot \cos(2\pi \cdot [2 \cdot \tau \cdot \Delta f \cdot t + 2 \cdot \tau \cdot (f_0 - \Delta f \cdot \tau)]) \quad (20)$$

And this equation is practically identical to equation (12), which describes the single-reflection terms.

To help evaluate the systems and methods described herein, two different software programs were developed to model the detected signal of the proposed continuous wave modulated-frequency ultrasound inspection systems.

Figure 6:
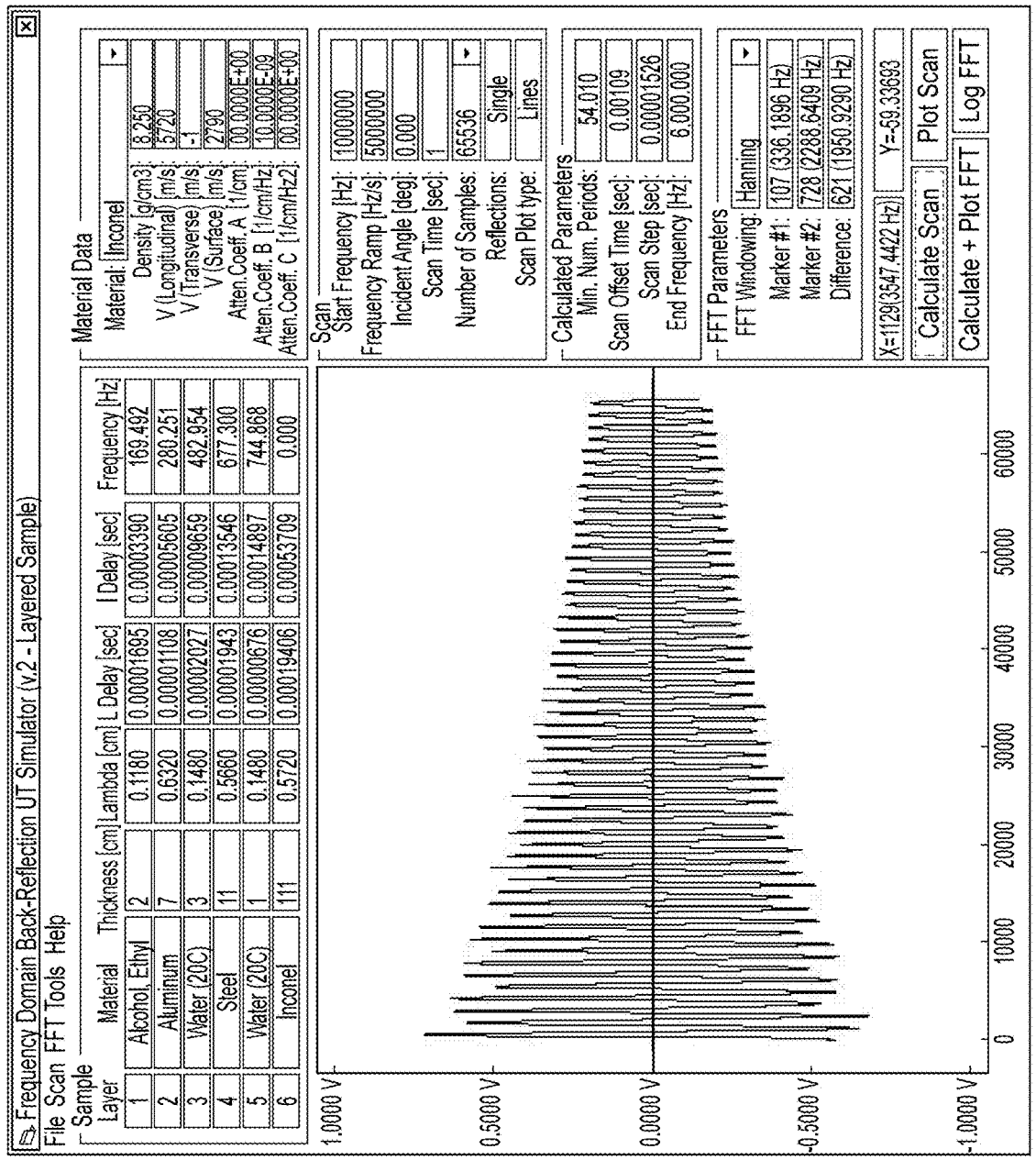
FIG. 6 is a screen capture of a simulated continuous wave frequency modulated ultrasound inspection signal from 5 interfaces.
Figure 7:
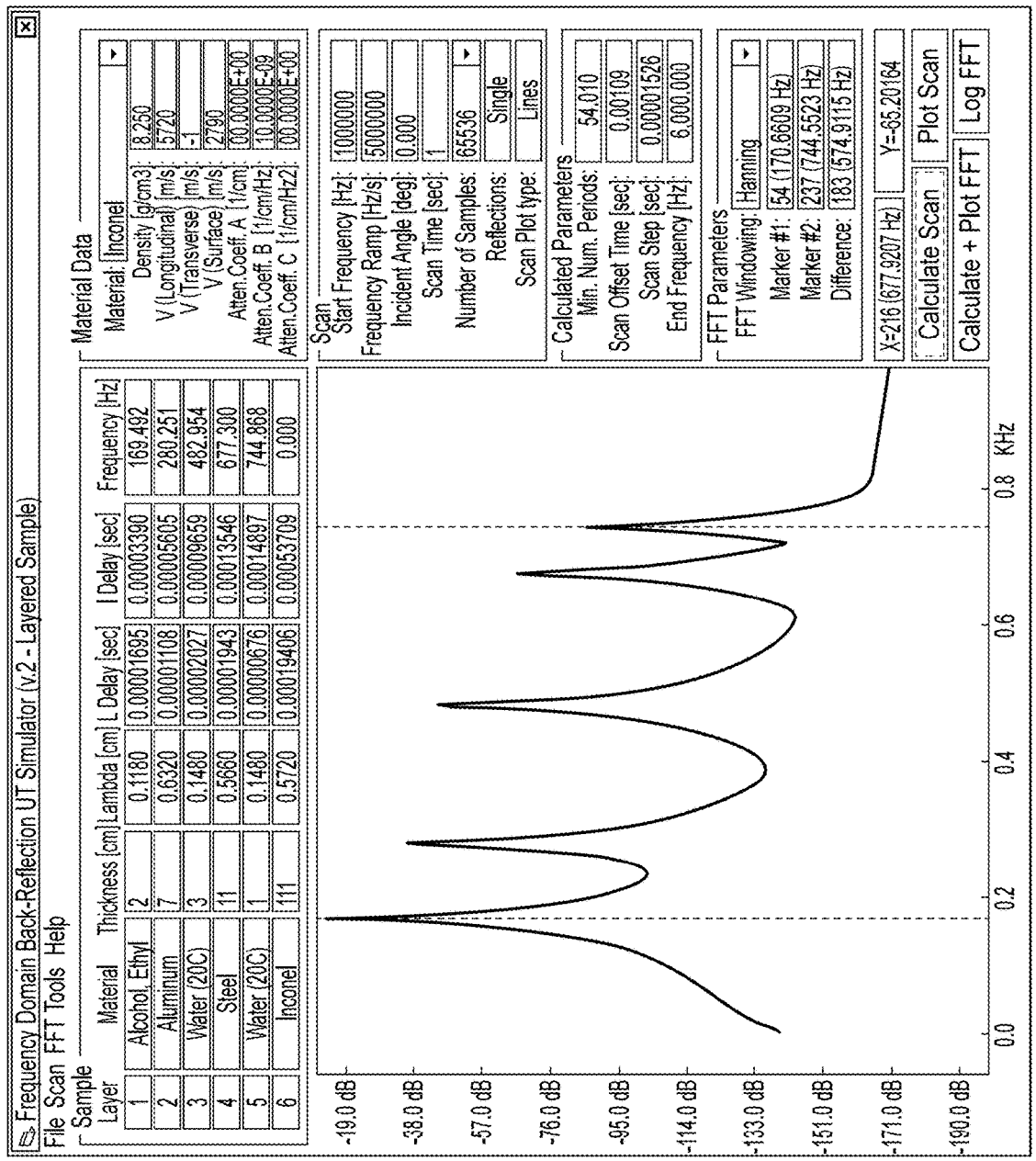
FIG. 7 is a FFT of the data presented in FIG. 6.
Figure 8:
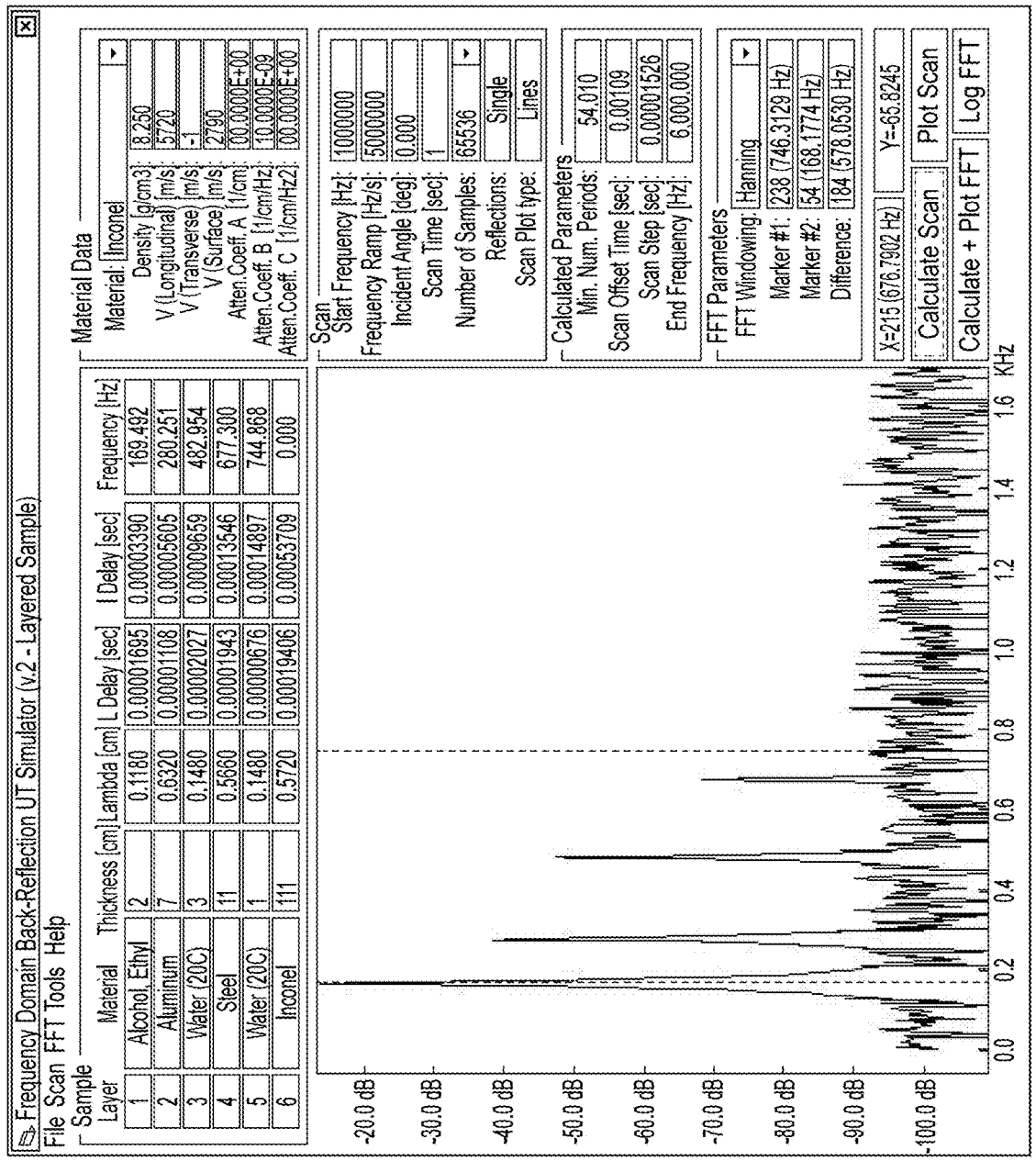
FIG. 8 is a FFT of the data presented in FIG. 6 with added random noise.
Figure 9:
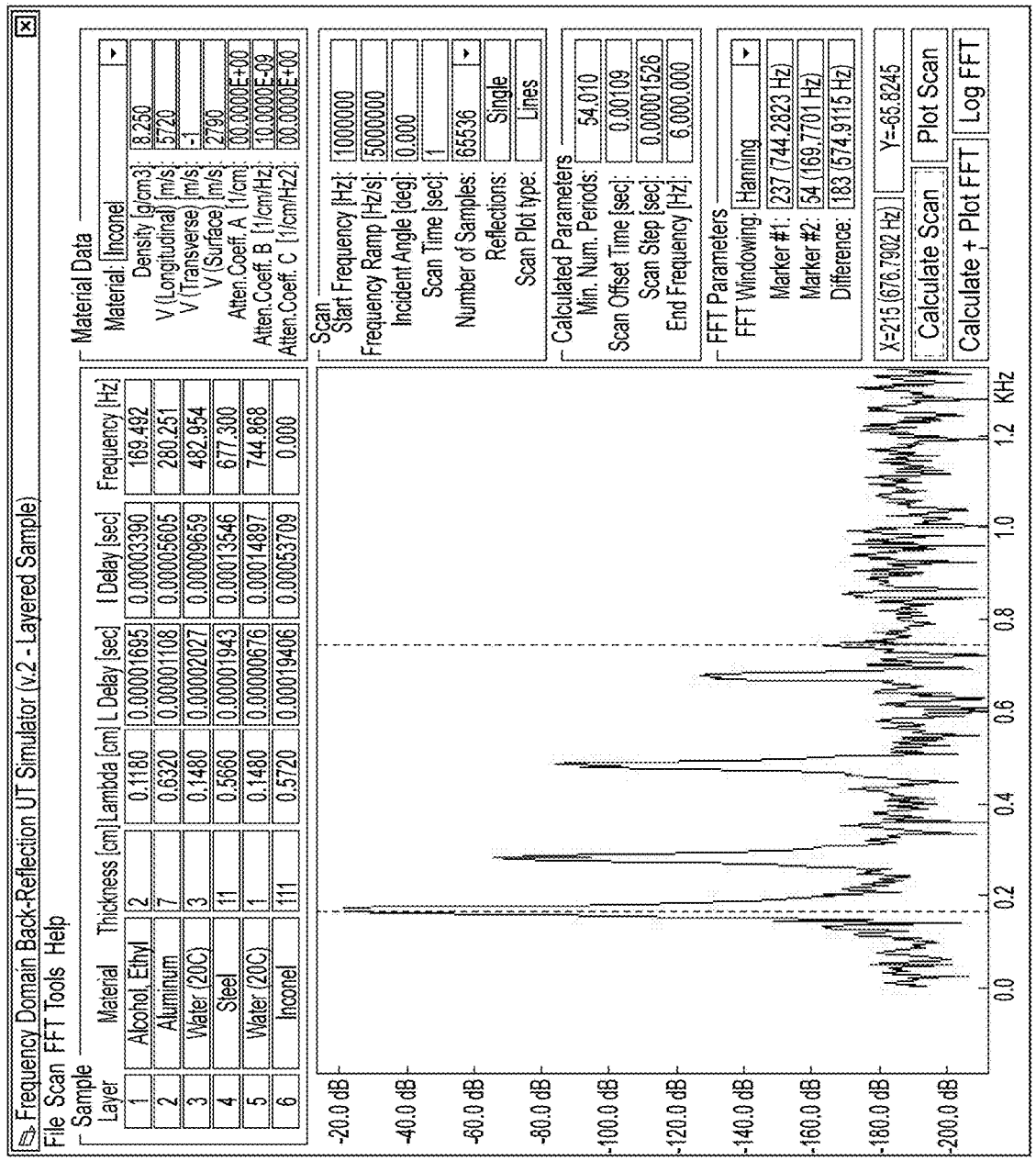
FIG. 9 is a FFT of the data presented in FIG. 6 with added random noise and autocorrelation.
Figure 10:
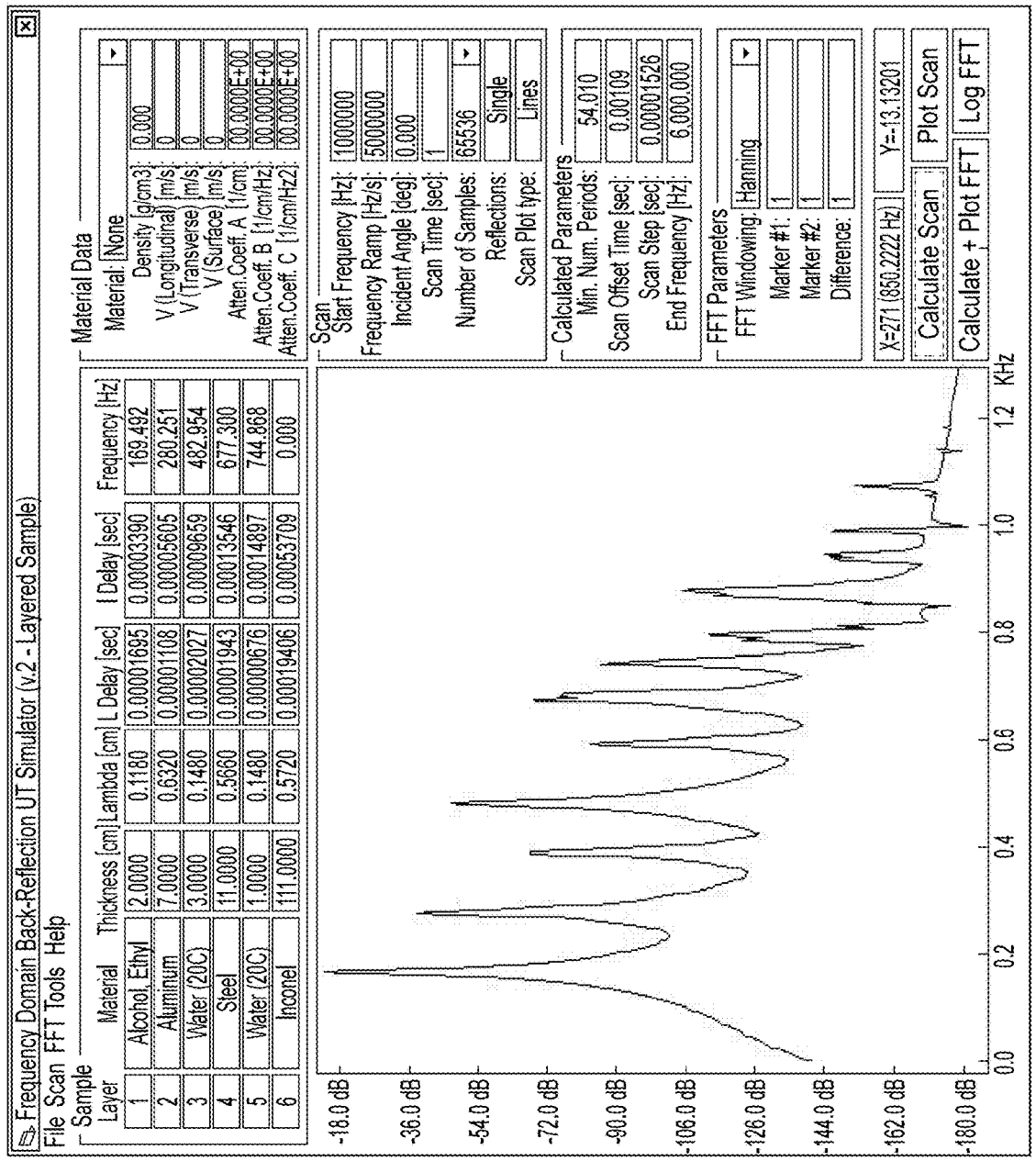
FIG. 10 is a FFT of the data presented in FIG. 6, with triple-reflection included.
Figure 11:
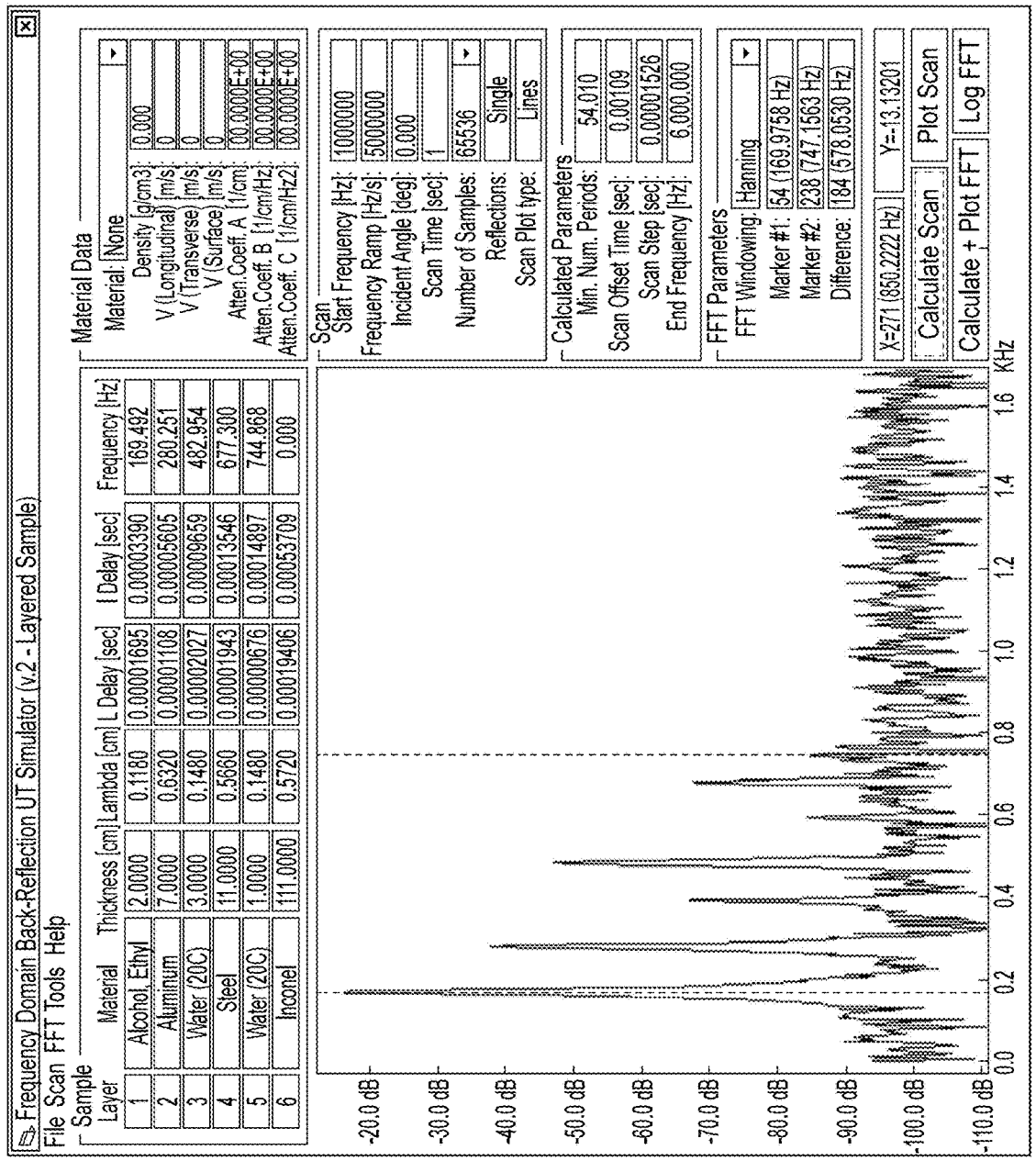
FIG. 11 is the data presented in FIG. 10 with added noise.

A first version of the software was aimed at modeling multi-layered structures, composed of several (for example, up to 6) layers of different materials. A screenshot of the program showing the simulated signal from a CWFMUIS from a 6-layer sample (5 interfaces) is presented in FIG. 6. The FFT of the same signal is presented in FIG. 7. As can be seen, the FFT peaks corresponding to each interface are clearly observable. The FFT of the signal shown in FIG. 6, after adding 3% random noise (1% additive and 2% multiplicative) to each measured point, is presented in FIG. 8. The FFT peak corresponding to the last interface is not visible. The noise level is about 80 dB below the highest peak. The processing of the same data used for FIG. 8 is shown in FIG. 9, but an autocorrelation was performed before applying the FFT procedure. As can be seen, a weak peak can be observed from the 5-th (last) interface, so it can be concluded that applying autocorrelation before applying FFT improves the detection capabilities of the method. FIGS. 7 to 9 show single-reflection terms. Both single-reflection and triple-reflection FFT peaks are presented in FIG. 10. All possible triple-reflection peaks are listed in Table 1. The triple-reflection peaks have low intensity, so, if noise is added to the data, most of the triple-reflection peaks "disappear", as seen in FIG. 11. The only visible triple-reflection FFT peaks are at 391 Hz, 594 Hz, and 686 Hz.

TABLE 1

All Possible Triple-Reflection Peaks for a 5-Interface Sample

| Interface #1 | Interface #2 | Interface #3 | Frequency [Hz] |
|---|---|---|---|
| 2 | 1 | 2 | 391.0 |
| 2 | 1 | 3 | 593.7 |
| 2 | 1 | 4 | 788.1 |
| 2 | 1 | 5 | 855.6 |

TABLE 1-continued

All Possible Triple-Reflection Peaks for a 5-Interface Sample

| Interface #1 | Interface #2 | Interface #3 | Frequency [Hz] |
|---|---|---|---|
| 3 | 1 | 2 | 593.7 |
| 3 | 1 | 3 | 796.4 |
| 3 | 1 | 4 | 990.8 |
| 3 | 1 | 5 | 1058.3 |
| 3 | 2 | 3 | 685.7 |
| 3 | 2 | 4 | 880.0 |
| 3 | 2 | 5 | 947.6 |
| 4 | 1 | 2 | 788.1 |
| 4 | 1 | 3 | 990.8 |
| 4 | 1 | 4 | 1185.1 |
| 4 | 1 | 5 | 1252.7 |
| 4 | 2 | 3 | 880.0 |
| 4 | 2 | 4 | 1074.3 |
| 4 | 2 | 5 | 1141.9 |
| 4 | 3 | 4 | 871.6 |
| 4 | 3 | 5 | 939.2 |
| 5 | 1 | 2 | 855.6 |
| 5 | 1 | 3 | 1058.3 |
| 5 | 1 | 4 | 1252.7 |
| 5 | 1 | 5 | 1320.2 |
| 5 | 2 | 3 | 947.6 |
| 5 | 2 | 4 | 1141.9 |
| 5 | 2 | 5 | 1209.5 |
| 5 | 3 | 4 | 939.2 |
| 5 | 3 | 5 | 1006.8 |
| 5 | 4 | 5 | 812.4 |

Figure 12:
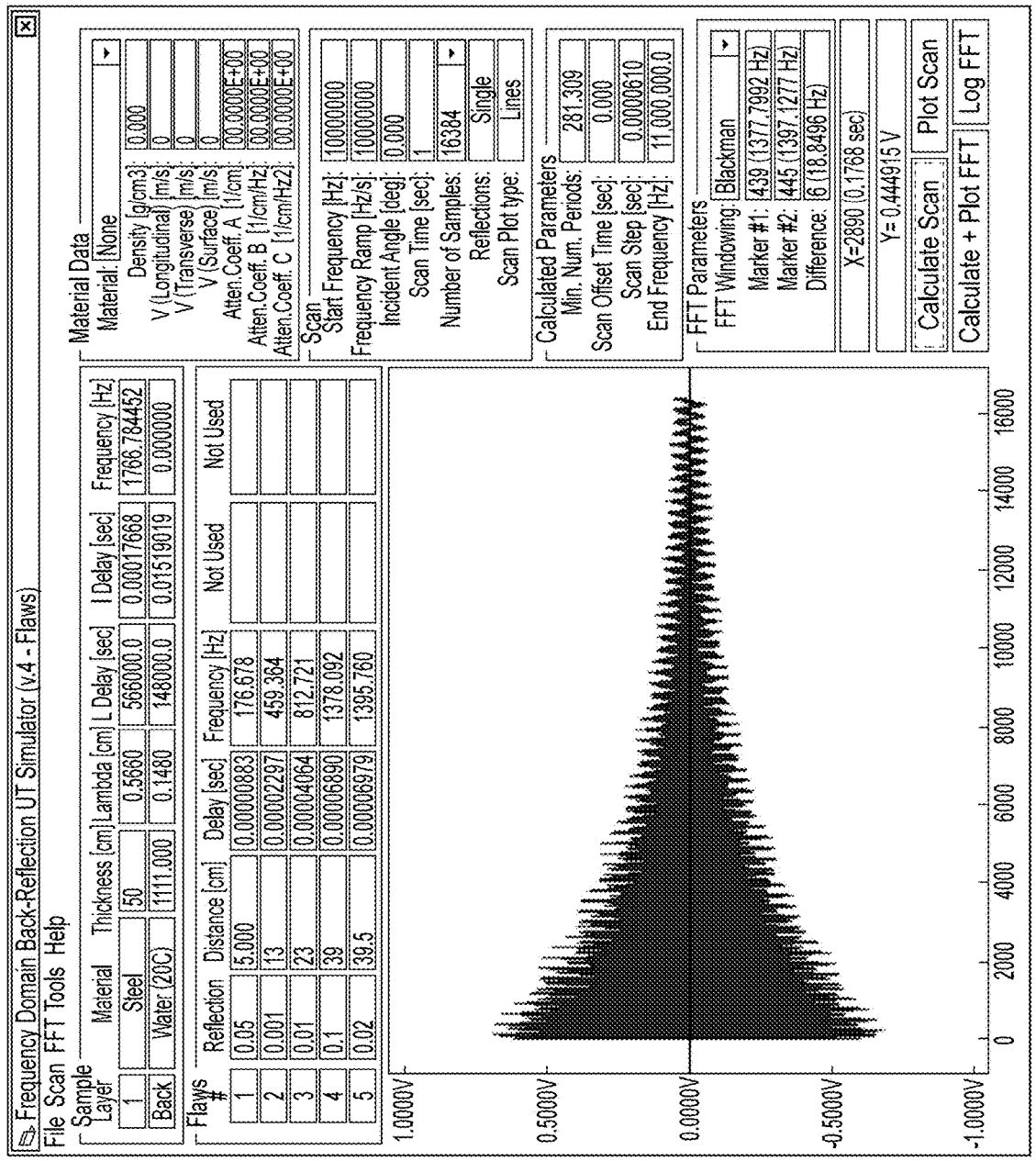
FIG. 12 is a screen capture of a simulated continuous wave frequency modulated ultrasound inspection signal from 5 reflectors inside a single layer.
Figure 13:
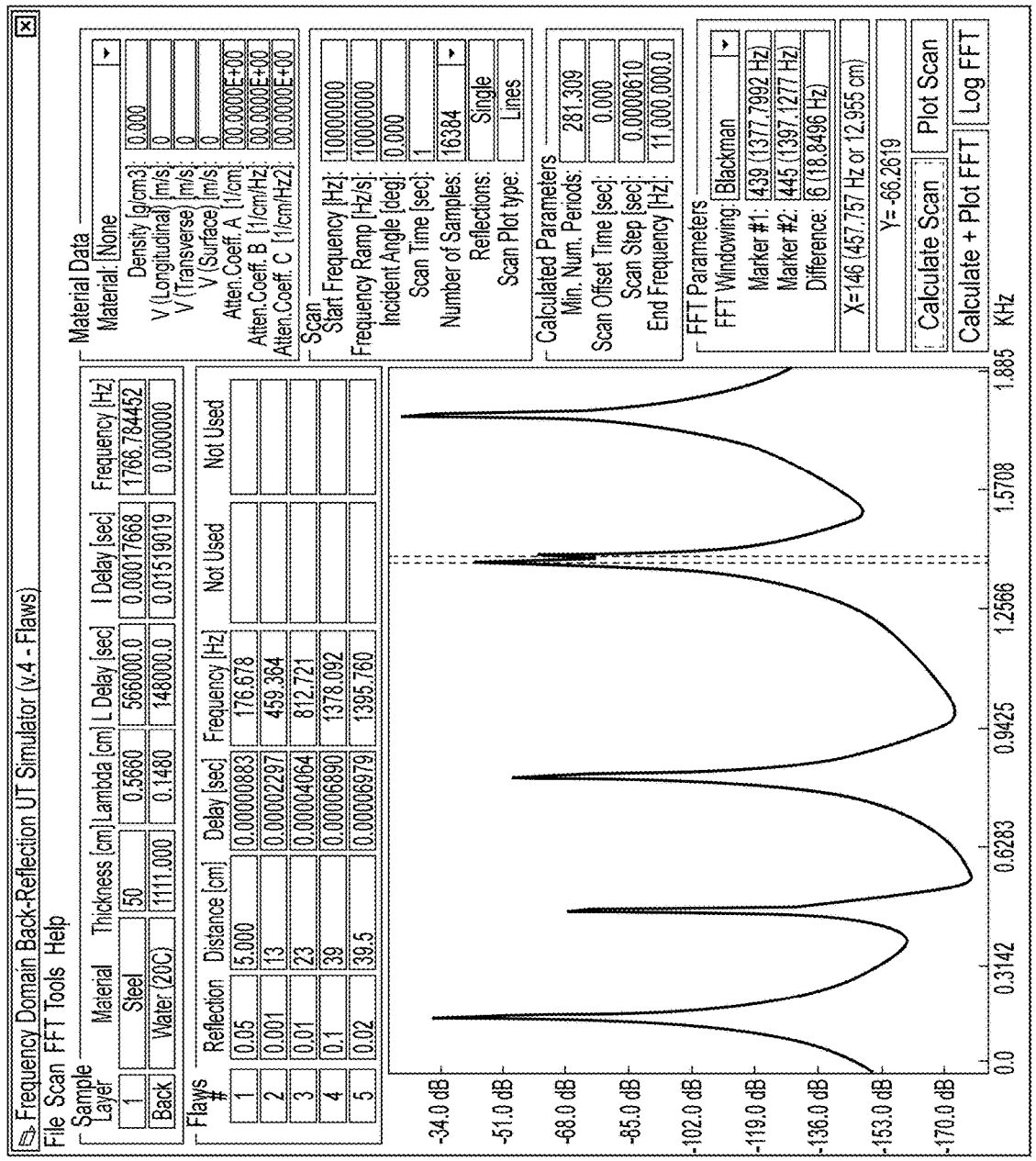
FIG. 13 is a FFT of the data presented in FIG. 12.
Figure 14:
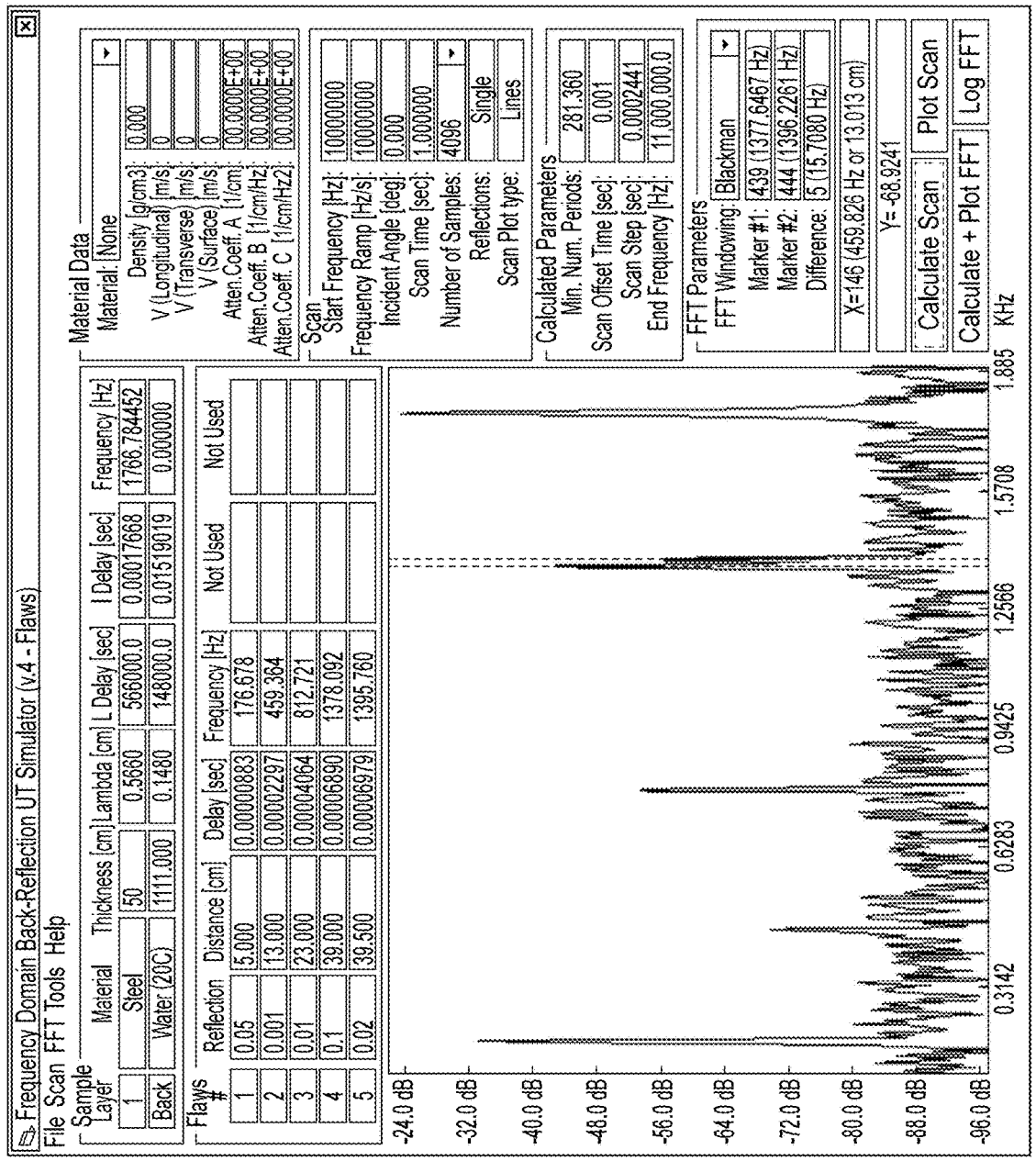
FIG. 14 is a FFT of the data presented in FIG. 12 with added random noise.

The second version of the software was aimed at modeling multiple reflectors (flaws) inside a single layer. Each reflector (flaw 110) was described with distance from the entrance surface and reflection coefficient specifying the fraction of the reflected wave 122 in respect to the forward propagating wave. A screenshot of the program showing the simulated signal from a continuous wave frequency modulated ultrasound inspection system from a 5-reflector sample is presented in FIG. 12. The FFT of the same signal is presented in FIG. 13. As can be seen, the FFT peaks corresponding to each interface are clearly observable. The FFT of the signal shown in FIG. 13, after adding 3% random noise (1% additive and 2% multiplicative) to each measured point, is presented in FIG. 14. Again, the FFT peaks generally corresponding to each reflector/flaw are visible.

In addition to the modelling described herein, it is also possible to evaluate at least some of the possible limits of applicability of the continuous wave frequency modulate ultrasound testing systems and methods described herein. The same assumptions and definitions as described above can be used for the following:

$d_i$ is the distance to flaw "i", [mm].

$v(f)$ is the speed of the sound of frequency f in the test medium, [mm/s].

T is the sound travel time to the closest flaw, $\tau_i = d_i/v(f)$.

Frequency ramp $f(t)=f_0+\Delta f \cdot t$.

$f_0$ is the start frequency of the scan at time t=0, [Hz].

$\Delta f$ is the frequency ramp speed [Hz/sec], $\Delta f=(f_{max}-f_0)/t_{max}$.

$f_{max}$ is the end frequency at the end of the ramp time $t_{max}$.

$t_{max}$ is the frequency ramp time: $t_{max}=(f_{max}-f_0)/\Delta f$.

Frequency of the low-pass filtered signal for the flaw 110 "i":

$$f_R = f(t) - f(t - 2 \cdot \tau_i) = 2 \cdot \tau_i \cdot \Delta f = 2 \cdot \frac{d_i}{v} \cdot \Delta f \quad (21)$$

Period of the low-pass filtered signal:

$$T_R = \frac{1}{f_R} = \frac{1}{f(t) - f(t - 2 \cdot \tau_i)} = \frac{1}{2 \cdot \tau_i \cdot \Delta f} = \frac{v}{2 \cdot d_i \cdot \Delta f} \quad (22)$$

Where:

Number of Scan Points: N

Scan Sampling Interval: $\Delta t_S$ and

Total Scan Time: $t_S = N \cdot \Delta t_S$

It can be assumed that the total scan time is equal to the total ramp time, i.e.:

$$t_S = t_{max}, \text{ or } N \cdot \Delta t_S = \frac{f_{max} - f_0}{\Delta f} \quad (23)$$

The total ramp time may be longer than the time for the signal 120 to travel to flaw 110 "i" and back, and there may be an overlap between the generated and reflected signals 120, 122 which may correspond to at least two periods of the low-pass signal for flaw 110 "i". Performing a FFT on the signal:

$$t_S = t_{max} > 2 \cdot \tau_i + 2 \cdot T_R = 2 \cdot \tau_i + \frac{1}{\tau_i \cdot \Delta f} \quad (24)$$

From here we get the following quadratic function for $\tau_i$ $$-2 \cdot \Delta f \cdot \tau_i^2 + t_{max} \cdot \Delta f \cdot \tau_i - 1 > 0 \quad (25)$$

This function has a maximum at:

$$(\tau_i)_{max} = \frac{t_{max}}{4} \quad (26)$$

For the maximum to be positive, the following condition must be satisfied:

$$(f_{max} - f_0) > 2\sqrt{2 \cdot \Delta f} \quad (27)$$

After combining Equations 23 and 27, the limiting condition for the linear frequency ramp can be defined as:

$$(f_{max} - f_0) > 2\sqrt{2 \cdot \Delta f}, \text{ or } t_{max} > 2\sqrt{\frac{2}{\Delta f}}, \text{ or } \Delta f < \frac{(f_{max} - f_0)^2}{8} \quad (28)$$

The values at which the left part of Equation 25 becomes equal to zero are:

$$(\tau_i)_{1/2} = \frac{t_{max}}{4}\left(1 \pm \sqrt{1 - \frac{8}{t_{max}^2 \cdot \Delta f}}\right)$$

Therefore, to have the total ramp time longer than the time for the sound waves 120 to travel to the closest flaw 110 and back plus at least two periods of the low-pass signal, z can be between the values $(\tau_i)_1$ and $(\tau_i)_2$.

$$\frac{t_{max}}{4}\left(1 - \sqrt{1 - \frac{8}{t_{max}^2 \cdot \Delta f}}\right) \leq \tau_i \leq \frac{t_{max}}{4}\left(1 + \sqrt{1 - \frac{8}{t_{max}^2 \cdot \Delta f}}\right), \text{ or} \quad (29)$$

$$\frac{t_{max}}{4}\left(1 - \sqrt{1 - \frac{8}{t_{max}^2 \cdot \Delta f}}\right) \leq \frac{d_i}{v} \leq \frac{t_{max}}{4}\left(1 + \sqrt{1 - \frac{8}{t_{max}^2 \cdot \Delta f}}\right)$$

This can enable derivation of a limiting condition for the minimum distance to the flaw 110 (assuming fixed the values for $(f_{max}-f_0)$ and $\Delta f$):

$$(d_i)_{min} \geq v \cdot \frac{(f_{max} - f_0)}{4 \cdot \Delta f} \cdot \left(1 - \sqrt{1 - \frac{8 \cdot \Delta f}{(f_{max} - f_0)^2}}\right) \quad (30)$$

It may not be preferable to use the same derivation to get a limiting condition for the maximum distance to the flaw, because in the general case, the total ramp time can be equal to the time for the sound wave 120 to travel to the flaw 110 and back plus "n" periods of the low-pass signal, where "n" can be any number bigger than 2.

Figure 15:
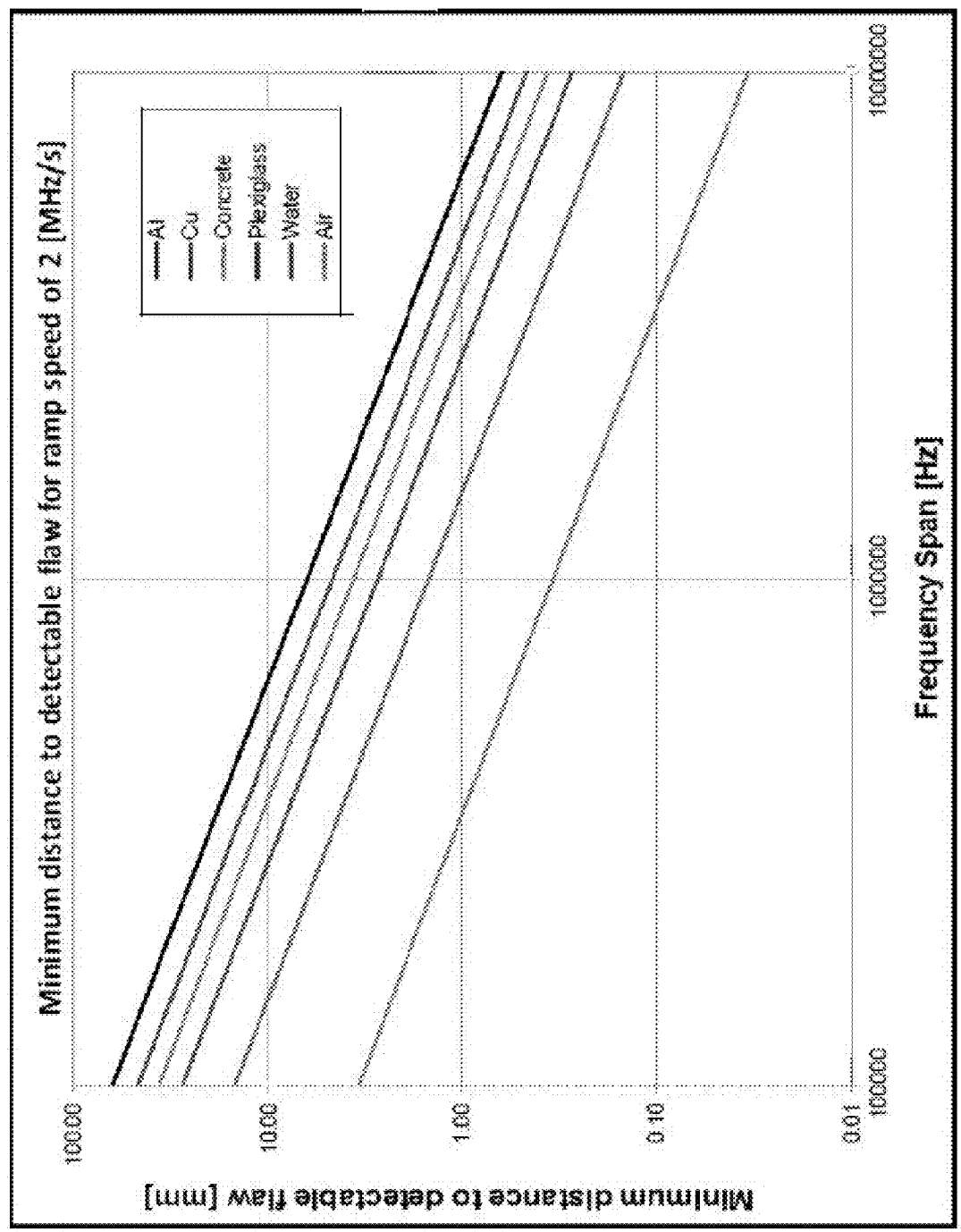
FIGS. 15 and 16 are plots showing the dependence of the minimum distance to the flaw on the frequency span and on the frequency ramp speed.
Figure 16:
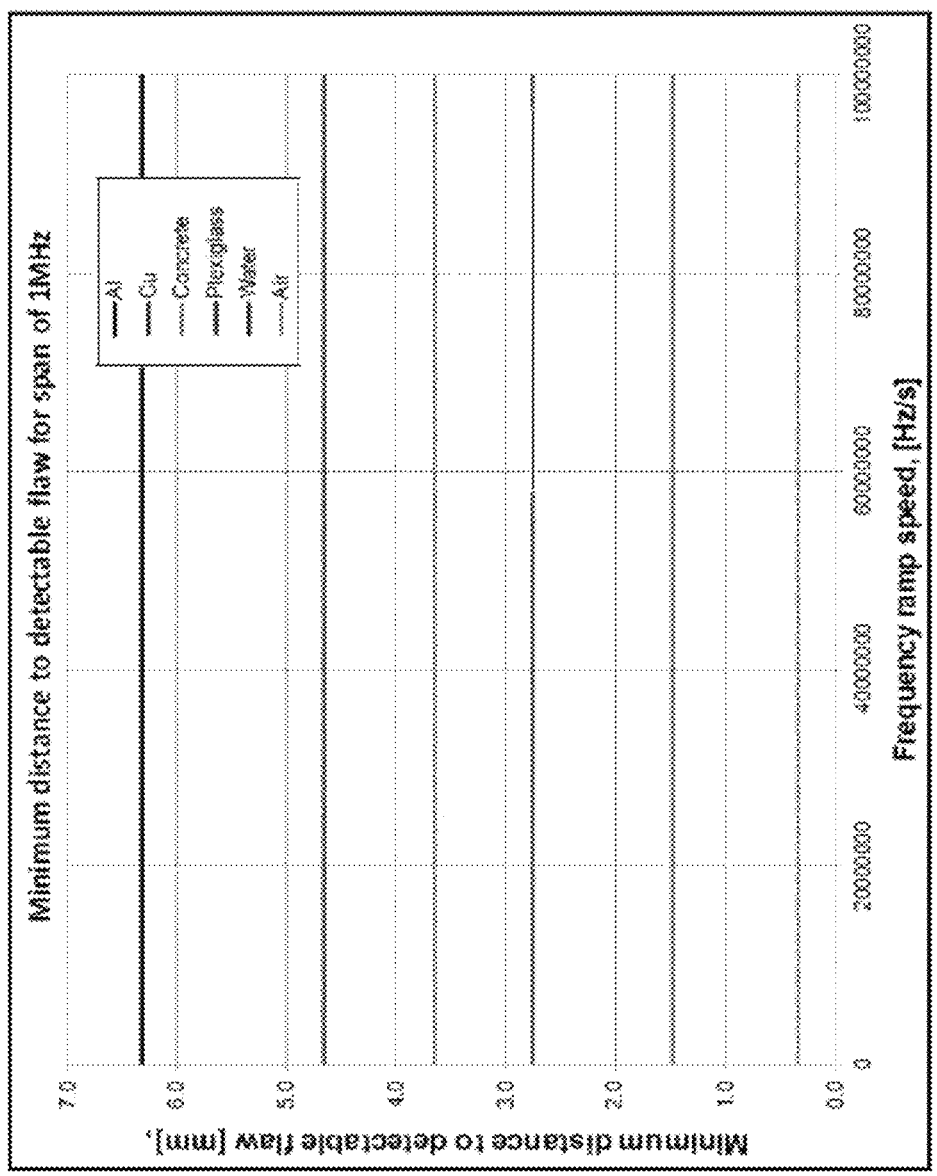

Dependence of the minimum distance to the flaw on the frequency ramp span $(f_{max}-f_0)$ (for frequency ramp speed $\Delta f$ fixed to 2 [MHz/s]) and on the frequency ramp speed $\Delta f$ (for frequency ramp span $(f_{max}-f_0)$ fixed to 1 [MHz]) is presented in FIGS. 15 and 16. In these examples, the minimum distance depends on frequency ramp span $(f_{max}-f_0)$, but does not practically depend on frequency ramp speed $\Delta f$.

Figure 17:
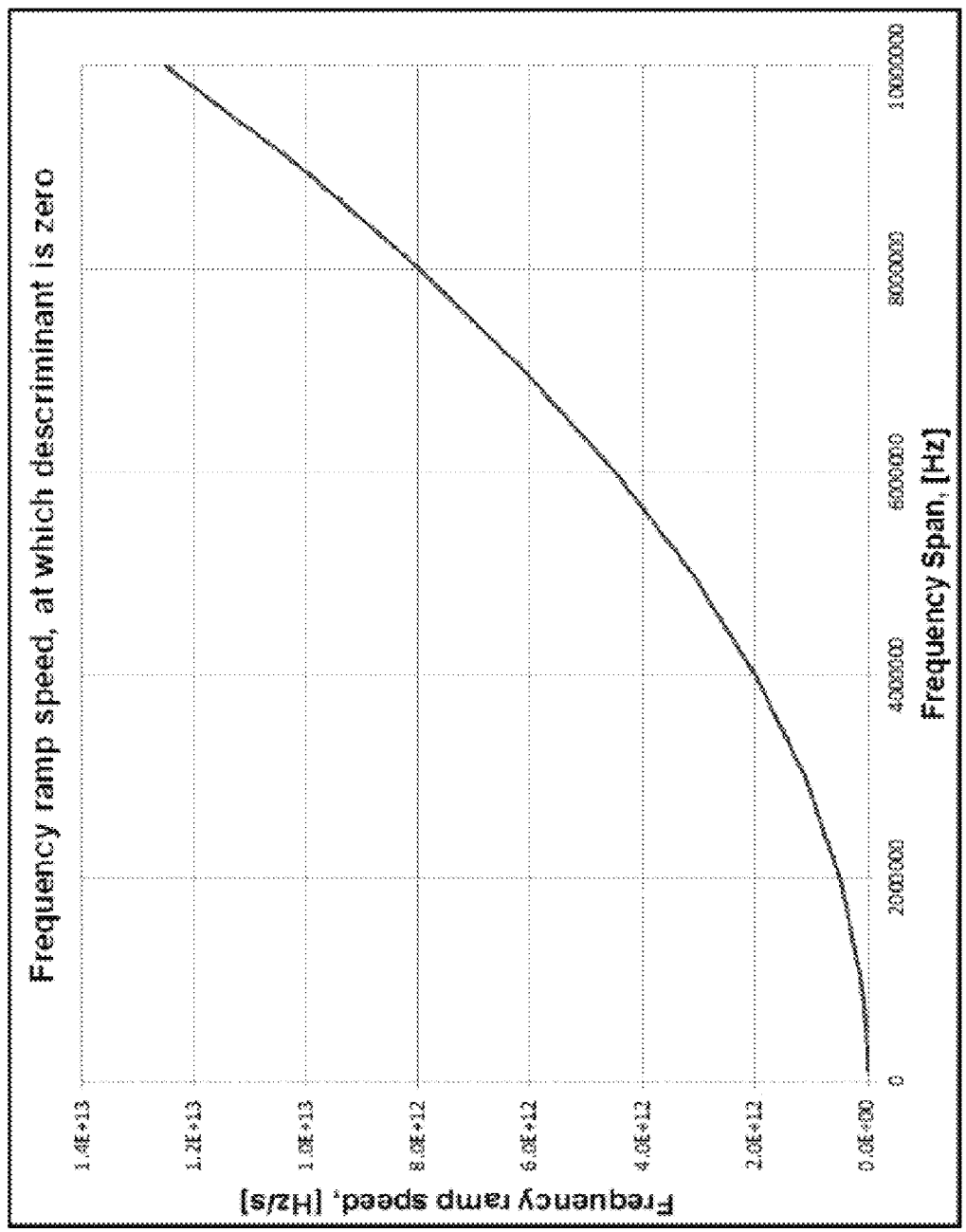
FIG. 17 is a plot showing the applicability region of one example of a continuous wave frequency modulated ultrasound inspection method.

The applicability region of the continuous wave frequency modulation ultrasound inspection system and method as defined by Equation 27 is presented in FIG. 17. In this example, the area below the curve specifies the desirable combinations of frequency ramp speed $\Delta f$ and frequency ramp span $(f_{max}-f_0)$. The usable frequency spans (i.e. the region where the signal is above 10% from the maximum signal) for some examples of typical ultrasonic transducers (such as transmitter 104 and receiver 108) are presented in Table 2.

TABLE 2

Usable Frequency Spans for Typical UT Transducers

| Transducer Center Frequency, [MHz] | Usable Frequency Span [MHz] |
|---|---|
| 0.05 | 0.18 |
| 0.5 | 0.85 |
| 0.1 | 0.27 |
| 1 | 1.3 |
| 2 | 2.5 |
| 5 | 7.7 |
| 10 | 13 |

Usually, the frequency ramp speed $\Delta f$ is of the same order of magnitude as the frequency ramp span $(f_{max}-f_0)$, so Equation 30 can be simplified and an approximate formula for the limiting condition for the minimum distance to the closest flaw $d_i$ can be derived:

$$(d_i)_{min} \geq \frac{v}{(f_{max} - f_0)} \quad (31)$$

In these examples, the minimum distance may depend on frequency ramp span $(f_{max}-f_0)$, but does not depend on frequency ramp speed $\Delta f$. The above simplification is also based on the fact that in most cases the time for the sound to travel to the closest flaw 110 is shorter than the total scan time (i.e., $\tau_i \ll T_R$). In this case, Equation (24) can be simplified to:

$$t_S = t_{max} > 2 \cdot T_R \quad (32)$$

Applying Equation (22), leads to Equation (31). Equation (31) can be written also as a condition for the minimum required frequency span of the frequency ramp:

$$(f_{max} - f_0) > \frac{1}{\tau_i} = \frac{v}{d_i} \quad (33)$$

Figure 18:
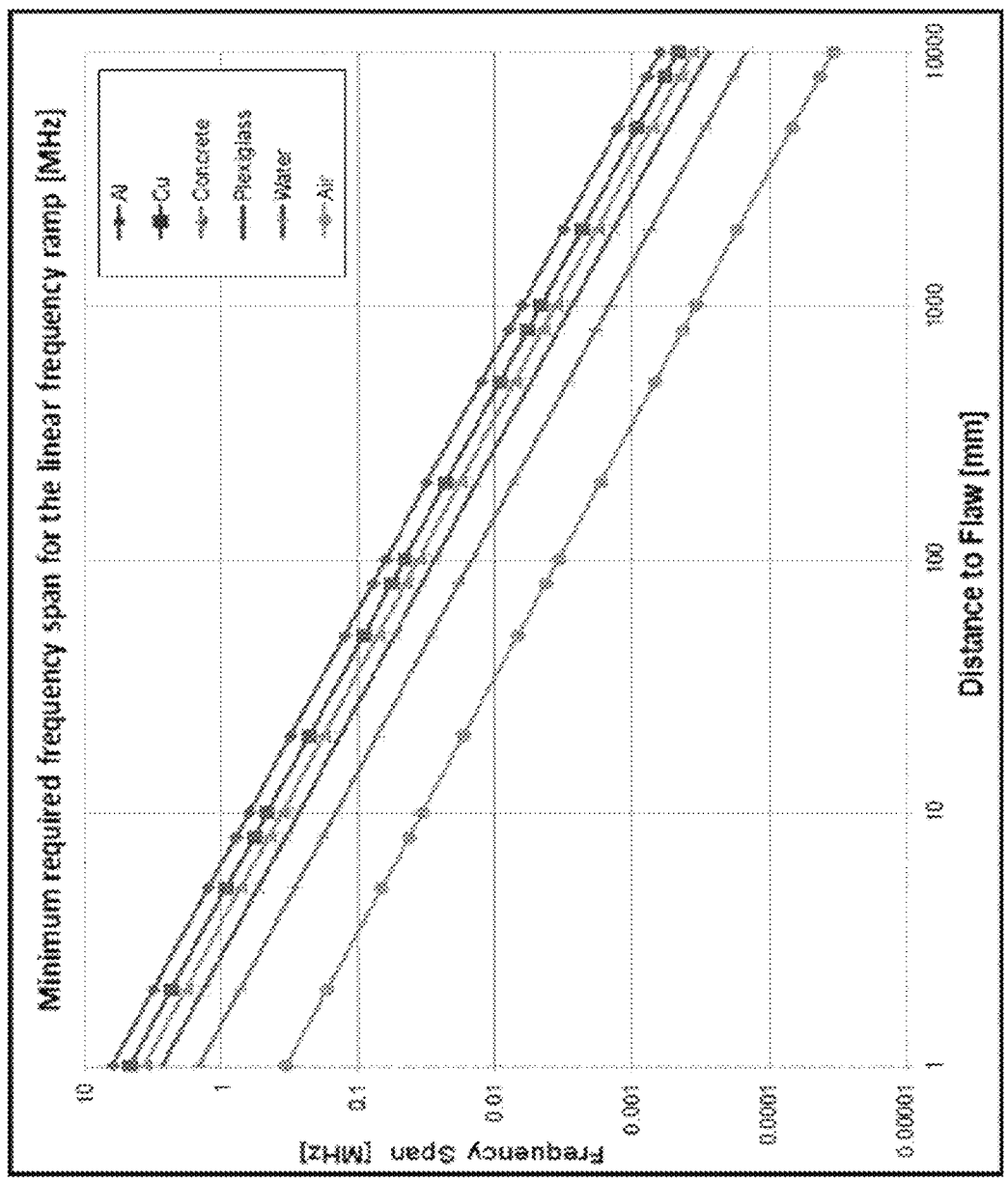
FIG. 18 is a plot showing a minimum frequency span as a function of the distance to a flaw for one example of a continuous wave frequency modulated ultrasound inspection system.

The required minimum frequency span as a function of the distance to the flaw for different materials is presented in FIG. 18.

As can be seen, the minimum distance to the flaw 110 is proportional to the speed of the sound in the material of the object 106. Because of that, one can achieve best minimum distance (or resolution) in air, and the minimum distance to flaw in water may be several times smaller than that in aluminium for one and the same conditions.

The next step may be to account for the properties of the FFT and how it influences the resolution of the continuous wave frequency modulated ultrasound inspection method. The maximum sampling frequency is $F_S$:

$$F_S = \frac{N}{t_S} = \frac{1}{\Delta t_S} \quad (34)$$

The maximum measurable (resolvable) frequency (Nyquist frequency) is FN:

$$F_N = \frac{F_S}{2} = \frac{1}{2 \cdot \Delta t_S} \quad (35)$$

The frequency of the low-pass filtered signal $f_R$ should be smaller than the Nyquist frequency FN, but close to the Nyquist frequency, for example 9/10 of Nyquist frequency (this will correspond to a maximum distance to the detectable flaw):

$$f_R = f(t) - f(t - 2 \cdot \tau_i) = 2 \cdot \tau_i \cdot \Delta f = 2 \cdot \frac{d_i^{max}}{v} \cdot \Delta f \quad (36)$$

$$f_R = \frac{3}{4} F_N = \frac{3}{4} \cdot \frac{N}{t_S} \quad (37)$$

By combining Equations (36) and (37), an equation for the maximum distance to a detectable flaw 110 can be derived where:

$$(d_i)_{max} = \frac{9}{20} \cdot \frac{v \cdot N}{\Delta f \cdot t_S} = \frac{9}{20} \cdot \frac{v}{\Delta f \cdot \Delta t_S} = \frac{9}{20} \cdot N \cdot (d_i)_{min} \quad (38)$$

To resolve two frequencies $f_1$ and $f_2$, a frequency resolution of at least $|f_1-f_2|/6$ for the low-frequency region can be used, and $|f_1-f_2|/12$ for the high-frequency region. The maximum achievable frequency resolution can be $\Delta F$ where:

$$\Delta F = \frac{F_S}{N} = \frac{1}{t_S} = \frac{1}{N \cdot \Delta t_S} \quad (39)$$

Which can lead to the following condition:

$$\Delta F = \frac{|f_1 - f_2|}{12} \text{ or } \left| \frac{2 \cdot \Delta f \cdot d_1}{v} - \frac{2 \cdot \Delta f \cdot d_2}{v} \right| = \frac{12}{t_S} \quad (40)$$

From here, one can derive an equation for the minimum distance resolution (based on Equations 23, 31, 39, and 40), where:

$$\delta d = |d_1 - d_2| = 6 \cdot \frac{v}{t_S \cdot \Delta f} = 6 \cdot \frac{v}{N \cdot \Delta t_S \cdot \Delta f} = 6 \cdot \frac{v}{(f_{max} - f_0)} = 6 \cdot (d_i)_{min} \quad (41)$$

Equations 31, 38, and 41 can define the minimum distance, the maximum distance, and the distance resolution for at least some embodiments of the systems and methods described herein. As can be seen, these parameters may depend only on the speed of sound v, on the frequency ramp span ($f_{max}-f_0$), and on the number of scan points for the measurements N. The relative resolution at maximum distance does not depend on the material and frequency ramp span, but only on the number of scan points N, and is given by Equation (42) and is presented in Table 3:

$$\frac{\delta d}{(d_i)_{max}} [\%] = 100 \cdot \frac{|d_1 - d_2|}{(d_i)_{max}} = 100 \cdot \frac{40}{3} \cdot \frac{1}{N} \quad (42)$$

TABLE 3

| Number of scan points N | Relative resolution in [%] |
|---|---|
| 1024 | 1.30 |
| 4096 | 0.33 |
| 16384 | 0.08 |
| 32768 | 0.04 |

Figure 19:
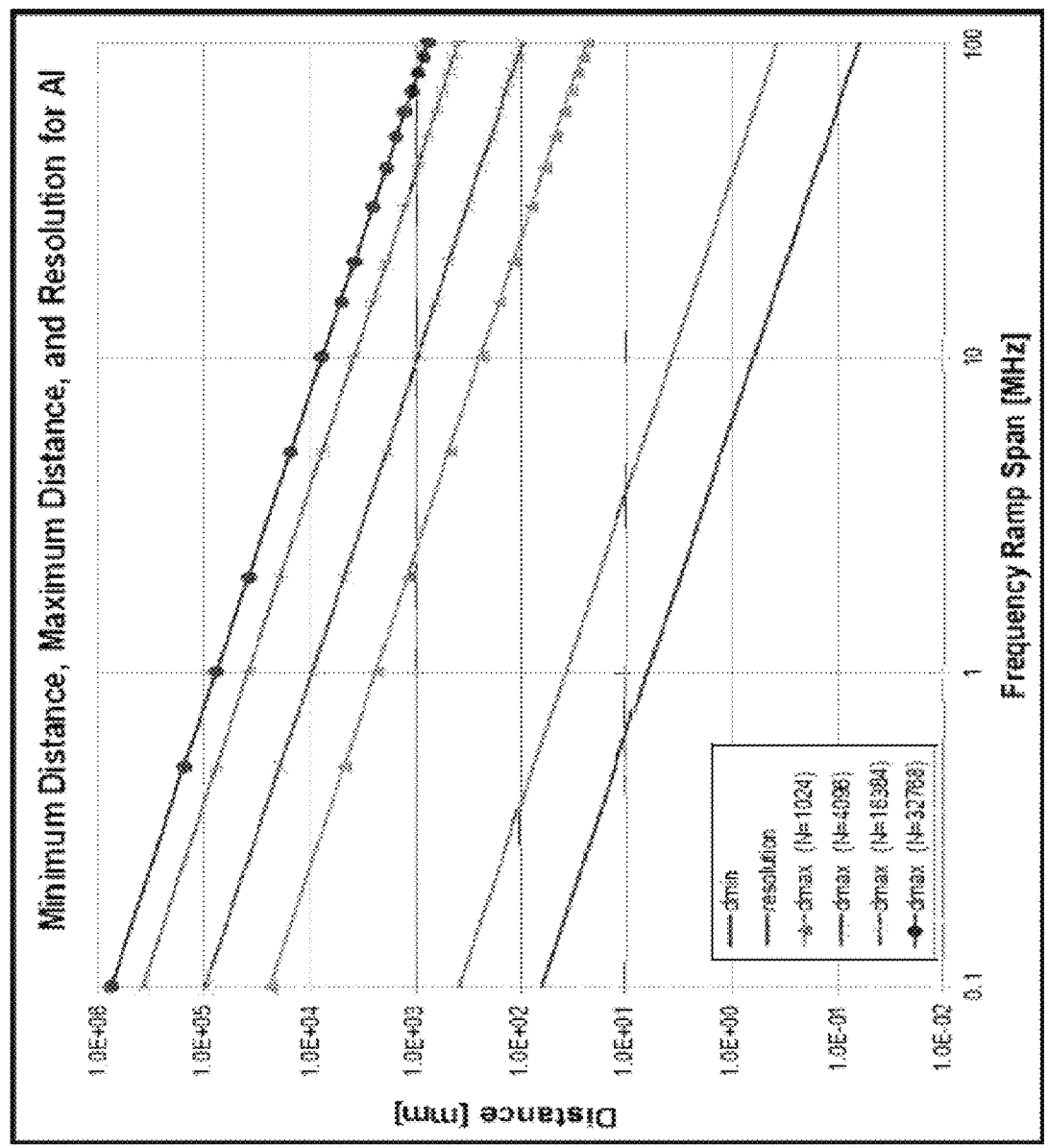
FIG. 19 is a plot showing the minimum distance, maximum distance and resolution for Aluminium used in combination with one example of a continuous wave frequency modulated ultrasound inspection system.
Figure 20:
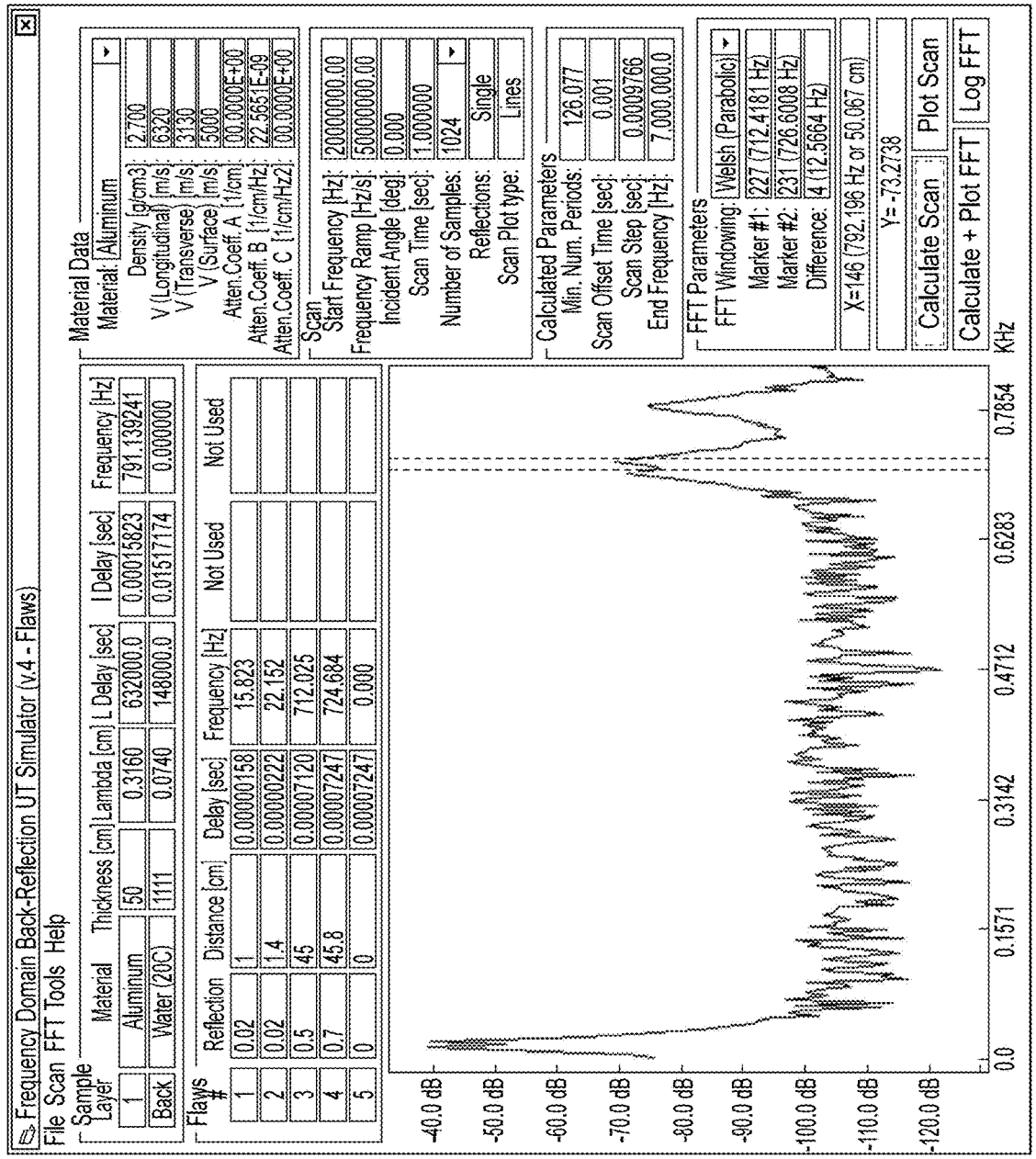
FIG. 20 is a screen capture showing data related to the modelling of the calcualted parameters of Table 4, with noise added to the calculated signal.

The dependence of the minimum distance, the maximum distance, and the resolution on the frequency ramp span ($f_{max}-f_0$) for different number of scan points N is shown for Al in FIG. 19. Computer modeling was used to confirm the derived equations for the limitations of the methods described herein. Parameters used for calculations are presented in Table 4. FFT of the calculated signal with noise added is shown in FIG. 20. As can be seen, this method may be able to help resolve flaws separated by 4 mm in the region of small distances and may be able to resolve flaws separated by 8 mm in the region of large distances.

Modeling generally confirmed that the methods and systems described herein may resolve distances which are separated by 3"dmin in the low-frequency region (the peaks at 15 and 23 Hz correspond to flaws at distances of 10 and 14 mm, and as per Table 4, dmin=1.2 mm), and also we can resolve distances which are separated by 6*dmin in the high-frequency region (the peaks at 712 and 726 Hz correspond to flaws at distances of 450 and 458 mm). The last peak at 791 Hz corresponds to the end of the Aluminum (Al) rod (Al-Water interface reflection).

TABLE 4

Calculated Parameters for Al

| | Value for Al |
|---|---|
| Input Parameters | |
| v [mm/s] | 6320000 |
| span ($f_{max}-f_0$) [MHz] | 5 |
| ramp speed $\Delta f$ [MHz/s] | 5 |
| ramp time $t_{max}$ [sec] | 1 |
| scan points N | 1024 |
| scan time $t_s$ [sec] | 1 |
| sampling interval $\Delta t_s$ [sec] | 0.0009766 |
| Calculated Parameters | |
| $d_{min}$ [mm] | 1.3 |
| $d_{max}$ [mm] | 485.4 |
| resolution $\delta d$ [mm] | 7.6 |

In addition to the modelling described above, additional experiments were conducted using the system of FIG. 21. These experiments were conducted with the 5 MHz dual transducer (Olympus model D7075). The frequency span was from 1 MHz to 10 MHZ, and the frequency ramp speed was usually fixed to 10 MHz/s.

Figure 22:
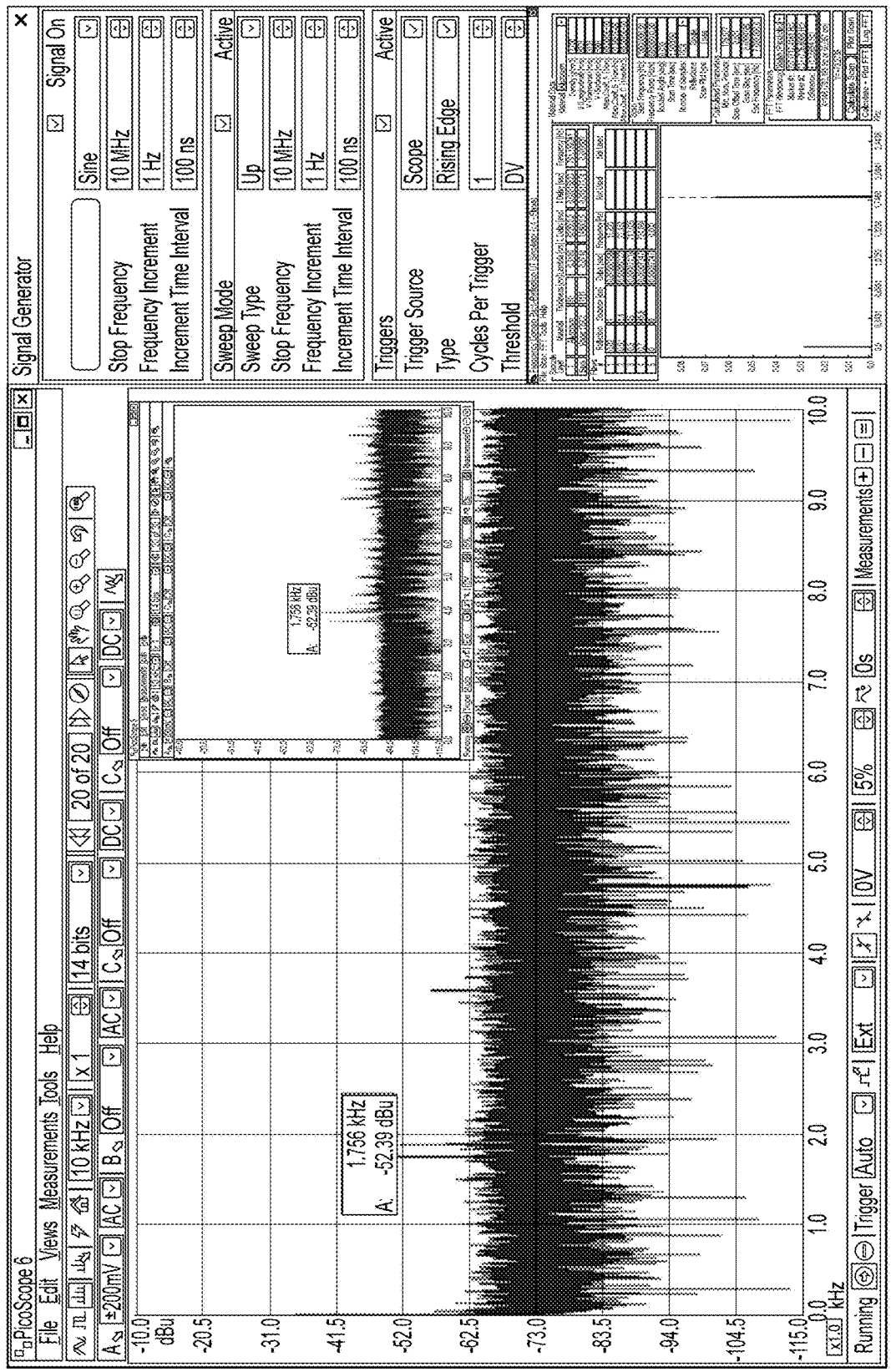
FIG. 22 is a representation of a measurement of a 505 mm steel rod using one example of a continuous wave frequency modulated ultrasound inspection system.

A first example is of a 505 mm steel cylindrical rod, measured with a 5 MHz dual transducer (Olympus model D7075). Computer modeling using software described herein predicted a frequency for the reflection from the back-wall of 1784 Hz. The measured frequency of the peak corresponding to the back-wall reflection was 1756 Hz, which is within the expected deviation due to differences in the speed of sound in different types of steel. The results are presented in FIG. 22. The insert in the bottom right corner shows the results of modeling. The insert in the top right corner shows the settings for the signal generator, and the insert to the left shows the results when the frequency ramp speed is doubled from 10 MHz/s to 20 MHz/s (the frequency of the reflection peak doubles). In FIG. 22, there is a second peak at around 1880 Hz, which has smaller amplitude. This peak may generally correspond to reflection of a different propagation mode inside the cylindrical rod, with a lower speed of sound. Also, the peak corresponding to double reflection (at around 3520 Hz) is visible.

Figure 23:
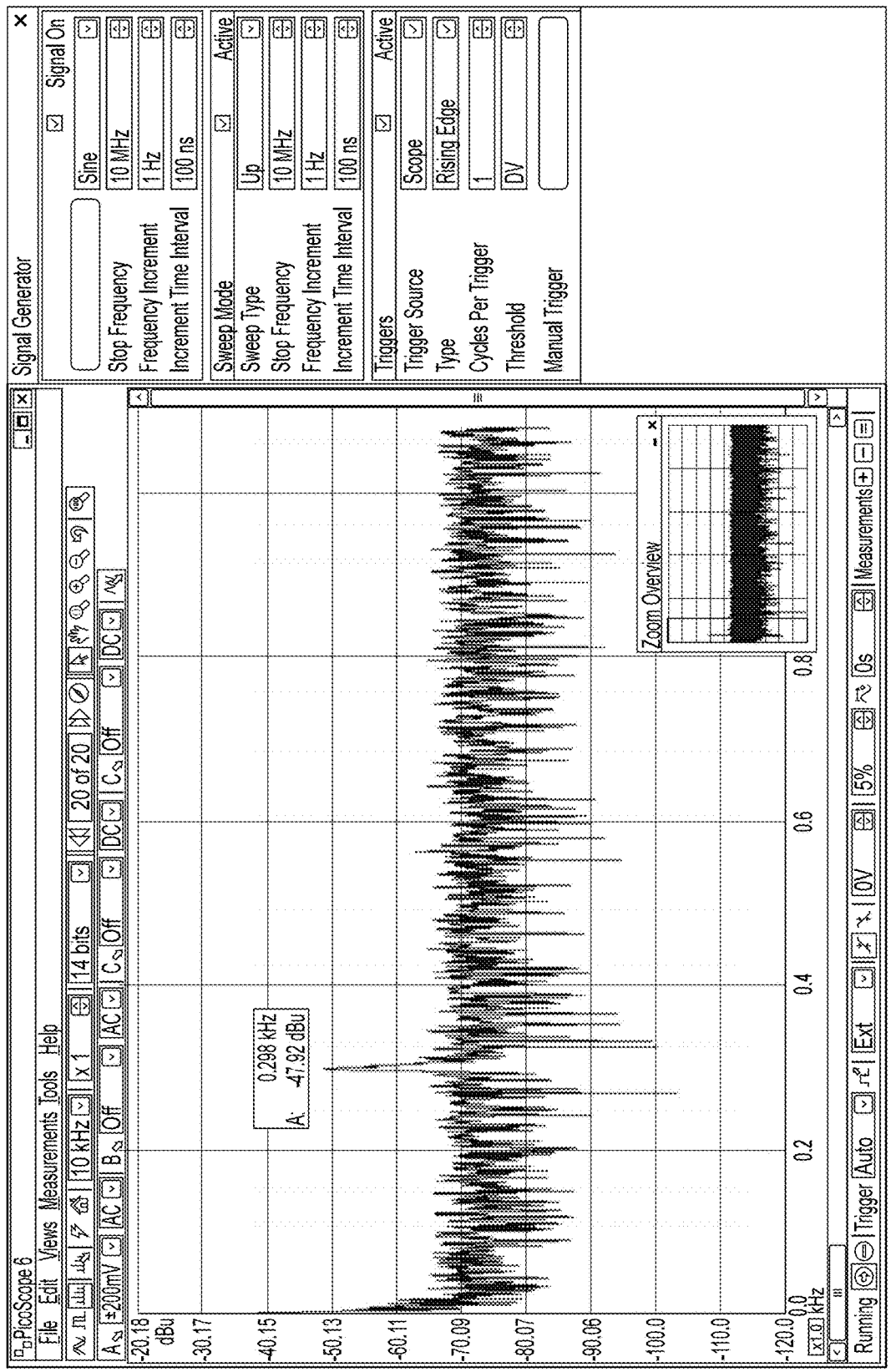
FIG. 23 is a representation of a measurement of a 35 mm polystyrene sample using one example of a continuous wave frequency modulated ultrasound inspection system.

The next measurement was of a 35 mm Polystyrene sample, see FIG. 23. The computer modeling predicted frequency for the back-wall reflection peak at 299 Hz, while the measured peak was at 298 Hz. The peak from the second reflection is very close to the noise level (almost unobservable).

Figure 24:
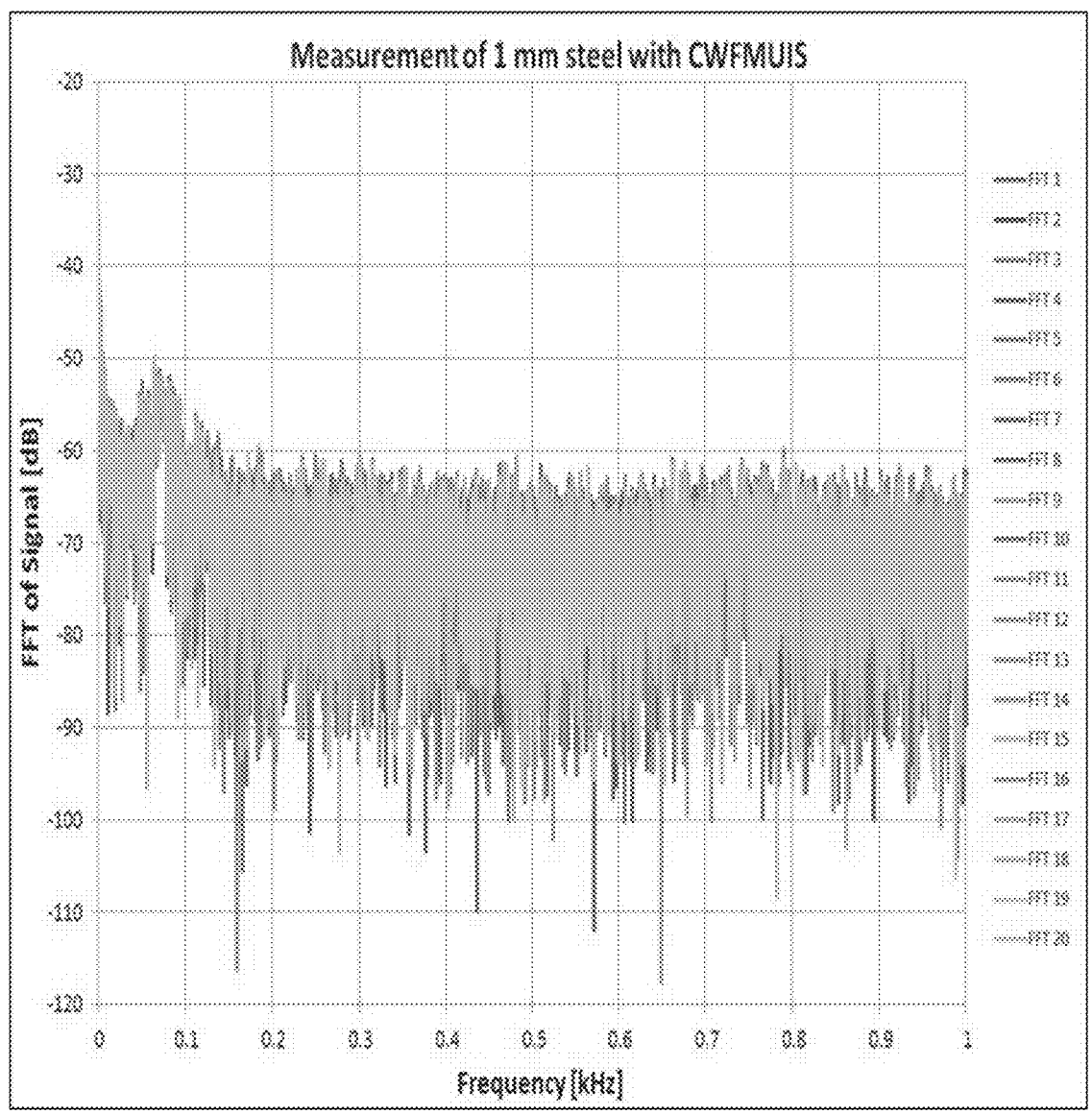
FIG. 24 is plot showing measurements of a 1 mm steel plate using one example of a continuous wave frequency modulated ultrasound inspection system.
Figure 25:
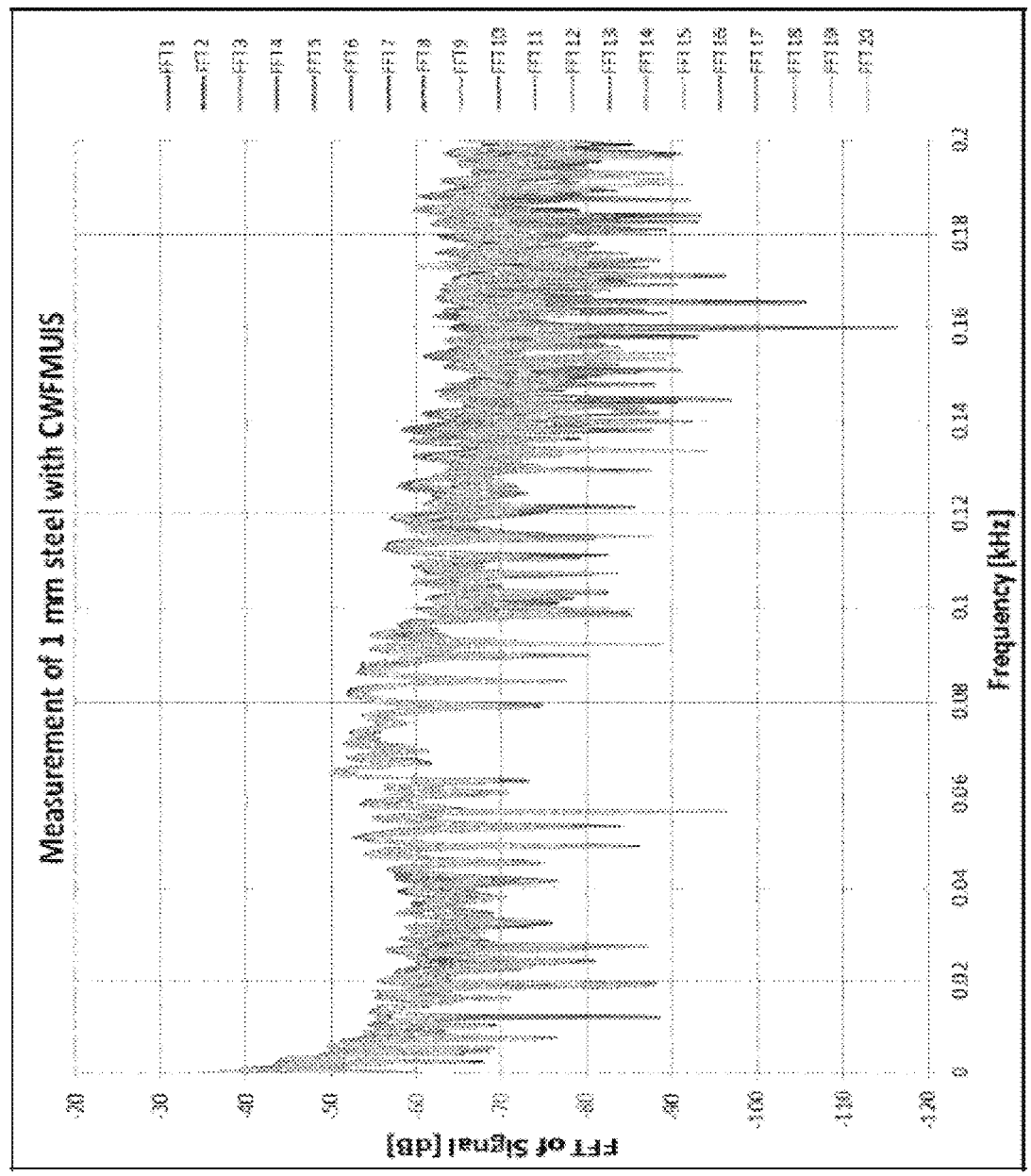
FIG. 25 is an enlarged view of a portion of the plot of FIG. 24.

The next measurement was an attempt to measure the thickness of a 1 mm Steel plate (the actual thickness was 0.92 mm). The computer modeling predicted frequency for the back-wall reflection peak at 3.5 Hz, which is a relatively low frequency, i.e., there are less than three periods of the wave within the 0.9 s scan time. The measurement results (20 overlaid FFT traces) are presented in FIG. 24. As can be seen, no peak is visible at 3.5 Hz, but there is a repeatable signal in the region from 40 to 100 Hz (in the other parts of the scans, one can clearly observe the random character of the FFT traces, which can be associated with random noise); see FIG. 25.

Figure 26:
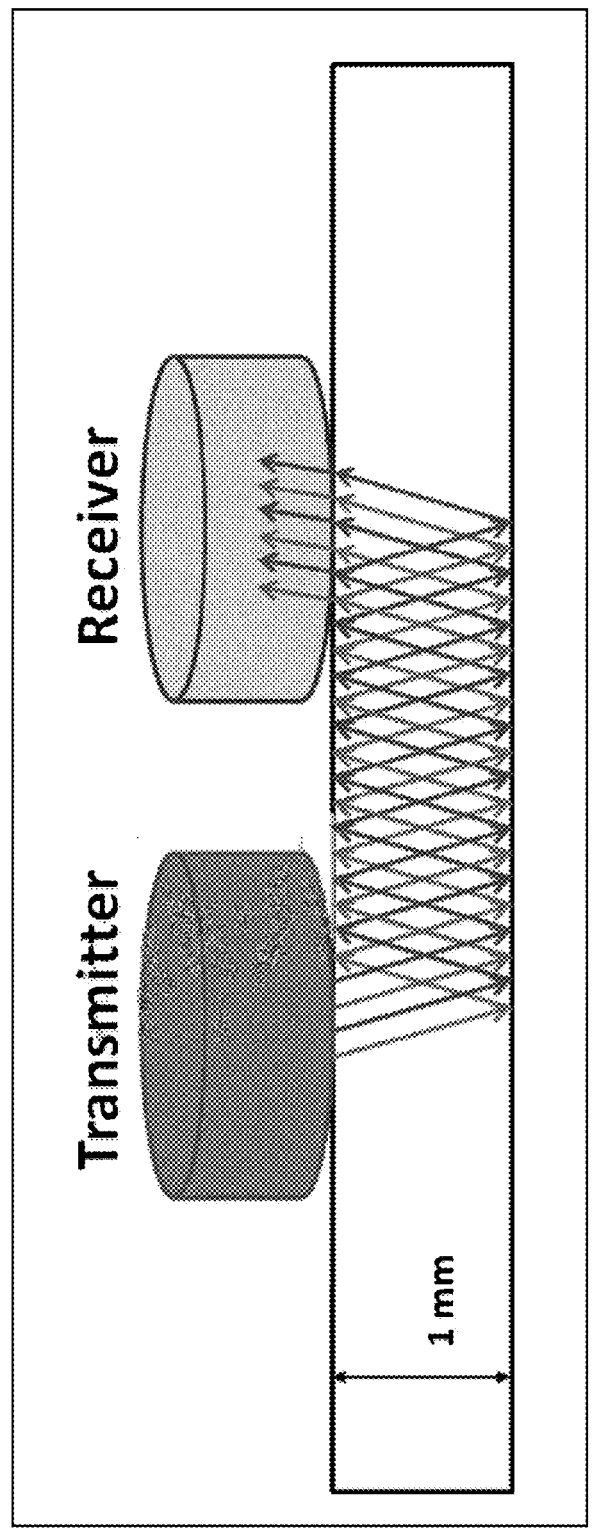
FIG. 26 is a schematic representation of multiple ultrasound beam reflections in a thin plate.

The observed type of signal may be explained by the fact that the transmitter and receiver are separated (in this case the distance center-to-center was 6 mm), and the UT beam is perpendicular to the surface with some small beam divergence, the UT beam will experience multiple reflections before traveling from the transmitter to the receiver, see FIG. 26. In this example, there are 17 peaks in the region from 40 to 100 Hz, which corresponds to average distance between peaks of 3.52 Hz, which agrees very well with the results from the modeling. If the center-to-center travel corresponds to about the center of the signal region (i.e., 70 Hz), then 20 reflections of the UT beam from the center of the transmitter to the center of the receiver may be created. This effective increase of the thickness of the sample explains why we can measure thickness which is smaller than the minimum measurable distance as defined with Equation 31. The same approach can be used with the pulse-based (time of flight) UT method, using a separate transmitter and receiver. From the 6 mm center-to-center distance and 20 reflections (corresponding to 20 mm effective thickness), one can derive that the deviation angle of the UT beam from the vertical is 16 degree, or the travel path of the beam during each reflection will be 1.04 times longer than the thickness of the plate. One may also account for the small offset between the crystal and the face-plate of the transducer.

Another way to measure a thin plate is to use transducers with built-in delay-line, which may shift the measurements toward the higher frequencies. Yet another way to measure small thicknesses may be to use additional hardware to multiplex the low-frequency signal after the low-pass filter ($V_{LPF}(t)$) with a pre-defined single-frequency sinusoidal wave, which again will shift the final signal toward the higher frequencies region. Another way to resolve very low-frequency FFT peaks may be to use zoom-FFT mathematical signal processing.

Figure 28:
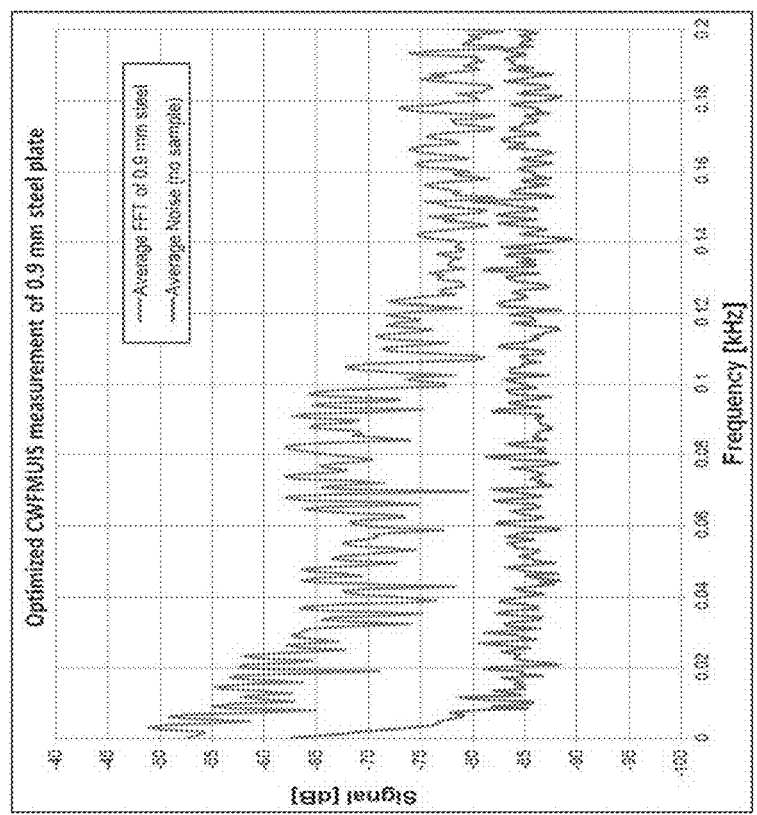
FIG. 28 is a plot showing measurements of a 0.9 mm steel plate using one example of a continuous wave frequency modulated ultrasound inspection system (average of 20 FFT scans)
Figure 27:
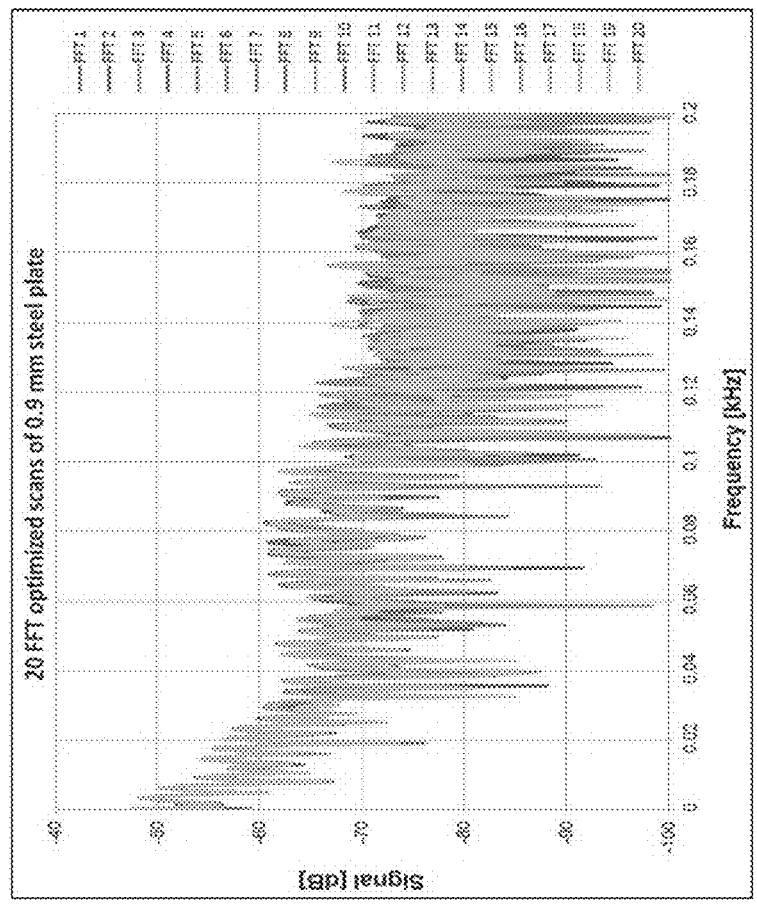
FIG. 27 is a plot showing measurements of a 0.9 mm steel plate using one example of a continuous wave frequency modulated ultrasound inspection system (20 FFT scans)

As measuring small thicknesses may be desirable in some embodiments of the systems and methods described herein, experiments were performed for this case specifically. The measurement setup was configured to produce relatively strong UT signals, and precautions were taken to reduce electronic noise. Results are shown in FIGS. 27 and 28 (average signal over 20 FFT scans). In this example, there are repeatable FFT peaks above noise in the region from 0 to 104 Hz (30 peaks, 3.47 Hz spacing, FFT step is 0.6 Hz), and even the first FFT peak at 3.1 Hz is observable.

In addition to the experiments described herein, modeling the influence of dispersion in waveguides on the frequency sweep curve was conducted.

Experiments were also conducted in which the mechanical waves introduced to the object were guided waves. While bulk body waves tend to propagate inside the body of a medium and are only bound to satisfy the constitutive equation, guided waves also satisfy its boundary conditions. As a result, the type of guided waves that can be generated in solid media may depend on the geometry of the structure in which they take shape. As compared to bulk body waves that consist of individual waves, guided waves may be made of packets of waves, which propagate at a velocity different from the phase velocity of the individual components. The superimposition of individual waves of similar frequency results in some sort of signal "beating" where the individual elements travel at their phase velocity while the wave packets travel at the group velocity. That is, phase velocity specifies the speed at which any fixed phase of the cycle is displaced, while the group velocity specifies the speed at which the overall shape of the wave amplitude (known as the modulation or envelope of the wave, or a wave packet) propagates through space. Hence, from a UT point of view, group velocity is the velocity of primary interest since the transducers can sense the perturbation of the group of waves as a whole.

Guided waves can be subcategorized into propagation modes, characterized by patterns of displacement field distribution in the medium of propagation. Because guided waves satisfy the structure boundary conditions, the physics of the wave propagation is such that their speed may be generally frequency-dependent. This feature, known as dispersion, can be used for mode selection. Each mode is characterized by a curve relating its wave speed to frequency. A given mode can be excited by acting at a specific point on the speed versus frequency dispersion curves. Examples of guided waves can include Lamb waves, Rayleigh surface waves, Stonely and Loves interface waves, torsional, longitudinal and flexural waves in rods and pipes, etc.

Rayleigh surface waves are mechanical waves that propagate along the surface of a semi-infinite solid. They are characterized by free mechanical stress at the surface of the medium and a fast decay of the disturbance inside. A variety of techniques can be used to generate Rayleigh surface waves including, for example: i) a shear wave transducer placed directly on the surface, ii) an angle beam transducer, and iii) a mediator technique.

Lamb plate waves are similar to Rayleigh surface waves but propagate in plate-like structures bounded by two surfaces and require the stress to vanish at both surfaces. Lamb waves can be subcategorized into symmetric (S) and anti-symmetric (A) modes, characterized respectively by a symmetric and anti-symmetric distribution of the displacement field with respect to the mid-plane of the plate. Lamb waves can be generated similarly to Rayleigh waves, for example by using an angle beam transducer. Comb array transducers can also be used. The comb array technique for generating guided Lamb waves can include aligning a number of transducers with a constant spacing to generate a wave of constant wave length (equal to the spacing).

Phased transducer arrays may be used to generate guided waves in pipes. Phased transducer arrays work in a similar way as comb arrays except that time delays between array elements are used to improve the mode selection. As compared to traditional comb arrays for which the wavelength is changed by changing the element spacing, in phased arrays, this can be done through the time delay. In phased arrays, the same mode can be excited at different frequencies by changing the time delay. Beside phased arrays, the angle beam technique can be used to excite certain modes in slender structures.

Although most guided waves are dispersive, the wave speed for some guided waves such as the zero-order Lamb mode is constant over a certain range of frequencies. Additionally, the zero-order torsional mode in slender structures is non-dispersive over the whole frequency range.

Figure 48:
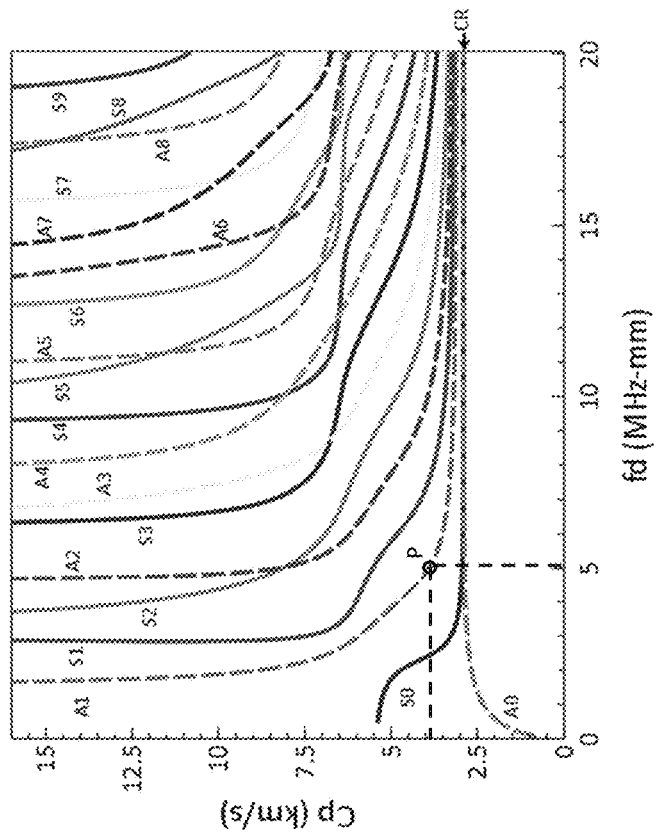
FIG. 48 is a plot showing plate wave dispersion curves for Aluminum. A1 mode can be generated by targeting the coordinates of Point P.

Due to their dispersive nature, it can be difficult to generate guided waves with multiple frequency components excitation signal (their speed or wavelength would be frequency-dependent). However, for a single frequency wave the generation may be relatively achievable. A given mode can be excited by targeting a specific point on the velocity versus frequency dispersion curve. The wave could be generated such that its velocity and frequency match the coordinates of that point on the graph (e.g., Point P in FIG. 48).

A single-frequency continuous wave can also be generated, but as explained by Craig S., 2013. "Modulated Continuous-waves Waveforms for Non-Destructive Examination". AECL Technical Document, Ref. 153-120000-401-0014, such a wave cannot be used for UT testing because it would be impossible to determine the time delay. That is, if there is more than one cycle, it would not be possible to determine if the time delay is less or more than a cycle because the signal cycles overlap. To overcome this difficulty, multiple frequencies or modulation schemes can be used. In particular, frequency sweeps such as linear frequency modulated (LFM) signals are commonly used in the continuous wave methods.

A frequency sweep of this nature may not be readily conducted with a classic comb transducer because in order to follow the dispersion curve of a given mode, when the frequency is varied, the wavelength has to be varied too, hence the element spacing. This may be impractical in some embodiments of the systems 100 herein as the element spacing cannot be easily varied at the sweep speed. This assessment remains generally valid for "non-dispersive" portions of the dispersion curves where the phase velocity is constant as a function of frequency. Even in this case, the wavelength, which is inversely proportional to the frequency ($1=2\pi v/\omega$) still varies with frequency. In some embodiments, the frequency range of the input signal can be limited to frequencies for which the phase velocity is generally and preferably substantially constant.

The angle beam method, on the other hand, may offer the possibility of generating and maintaining a given guided wave mode over a frequency range, provided that the mode is non-dispersive over this frequency range. One potential advantage of the angle beam method in the applications described herein may be that waves of constant phase speed can be generated over a range of frequencies while keeping the angle of incidence substantially constant. Since the speed of the refracted wave is determined by the angle and speed of the incident wave, based on Snell's Law, this technique may help provide a way to perform a frequency sweep at constant wave speed. For a constant angle of incidence, the refracted wave speed would be constant regardless of the frequency (the speed of the bulk l-wave or s-wave being constant for a given material). From FIG. 48 it can be seen that from 5 MHz-mm to 20 MHz-mm, the S0 and A0 modes converge towards the Rayleigh wave which has an approximately constant velocity equal to 2.89 km/s for Aluminum. Therefore, by selecting the angle of incidence such that the generated wave velocity is equal to 2.89 km/s, this wave may be generated and maintained over this range of frequencies.

Another method to perform frequency sweeping of guided waves may be the phased array method. Phased arrays may be controlled through time delay between array elements, which can be changed simultaneously as the frequency is varied, to excite and maintain the desired mode. The wavelength of the forward guided wave mode generated by a linear transducer array can be expressed as:

$$\lambda = L/(n + t_0 f),$$

where L is the element spacing, n the mode number, $t_0$ the time delay between two consecutive transducers and f the frequency of the harmonic mode.

In this equation the time delay can be changed electronically to produce a desired wavelength. In addition to the computed time delay, there may also be also an intrinsic time delay that can be accounted for. The intrinsic time delay may arise from relatively small variations in element phase responses that result from element coupling or transducer manufacturing processes. It can be determined by measuring the phase difference between the array elements from a reference signal such as a backwall echo. If the intrinsic phase of the elements is frequency-independent and provided that the controller can be programmed, the phased arrays technique may be suitable to be used to perform a frequency sweep. However, although the equation above was derived to maximize the response of Mode", other modes may be excited as well.

In addition to angle beam and phased array methods, Electromagnetic Acoustic Excitation (EMAT) devices can be used for generation of shear horizontal guided waves in plates.

While mathematical and numerical computations have shown that theoretically, the time delay between transmitted and received signals (wave travel time) can be deduced even in the case of a dispersive wave, as long as the sweep is computed to follow the dispersion curve the abovementioned practical limitations still apply. The phased array method can potentially be used, but the issue of multiple mode generation remains.

For all these reasons, the experiments described herein were conducted to focus on the portions of the dispersion curves where the phase speed is constant over an extended range of frequencies. For Lamb waves, the S0 and A0 modes merge to create Rayleigh wave at large values of fd (see FIG. 48). The angle beam method may be used to generate and maintain the Rayleigh-Lamb wave over this range of frequencies.

These techniques may have several possible applications, including contact detection, vibration measurement and flaw/discontinuity localization.

Regarding flaw/discontinuity localization, experiments described herein were created to focus on two types of structures, plate-like and tube-like structures, which can simulate a large number of industrial components. Such applications may utilize corresponding dispersion curves for guided wave mode selection, such as a plate Lamb wave dispersion curve when the object is plate-like. Such curves may be obtained or generated in any suitable manner.

If the systems described herein are configured to use guided waves, the transmitters 104 and the like can be guided wave transducers, including those described herein.

Using some embodiments of the systems and methods described herein may at least partially depend on linear frequency sweep and a constant speed of sound, i.e., the sound velocity does not change with frequency. In such instances, the frequency $f_R$ of the peak in the FFT spectrum corresponding to reflection from distance $d_i$ is given by Equation 11. For waveguides, the speed of sound (both phase velocity and group velocity) may tend to vary based on the frequency, so v may not be constant during the linear frequency sweep and there may not be a single value for $f_R$ during the frequency sweep. This may lead to inaccuracies in determining the distance 138 ($d_t$) to a flaw 110 or other such reflector.

Phase velocity can describe the speed with which a single wave is moving, i.e., the speed at which any fixed (constant) phase of the wave-cycle is displaced. The Group Velocity of a wave is the velocity with which the overall shape of the wave amplitude (known as envelope of the wave, or a wave packet) propagates through space. For example, the dependence of a one-dimensional harmonic wave S on time (t) and position (x) is given by:

$$S(x,t)=A.\sin(\theta(x,t))=A.\sin(\omega.t-k.x) \qquad (43)$$

where A is the wave amplitude, $\theta(x,t)=\omega.t-k.x$ is the wave phase, $\omega$ is the circular frequency, k is the wave number, $\lambda$ is the wavelength, f is the frequency, and T is the period. The following dependencies exist between these parameters:

$$\omega = \frac{2\cdot\pi}{T} = 2\cdot\pi\cdot f; k = \frac{2\cdot\pi}{\lambda}; T = \frac{1}{f} = \frac{2\cdot\pi}{\omega} \qquad (44)$$

For Phase Velocity, the speed of propagation of a constant phase can be calculated, i.e., $\theta(x,t)=\omega.t-k.x=\text{const.}$ From here:

$$\frac{\partial\theta}{\partial t} = \omega - k\cdot\frac{\partial x}{\partial t} = 0, \text{ or } \frac{\partial x}{\partial t} = \frac{\omega}{k} \qquad (45)$$

The Phase Velocity can then be defined as $$V_P = \frac{\partial x}{\partial t} = \frac{\omega}{k} = \frac{\lambda}{T} = f\cdot\lambda \qquad (46)$$

For Group Velocity, the phase $\theta(x,t)=\omega.t-k.x$ may not be constant, and the circular frequency $\omega$ may not be directly proportional to the wave number k. The definition of Group Velocity is:

$$V_G = \frac{\partial\omega}{\partial k} = V_P - \lambda\cdot\frac{\partial V_P}{\partial\lambda} = V_P + k\cdot\frac{\partial V_P}{\partial k} \qquad (47)$$

The group velocity can be thought of as the velocity at which energy or information is conveyed along a wave, i.e., the group velocity can be considered the signal velocity of the waveform. The function $\omega(k)$, which gives $\omega$ as a function of k (or f as a function of $\lambda$), is known as the dispersion relation. If $\omega$ is directly proportional to k, then the group velocity can be equal to the phase velocity, and a wave of any shape may travel undistorted at this velocity. For ultrasound propagation, dispersion may be defined as the dependence of the sound velocity (both phase and group velocity) on the frequency of the sound. For UT applications, calculation of refraction angles using Snell's Law is based on phase velocity, so phase velocity was used for the calculations presented below.

Figure 30:
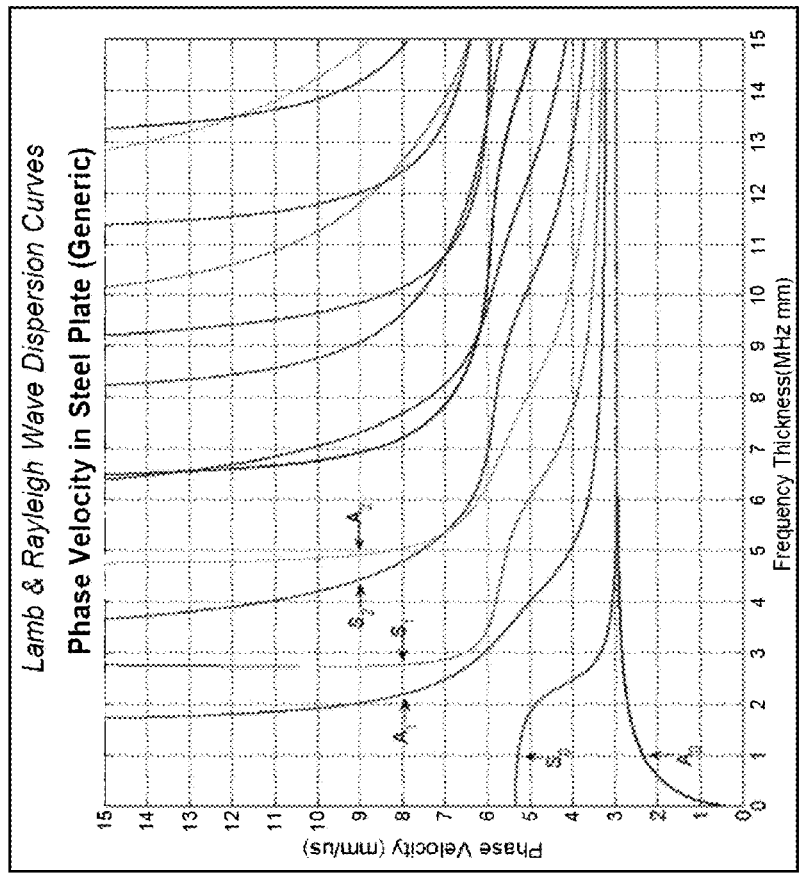
FIGS. 29 and 30 are sound dispersion curves for Lamb and Rayleigh waves in steel plates.
Figure 29:
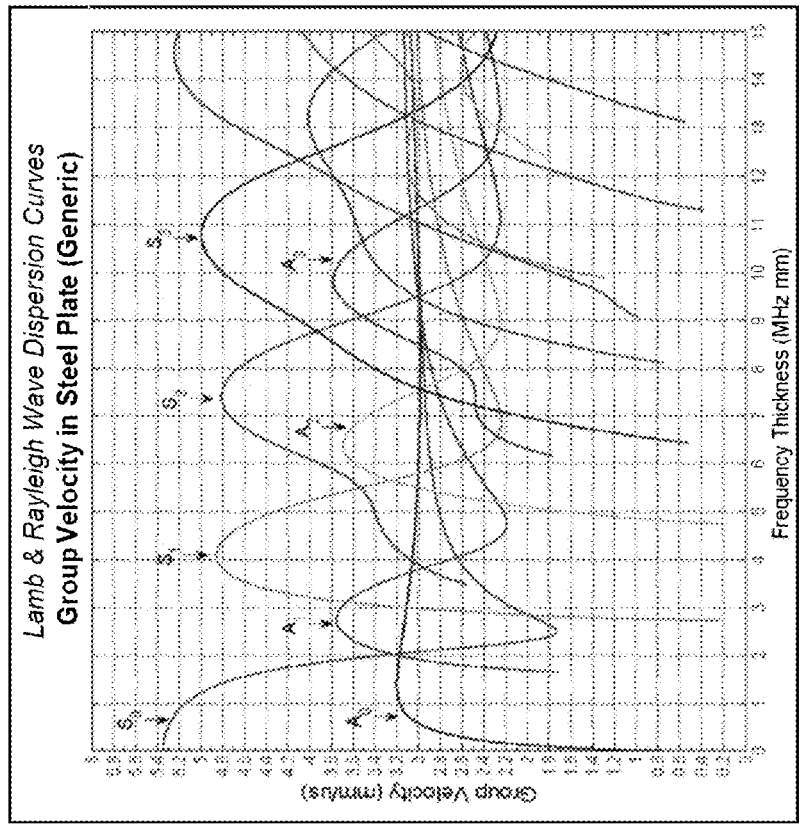
Figure 32:
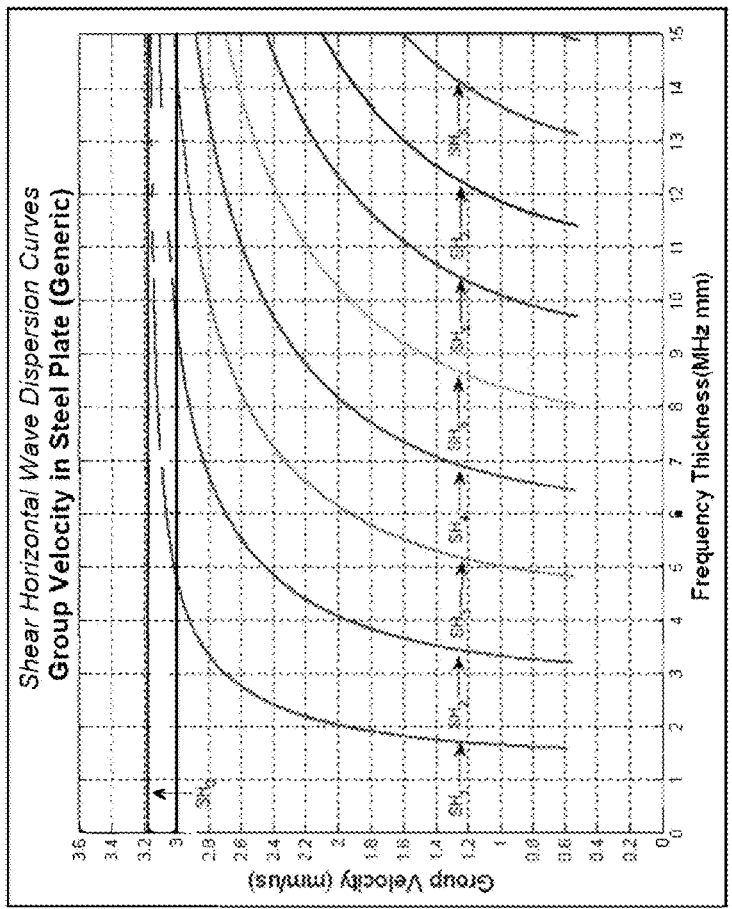
FIGS. 31 and 32 are sound dispersion curves for shear horizontal waves in steel plates.
Figure 31:
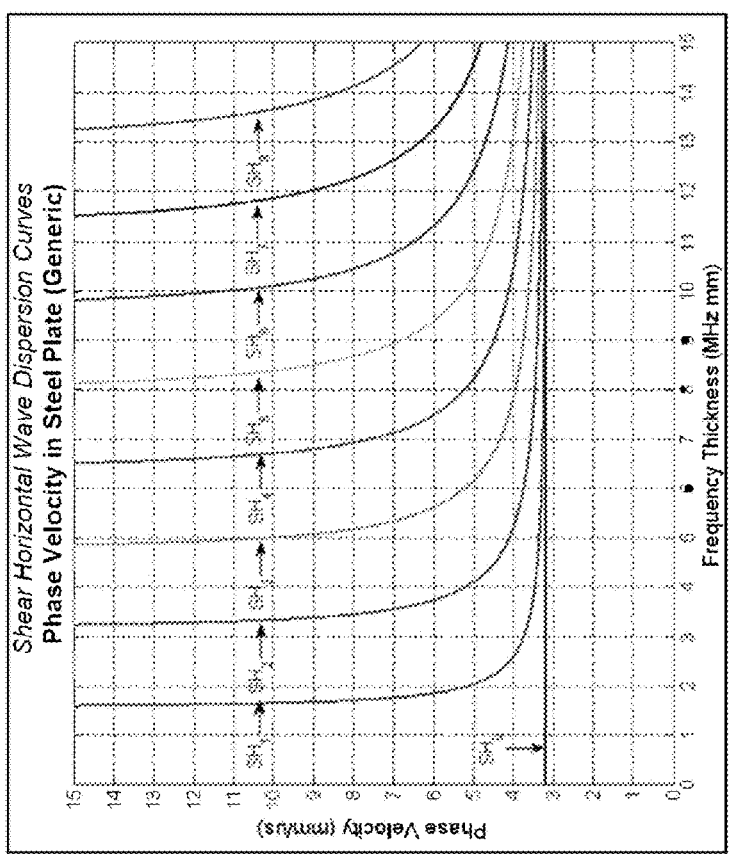

Information about phase and group velocity of sound in different material as a function of frequency times thickness may be available from multiple references. Some examples of sound dispersion curves for group and phase velocities in steel plates are shown in FIGS. 29 and 30 (for Lamb and Rayleigh waves)) and FIGS. 31 and 32 (for Shear Horizontal waves).

Longitudinal modes L(0,m) and torsional modes T(0,m) are S-modes (i.e., symmetrical waves in respect to the axis of the direction of propagation). Flexural modes F(n,m) are A-modes, i.e., anti-symmetrical waves. Here index "m" represents the number of nodes perpendicular to the axis, while "n" is the circumferential order (0 for plates).

Software was developed to generate a non-linear frequency sweep function, which will lead to a constant value for the signal frequency $f_R$ during a frequency sweep in a waveguide. The software may also evaluate the difference in the signal generated by using linear and non-linear frequency sweep.

For the purposes of investigating the effect of sound dispersion on the continuous wave frequency modulated ultrasound inspection systems and methods herein, the following dispersion curves were modeled:

Linear.
Parabolic.
L(0,1)—longitudinal phase velocity (data taken from FIG. 30).
L(0,2)—longitudinal phase velocity (data taken from FIG. 30).

The following input parameters were provided to the software for each modeled case:

Dispersion Curve v(f) (defined as a function or as a set of (x,y) values).
Start Time $t_0$.
Time-increment step $\tau$ (one full calculation in performed at each step).
Start Frequency $f_0$.
Frequency Ramp Step $\Delta f$ for the linear sweep.
Distance to measured flaw d.

For each test case, a linear frequency sweep was calculated first for comparison purposes. At each step "i", the program calculates:

Time $t=t_0+i.t.$

Frequency $f_1(t)=f_0+i.Df$, $f_1$ is the frequency of the reference signal (signal traveling directly from the function generator via reference arm, see FIG. 1 or 2), which was generated at time t.
Sound velocity based on dispersion curve $v(f_1)$.
Delay time for traveling to flaw and back $Dt=2.d/v(f_1)$ (this is an approximation, ideally one should use $v(f_2)$, but the error is small for very close values of $f_1$ and $f_2$, i.e., for very small steps t and Df).
Time of the generation of the test arm signal (Test Signal): $t_2=t-Dt$.
Calculate the frequency $f_2$ of the test arm signal, using linear interpolation of the dispersion curve. The signal after the low-pass filter will have frequency $f_R=f_1-f_2$, which will be proportional to the distance to the flaw d, as per Equation (14).

The second part of the modeling involves calculation of the non-linear frequency sweep. During these calculations, for each step, the value of $f_1$ may be adjusted so a generally constant signal frequency is provided $f_R=f_1-f_2$:

For the first several points, we use the data calculated based on a linear sweep as described above.
For step "i", calculate time $t=t_0+i.t.$
For each time step i, loop frequency $f_1$ from $(f_0+(i-1).Df)$ to $(f_0+(i+1).Df)$ with a small step (for example, with step Df/100) and calculate:
Set initial $t_1=t.$
For each $f_1$, calculate $v(f_1)$, $Dt=2.d/v(f_1)$, $t_2=t_1-Dt$, and $f_2$ (corresponding to $t_2$) using linear interpolation based on previous sweep points.

Select this $f_1$, for which $(f_1-f_2)$ is equal (or closest) to a pre-determined constant value $f_R$.

Recalculate $v(f_2)$, $Dt=2.d/v(f_2)$, and calculate new optimized $t_1=t_2+Dt$ (usually the new $t_1$ is very close to the initial $t_1$, the difference is <0.005% of the value of $t_1$, or <1% of the value of the step t).

Use new $t_1$ and best $f_1$ as a new data point for the frequency sweep curve (non-linear frequency scan curve).

The above procedure may help facilitate constructing a new non-linear sweep curve f(t), which ensures constant value of $f_R$.

The first several points of the frequency sweep may be calculated with a linear sweep only, before starting the optimization, because the optimization method may, in some examples, require some "history" to work ($f_2$ is calculated using linear interpolation based on previous scan points). Because there is a discontinuity between the end of the linear sweep region and the optimized sweep, and because we are using previous points, this discontinuity may be repeated periodically.

One case that was examined was linear sound dispersion, i.e., the sound velocity was a linear function of sound frequency. This case may have practical uses as the sound velocity dispersion may be approximated with a linear curve within the frequency range used. The scan time in this example was from 1 to 1.1 sec (i.e., 0.1 sec total scan time), the frequency change was from 0.2 to 4.2 MHZ (sweep rate of 40 MHz/s), and the sound velocity change was from 3050 to 3500 m/s (i.e., more than 10%). A total of 200 steps were used. The time step t was 0.5 msec, and the frequency step Df was 0.02 MHz. Distance to the reflector was varied from 2 m to 12 m (if not specified, the Figures are shown for d=2 m).

Figure 33:
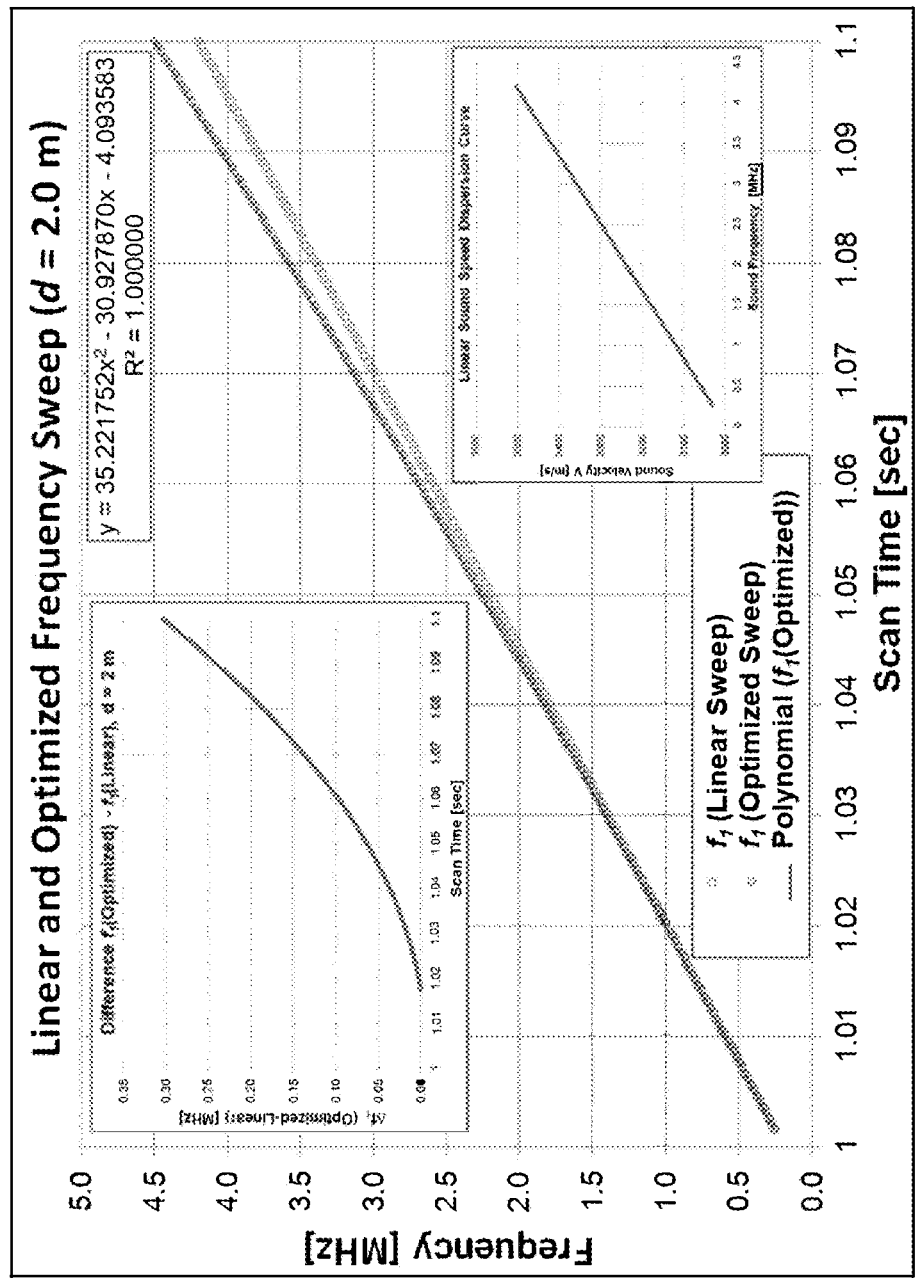
FIG. 33 is a plot showing one example of an optimized frequency sweep for linear dispersion.
Figure 35:
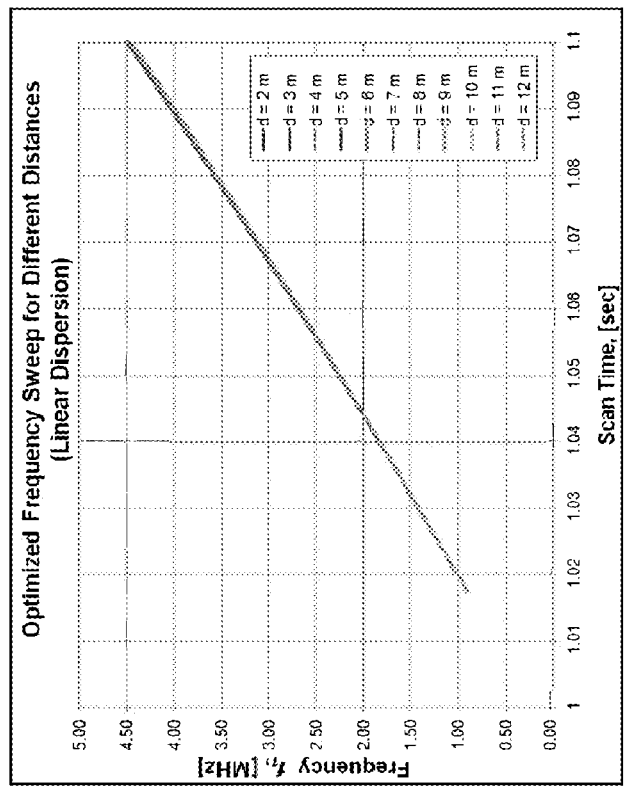
FIG. 35 is a plot showing one example of an optimized frequency sweep for different distances.
Figure 34:
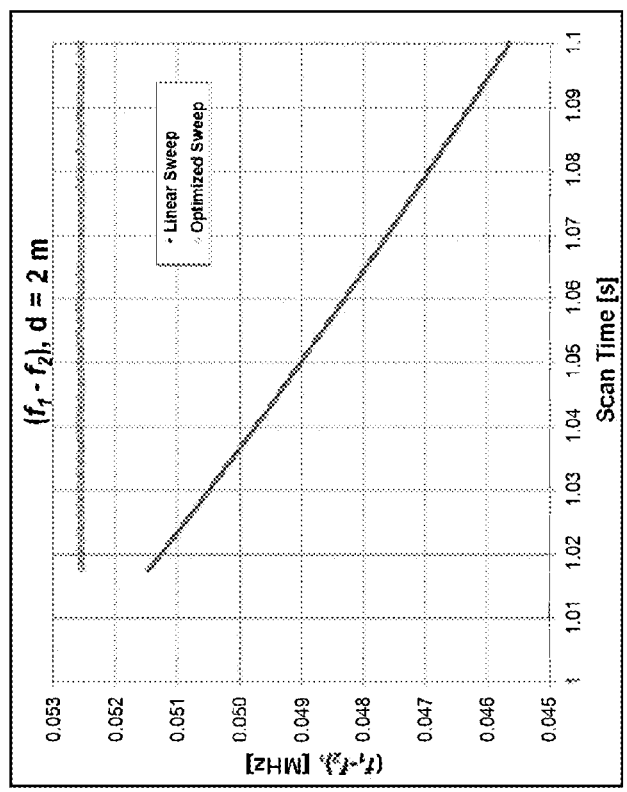
FIG. 34 is a plot showing the difference ($f_1$–$f_2$) during frequency sweep.

The linear frequency sweep and the optimized non-linear frequency sweep are shown in FIG. 33. In this example, the optimized frequency sweep can be fitted substantially perfectly with a parabolic function. The bottom-right insert shows the dispersion curve, and the top-left insert shows the difference between the linear and the optimized frequency sweep. The maximum difference is at the end of the scan (0.3 MHZ, or less than 10% difference from the linear sweep value). The difference between initial $t_1$ and optimized $t_1$ was always <$3\times10^{-6}$ s, or <0.6% of time step t, and it can be assumed that for practical purposes initial $t_1$ and optimized $t_1$ are equal. FIG. 34 shows the difference $(f_1-f_2)$ during the scan. In this example, for the optimized frequency sweep, this difference is constant at around 52.5 kHz, while for the linear frequency sweep, the difference changes (decreases) by more than 10% from its initial value. The first several points of the frequency sweep are not shown, because they were calculated with linear sweep only (before starting the optimization, because the optimization method requires some "history" in order to work). FIG. 35 shows the dependence of the optimized non-linear frequency sweep on the distance to the reflector. As can be seen, there is no significant change in the frequency sweep curve when the distance is changed from 2 m to 12 m in this example.

The second case examined was parabolic sound dispersion, i.e., sound velocity was a quadratic function of sound frequency. The scan time was from 1 to 1.2 sec (i.e., 0.2 sec scan time, 100 scan steps, time step t was 2 msec), the frequency changes from 1 to 6 MHZ (sweep rate of 25 MHz/s), and the sound velocity changes from 3250 to 3550 m/s (i.e., around 10%). Distance to the reflector was varied from 2 m to 6 m in this example.

Figure 36:
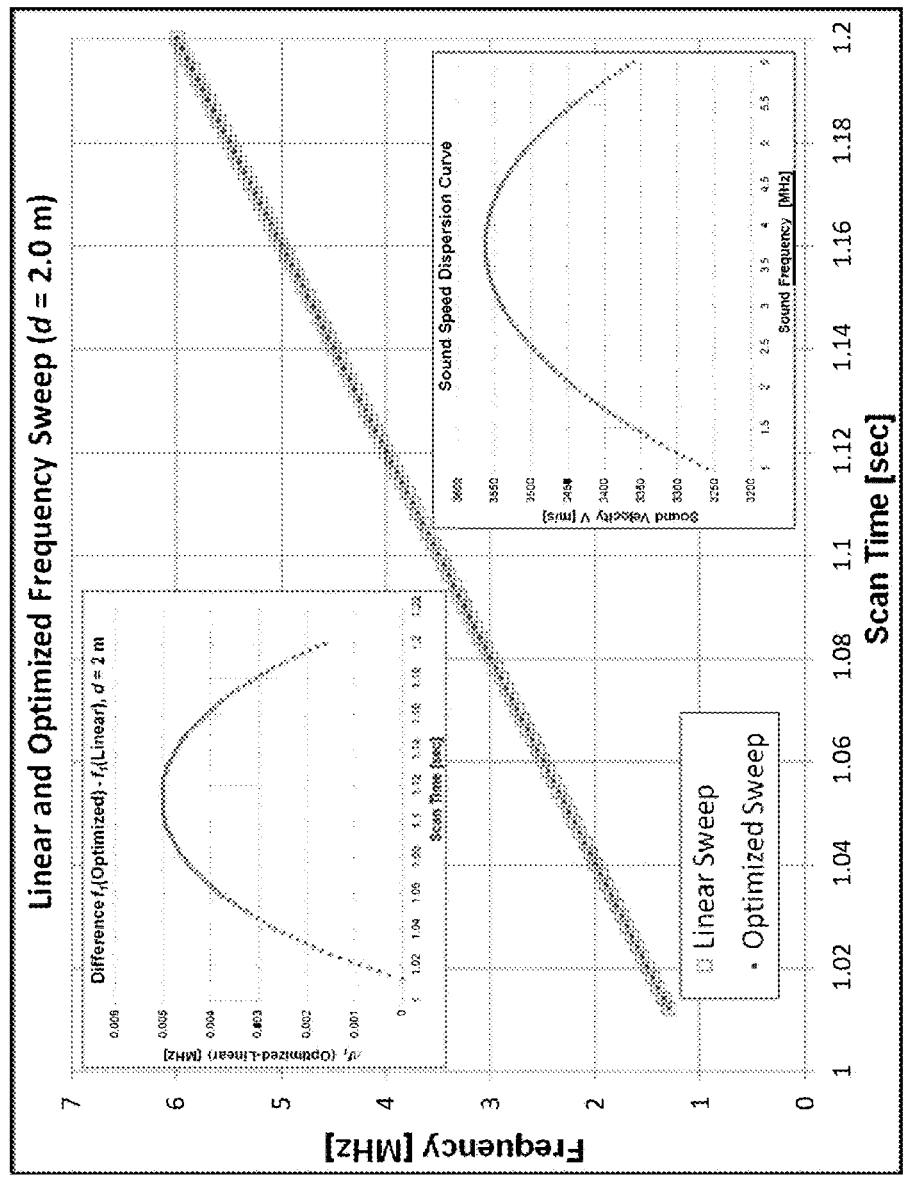
FIG. 36 is a plot showing one example of an optimized frequency sweep for parabolic dispersion.

The linear frequency sweep and the optimized non-linear frequency sweep for the parabolic dispersion case are shown in FIG. 36. As can be seen, the optimized frequency sweep is very close to the linear sweep. The bottom-right insert shows the dispersion curve, and the top-left insert shows the difference between the linear and the optimized frequency sweep. The maximum difference between linear and optimized frequency sweep is <0.2% (i.e., difference of about 5 kHz at frequency of about 4 MHZ). The difference between initial $t_1$ and optimized $t_1$ was <$3\times10^{-6}$ s, or <0.2% of time step t, so we can assume that for practical purposes initial $t_1$ and optimized $t_1$ are equal.

Figure 37:
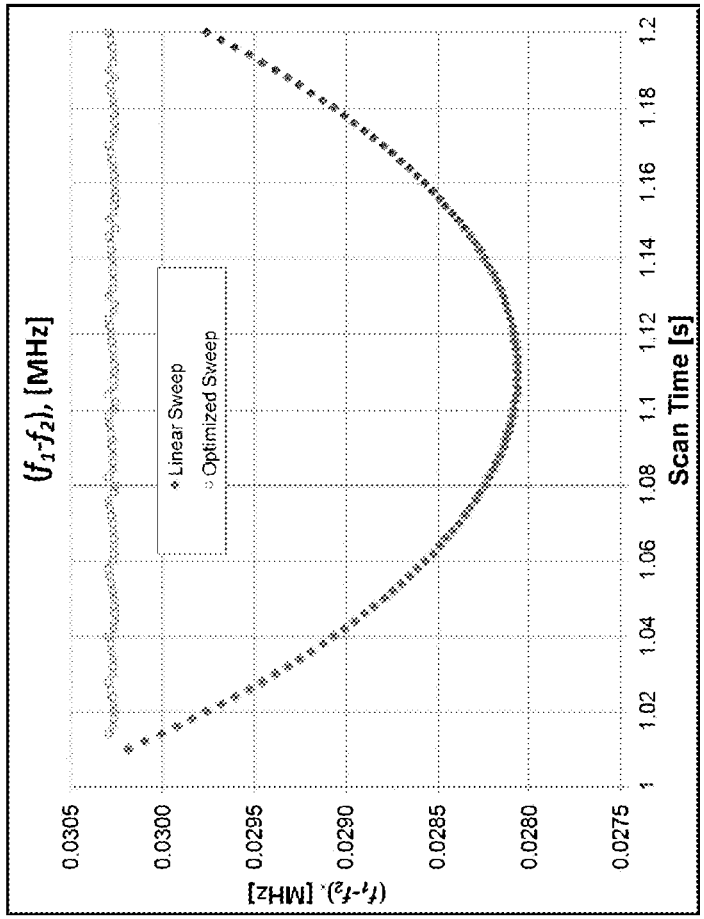
FIG. 37 is a plot showing the difference ($f_1-f_2$) during frequency sweep for the data shown in FIG. 36.

FIG. 37 shows the difference $(f_1-f_2)$ during the scan. As can be seen, for the optimized frequency sweep, this difference is constant at around 30.2 kHz, while for the linear frequency sweep, the difference changes by about 10% from its initial value. The first several points of the scan are not shown, because they were calculated with linear sweep only (before starting the optimization, because the optimization method requires some "history" in order to work).

Figure 38:
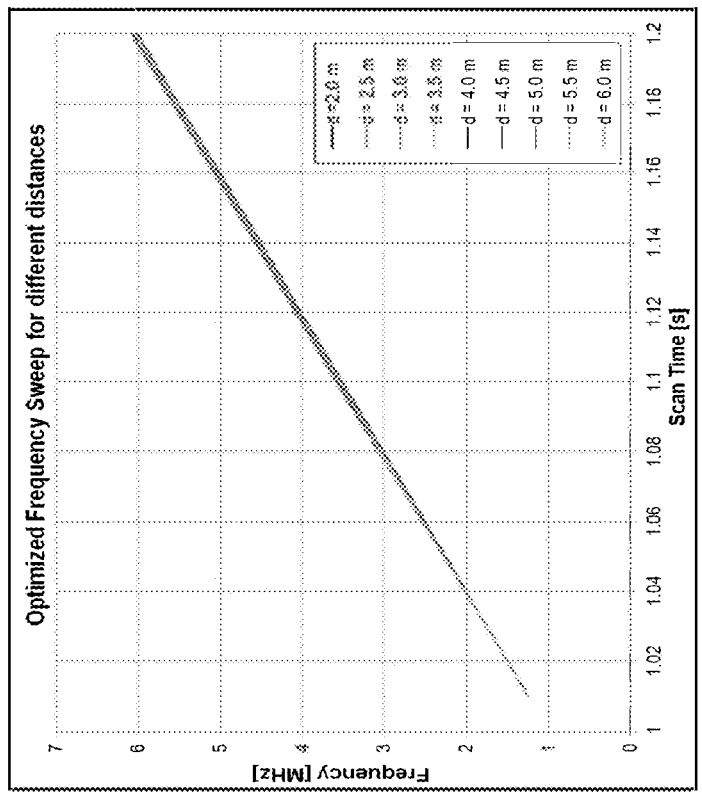
FIG. 38 is a plot showing one example of an optimized frequency sweep for different distances for the data shown in FIG. 36.

FIG. 38 shows the dependence of the optimized non-linear frequency sweep on the distance to the reflector. As can be seen, there is no significant change when the distance changes from 2 m to 6 m in this example. The third case examined was for L(0,1) dispersion curve. Data for L(0,1) was taken from J. Li, J. L. Rose, "Excitation and Propagation of Non-Axisymmetric Guided Waves in a Hollow Cylinder", J. Acoust. Soc. Am., v. 109(2), p. 457-464 (2001), which is incorporated herein by reference. The scan time was from 1 to 1.2 sec (i.e., 0.2 sec total scan time, 100 time steps, each time step t was 2 msec), the frequency changes from 0.2 to 5.2 MHZ, and the sound velocity changes from 2200 to 5500 m/s (i.e., more than a factor of two). Distance to flaw was 2 m to 6 m in this example.

Figure 39:
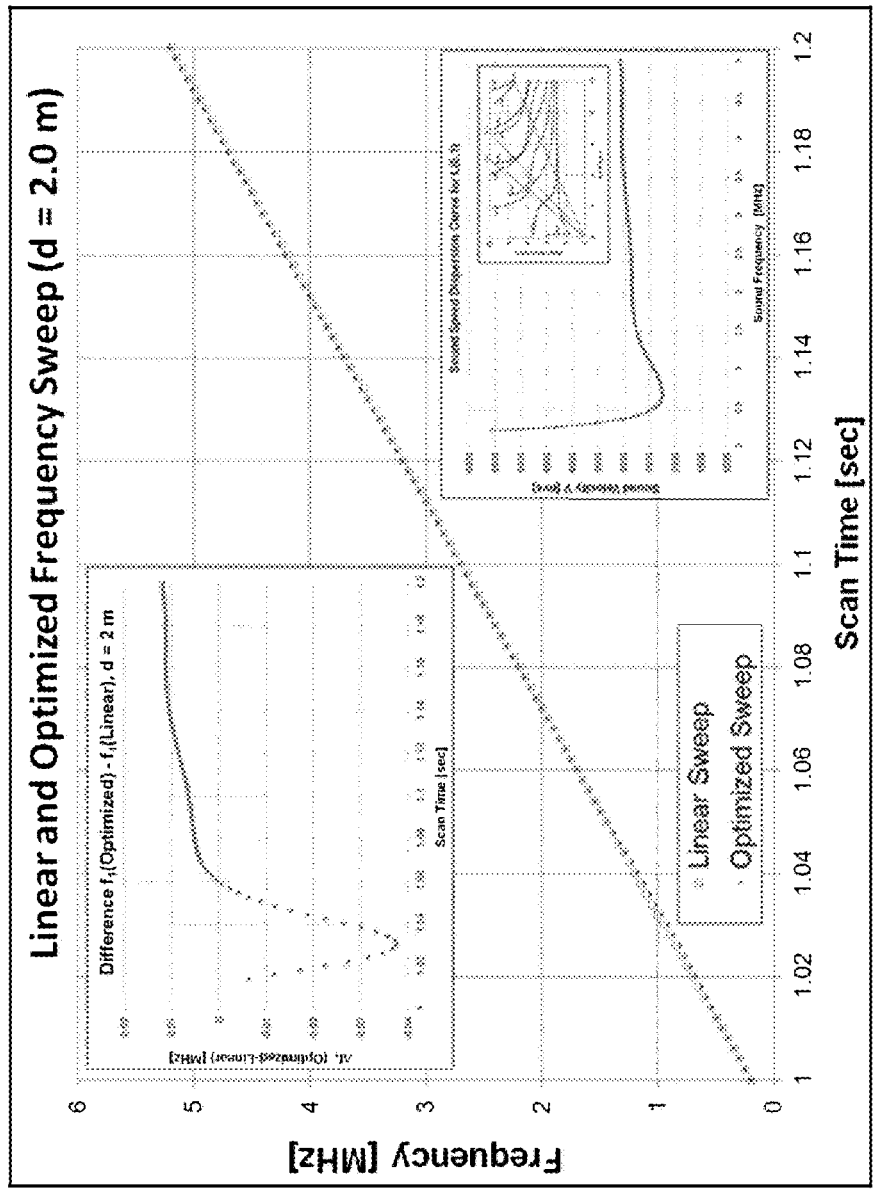
FIG. 39 is a plot showing one example of an optimized frequency sweep for L(0,1) dispersion curve.

The linear frequency sweep and the optimized non-linear frequency sweep for the L(0,1) dispersion curve are shown in FIG. 39. As can be seen, the optimized frequency sweep is close to linear sweep. The bottom-right insert shows the L(0,1) dispersion curve, and the top-left insert shows the difference between the linear and the optimized frequency sweep. The maximum difference between linear and optimized frequency sweep was <4% (i.e., difference of about 0.04 MHz at frequency of about 1 MHZ). The difference between initial $t_1$ and optimized $t_1$ was <10-5 s, or <6% of time step t.

Figure 40:
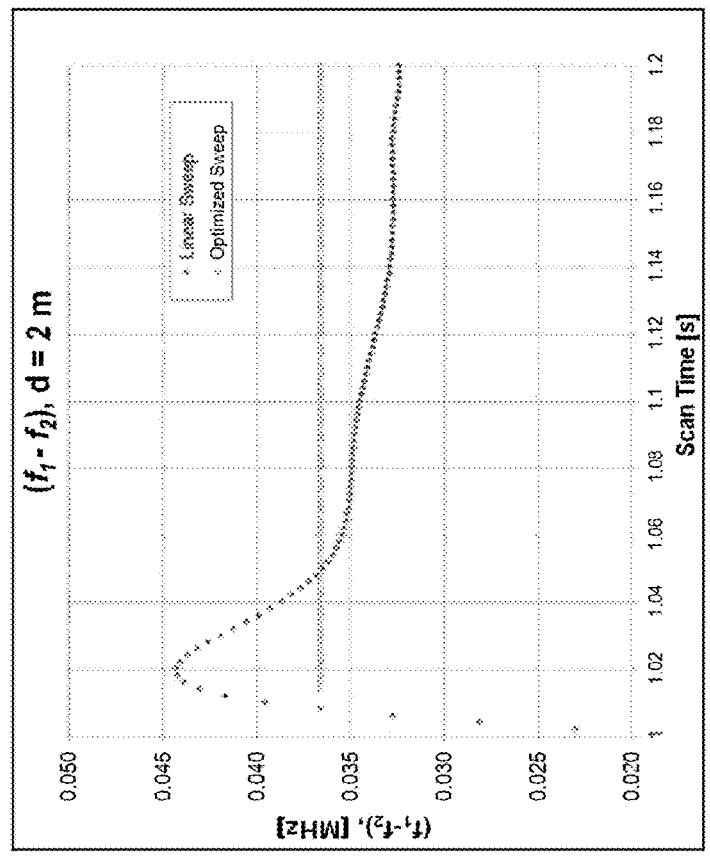
FIG. 40 is a plot showing the difference ($f_1-f_2$) during frequency sweep for the data shown in FIG. 39.

FIG. 40 shows the difference $(f_1-f_2)$ during the scan. As can be seen, for the optimized frequency sweep, this difference is constant at around 36.7 kHz, while for the linear frequency sweep, the difference changes by about 10% from its initial value.

Figure 41:
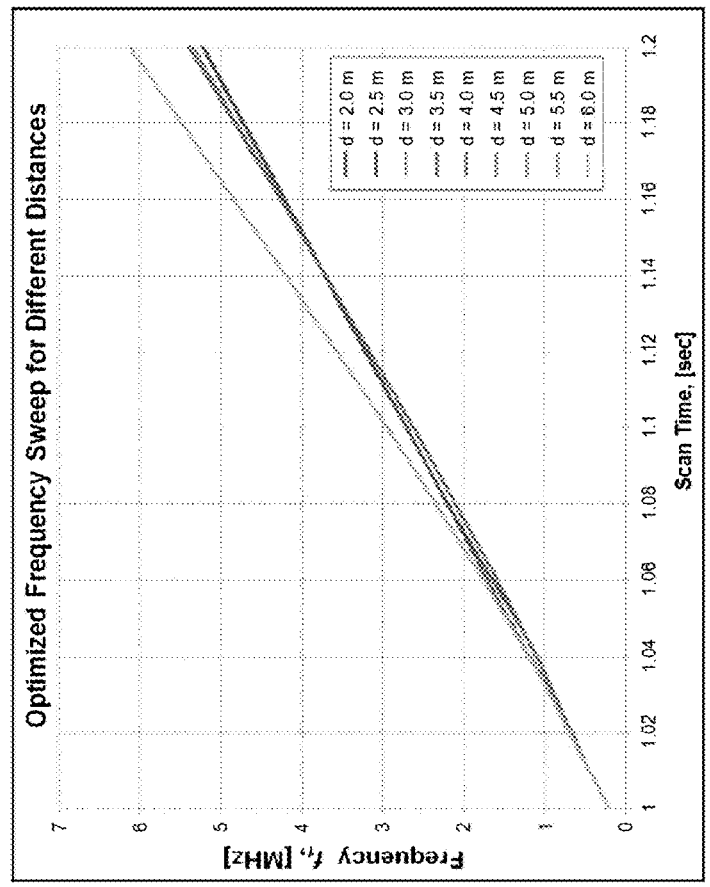
FIG. 41 is a plot showing one example of an optimized frequency sweep for different distances for the data shown in FIG. 39.

FIG. 41 shows the dependence of the optimized non-linear frequency sweep on the distance to the reflector. There are 2 groups of scans: (i) for distance to flaw from 2 to 4 m, the frequency sweeps are close to each other and they end at around 5.2 MHZ; (ii) for distance from 4.5 to 6 m, the frequency sweeps are practically the same and they end at ~ 6.1 MHz.

The fourth case examined was L(0,2) dispersion curve. Data for L(0.2) was also taken from J. Li, J. L. Rose, "Excitation and Propagation of Non-Axisymmetric Guided Waves in a Hollow Cylinder", J. Acoust. Soc. Am., v. 109(2), p. 457-464 (2001). The scan time is from 1 to 1.2 sec (0.2 sec total scan time, 100 scan steps, time step t was 2 msec), the frequency changed from 0.2 to 4.2 MHz, and the sound velocity changed from 3500 to 6200 m/s (i.e., approximately 2 times). Distance to reflector was 2 m to 6 m in this example.

Figure 42:
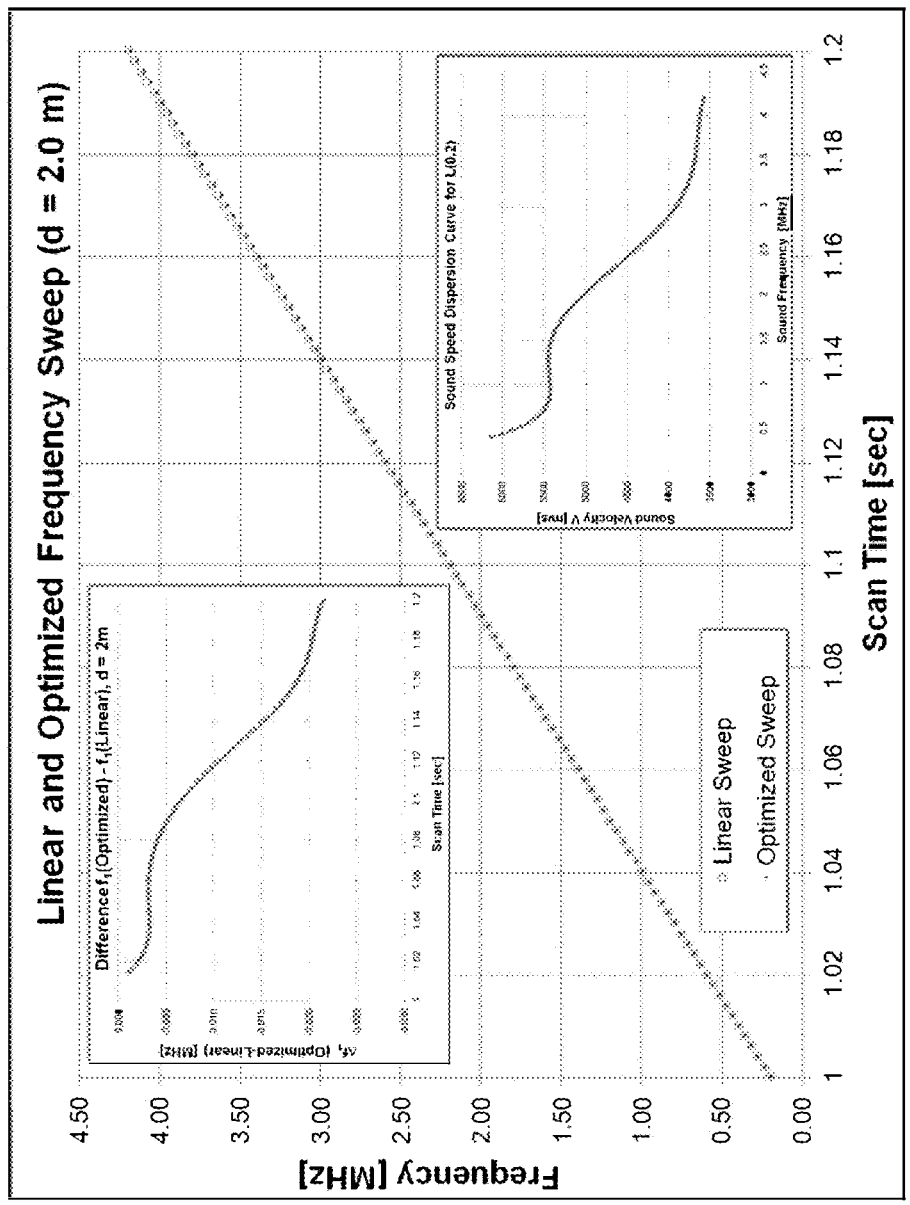
FIG. 42 is a plot showing one example of an optimized frequency sweep for L(0,2) dispersion curve.

The linear frequency sweep and the optimized non-linear frequency sweep for the L(0,2) dispersion curve are shown in FIG. 42. As can be seen, the optimized frequency sweep is close to linear sweep. The bottom-right insert shows the L(0,2) dispersion curve, and the top-left insert shows the difference between the linear and the optimized frequency sweep. The maximum difference between linear and optimized frequency sweep was <0.5% (i.e., difference of about 0.022 MHz at frequency of about 4.2 MHZ). The difference between initial $t_1$ and optimized $t_1$ was <5×10-6 s, or <0.3% of time step t.

Figure 43:
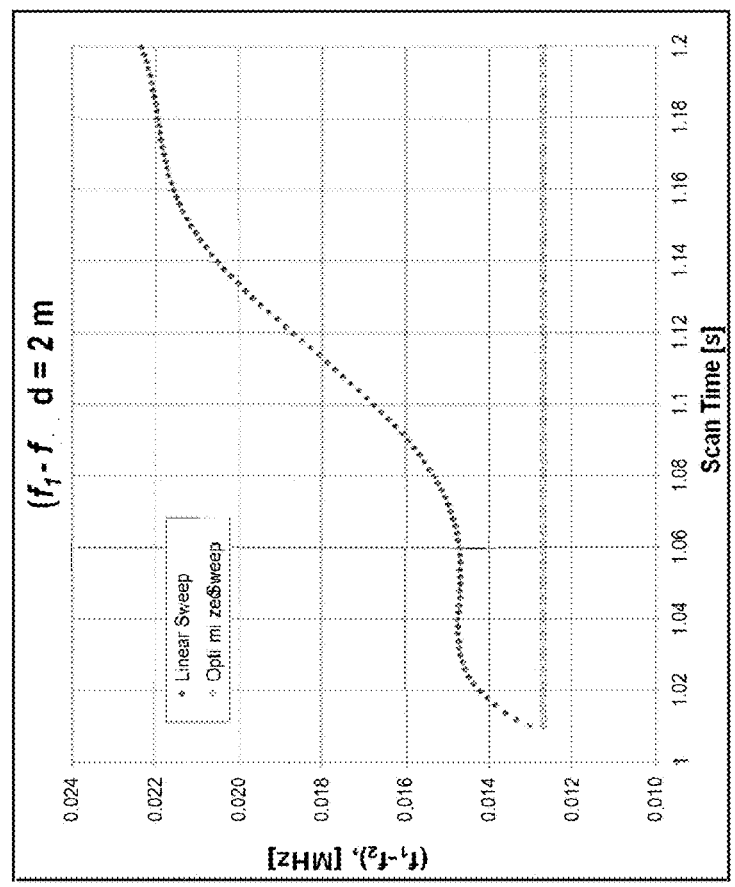
FIG. 43 is a plot showing the difference ($f_1-f_2$) during frequency sweep for the data shown in FIG. 42.

FIG. 43 shows the difference ($f_1$–$f_2$) during the scan. As can be seen, for the optimized frequency sweep, this difference is constant at around 12.7 kHz, while for the linear frequency sweep, the difference changes almost two times from its initial value.

Figure 44:
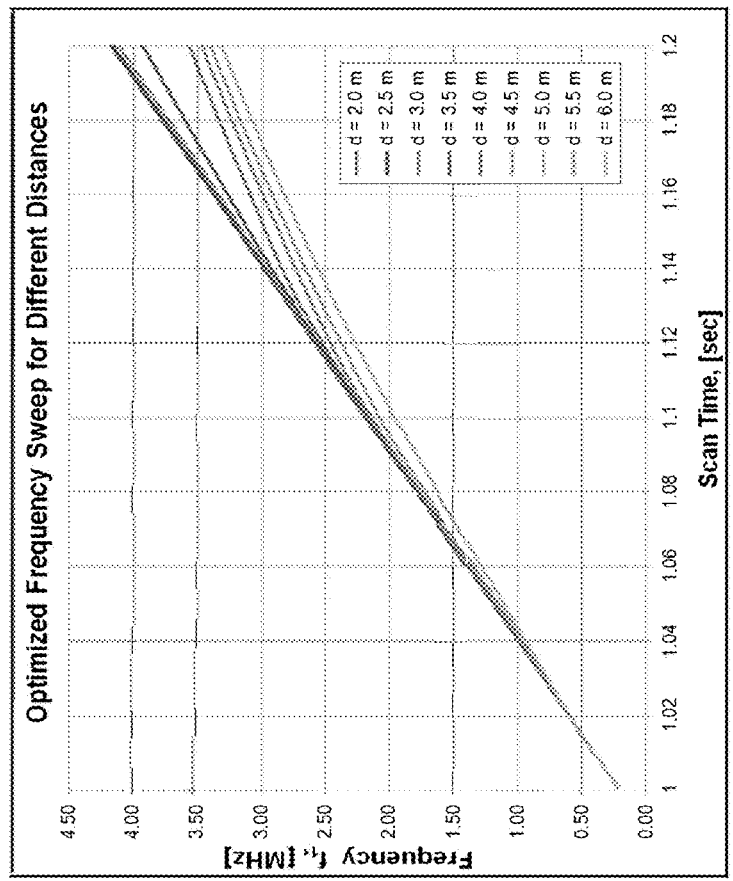
FIG. 44 is a plot showing one example of an optimized frequency sweep for different distances for the data shown in FIG. 42.

FIG. 44 shows the dependence of the optimized non-linear frequency sweep on the distance to the reflector. As can be seen, the deviation from linear frequency sweep increases with increasing the distance to the reflector.

Figure 49:
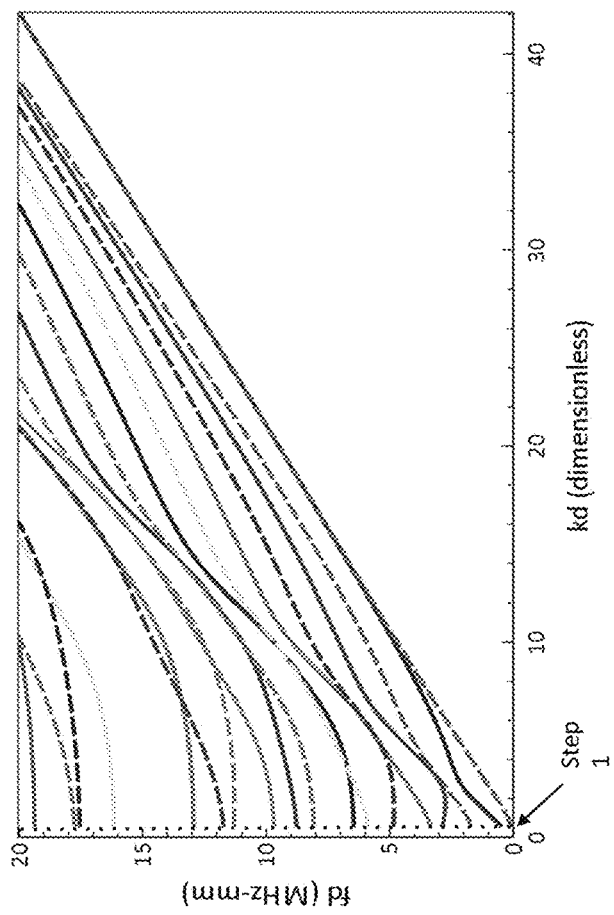
FIG. 49 is a plot showing wave number dispersion curves for steel.
Figure 50:
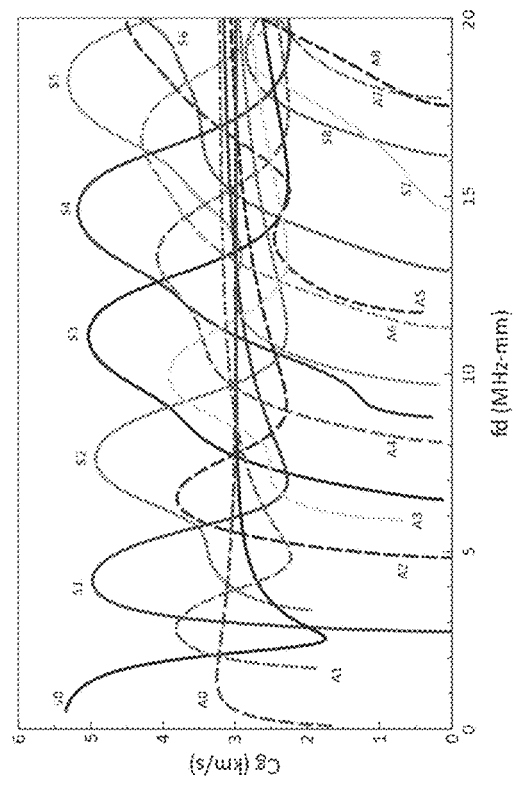
FIG. 50 is a plot showing phase velocity dispersion curves for steel.
Figure 51:
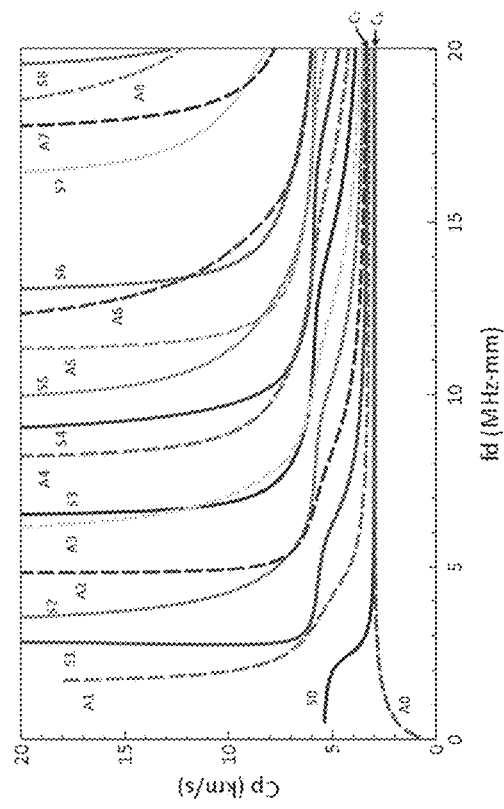
FIG. 51 is a plot showing group velocity dispersion curves for steel.
Figure 53:
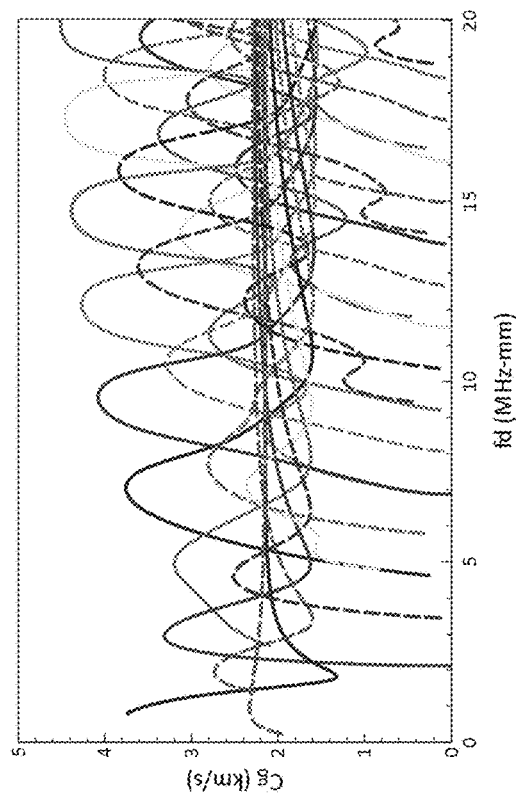
FIG. 53 is a plot showing group velocity dispersion curves for zircaloy.
Figure 52:
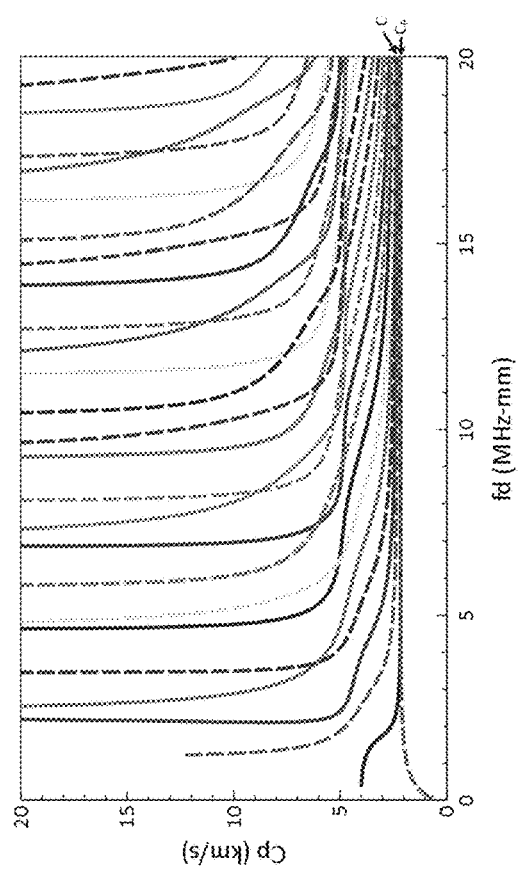
FIG. 52 is a plot showing phase velocity dispersion curves for zircaloy.

Other examples of dispersion curves generated by the inventors during the experiments described herein are included in FIGS. 49-53. In FIG. 49 Symmetric (S) modes are plotted in solid lines while antisymmetric (A) modes are plotted in dashed lines. As shown in FIG. 49, the first symmetric and antisymmetric modes merge into the Rayleigh-Lamb wave for large values of fd. This is also shown in FIGS. 50 and 51, where the phase velocities of the S0 and A0 modes converge toward the Rayleigh wave speed while that of the higher order modes converges towards the shear wave speed. An approximation of the Rayleigh wave speed was given by Viktorov ("Rayleigh and Lamb Waves, Physical Theory and Applications", Plenum Press, New York, USA, 1967) as $$v_R = v_T(0.87 + 1.12 P_R)/(1 + P_R),$$

where $P_R$ is the Poisson's ratio of the material. For steel ($v_L$=5.85 km/s and $v_T$=3.23 km/s), this formula gives $v_R$=2.99 km/s. For comparison, the phase velocity of the S0 mode plotted in FIG. 29 reaches 2.99 km/s at fd=6.7 MHz-mm and that of the A0 mode reaches 2.98 km/s at the same fd. The group velocity dispersion curves are also illustrated in FIGS. 51 and 53 for Steel and Zircaloy, respectively. It can be seen in FIG. 51 that the group velocity for the S0 and A0 converges towards the Rayleigh-Lamb wave speed ($v_R$=2.99 km/s) as expected. Note that group velocity and phase velocity are equal when they are constant.

Based on the teachings described herein, an experiment was conducted to investigate the use of continuous, frequency-modulated guided waves in a method to detect discontinuities in hollow tubing/piping. Guided waves in hollow cylindrical bodies are much more complex than their counterparts in plates. In cylindrical bodies, there are many types of guided waves: longitudinal, torsional, flexural and circumferential waves, each having an infinite number of modes. This study was focused on non-dispersive modes because the continuous wave method utilizes continuous frequency sweeping. In hollow cylinders, the zero-order torsional mode is non-dispersive over the whole range of frequencies. At large frequencies, this mode becomes identical to the fundamental mode which has the same wave speed as the Rayleigh-Lamb mode in plates. In addition, a number of torsional, longitudinal and flexural modes converge towards the same fundamental mode at large frequencies. On this basis, a number of experiments were conducted on a stainless steel (SS) piping to investigate flaw localization using continuous guided waves (CGW).

Figure 45:
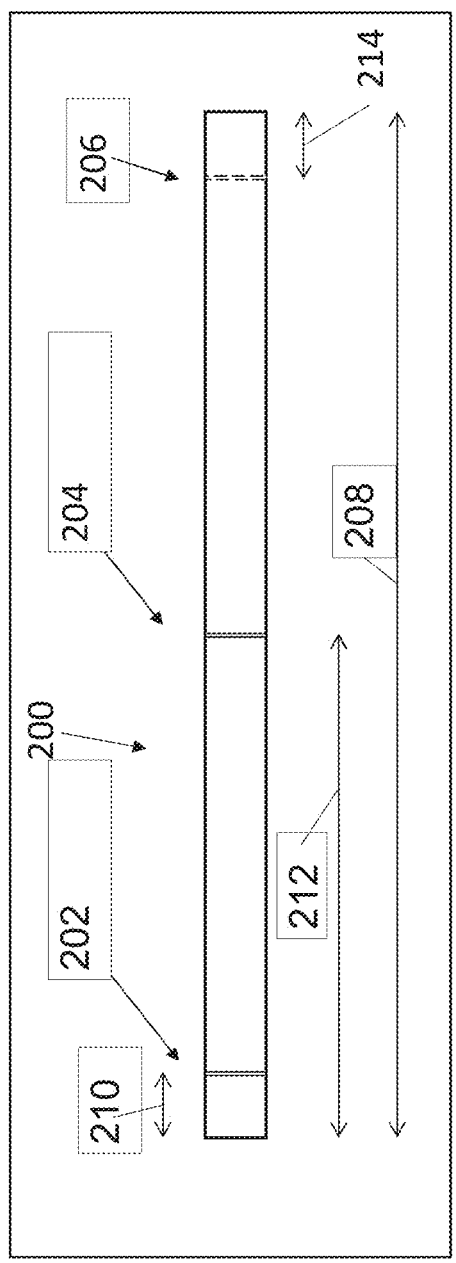
FIG. 45 is a schematic representation of one experimental test sample (pipe) with simulated flaws.

One embodiment of a continuous wave frequency modulated ultrasound inspection system and method was used to conduct an experiment on a 304 stainless steel pipe 200. Three notches 202, 204 and 206 were machined on the pipe, over its entire circumference as shown in FIG. 45. Two of these notches 202 and 204 were made on the outer surface, while the third 206 was machined on the inner face, close to one end of the pipe as shown schematically in FIG. 45. The dimensions of the notches are:

Outer Notch 202: 0.5 mm wide×1 mm deep (21% of wall thickness).

Outer Notch 204: 0.5 mm wide×0.5 mm deep (10% of wall thickness).

Inner Notch 206: 0.5 mm wide×0.5 mm deep (10% of wall thickness).

The pipe 200 has a length 208 of about 122 cm, an outer diameter of 4" (10.16 cm), and a wall thickness of 0.188" (4.77 mm). The notch 202 is located a first distance 210 from one end of the pipe 200. In this example, the first distance was about 11 cm. The notch 204 is located at a distance 212 of about 61 cm from the end. Notch 206 is located a distance 214 of about 11 cm from the opposing end of the pipe 200.

Figure 55:
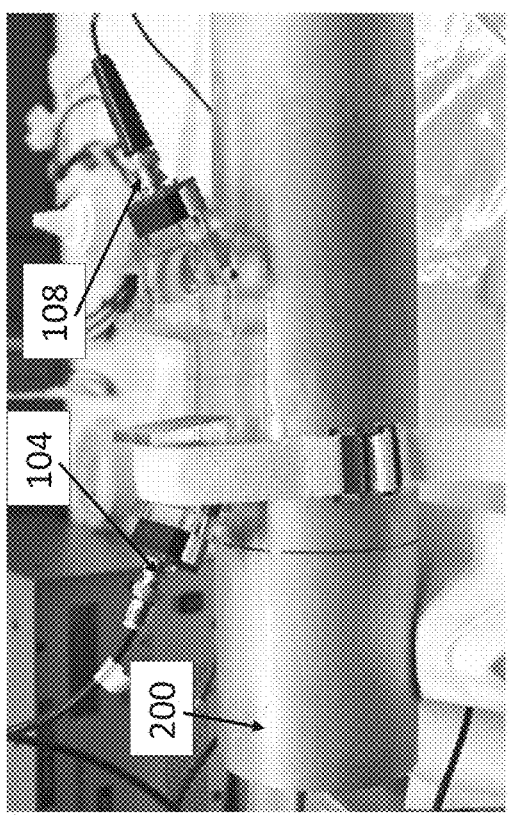
FIG. 55 is a photo of another experimental test set-up.

The same transducers and data acquisition system used for the plate testing described herein were used for the present test. Acrylic shoes (shown in FIG. 54) were designed to allow mounting the transducer wedges on the curved surface. A photograph of the two transducers, mounted on the pipe, is shown in FIG. 55. The angle of incidence of the wedge was set at around 63.7°, similarly to the plate wave experiment described herein.

Figure 46:
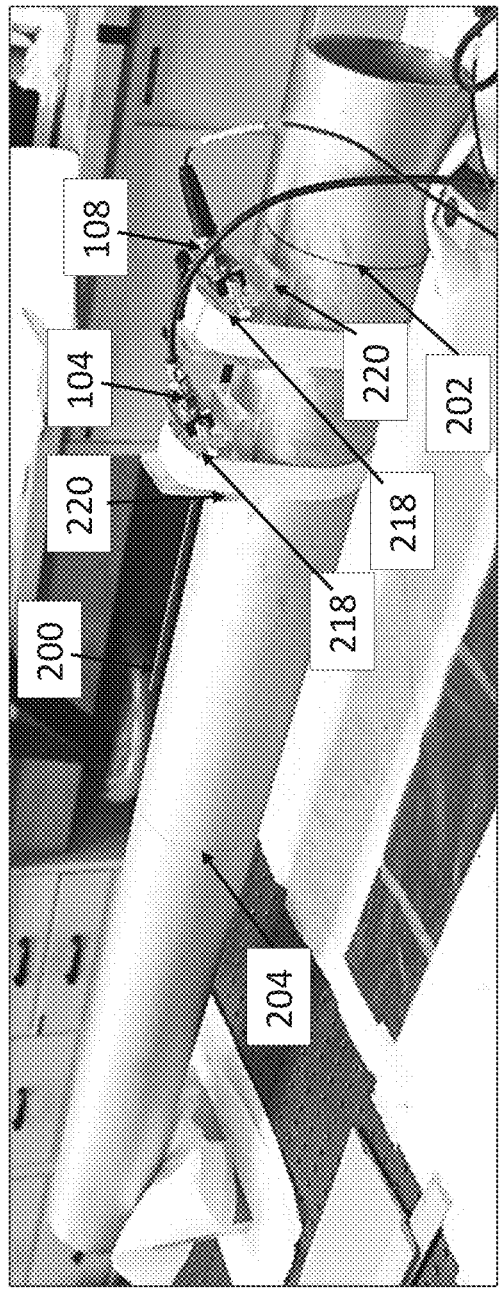
FIG. 46 is a depiction of one experimental test sample (pipe, as shown in FIG. 45) used in combination with one example of a continuous wave frequency modulated ultrasound inspection system.

Referring also to FIG. 46, the physical experimental apparatus used is illustrated. In this experiment both the transmitter 104 and the receiver 108 were Olympus™ UT transducers, model V405-SB (5 MHZ). They were mounted on variable angle Acrylic (Lucite™) wedges 218 (Olympus™, model ABWX 2001). Due to the frequency shifting effect of the acrylic material, the actual optimal frequency of the transducers 104 and 108 in this example when mounted on the wedges was around 3 MHz. The angle of incidence of the wedge 218 was set at around 63.7° (this angle was based on computer modeling to help ensure generation of a pre-selected waveguide propagation mode, a Rayleigh Lamb wave with phase velocity of v=2990 m/s). Acrylic shoes 220 were designed for mounting the transducer wedges 218 on a curved surface. The rear of the wedge 218 was lined up with the rear edge of the Acrylic shoe 220. Adding the Acrylic shoes 220 further reduced the optimal testing frequency range of the transducers to around 1 to 2 MHz in this embodiment, but other embodiments (using different mounting standards) may operate over different frequency ranges.

The continuous wave tests were conducted by sweeping the frequency linearly from 1 MHz to 4 MHZ (this corresponds to frequency-thickness product of 4.8 MHz-mm to 19.1 MHZ-mm). This was facilitated because the incident angle was selected to ensure generation of only one waveguide propagation mode within the small dispersion in the selected frequency range. The front transducer (to the left) was the transmitter 104 while the rear one was the receiver 108. The rear edge of receiver 108 was positioned 14.0 cm from the end of the pipe. Three separation distances between the transducer wedges were used for testing: 10 cm, 20 cm and 30 cm, respectively. For some of the tests, for which the signal was expected to be strong, the starting frequency was increased to 2 MHz. This improved the measurement quality but the features of the signal remained similar to the case where the starting frequency was 1.2 MHz.

In this experiment, the transducers were positioned face to face as shown in FIG. 55. The test consisted in varying the transducer spacing and measuring the continuous wave peak frequency. The relation between peak frequencies and transducers spacing could then be used to estimate the wave speed. The continuous UT wave was swept from 1 MHz to 3 MHz at the same voltage as in the plate testing (~ 30 V). Two sets of measurements were conducted for a sweep rate of 2 Hz per 100 ns and 1 Hz per 200 ns, respectively. The low pass filter cutoff frequency was set to 20 KHz. Time history of the continuous wave signal was acquired and saved by batches of samples representing 2 sweeps (200 ms). The sampling rate was approximately $5 \times 10^8$ samples per second.

Figures 56, 57:
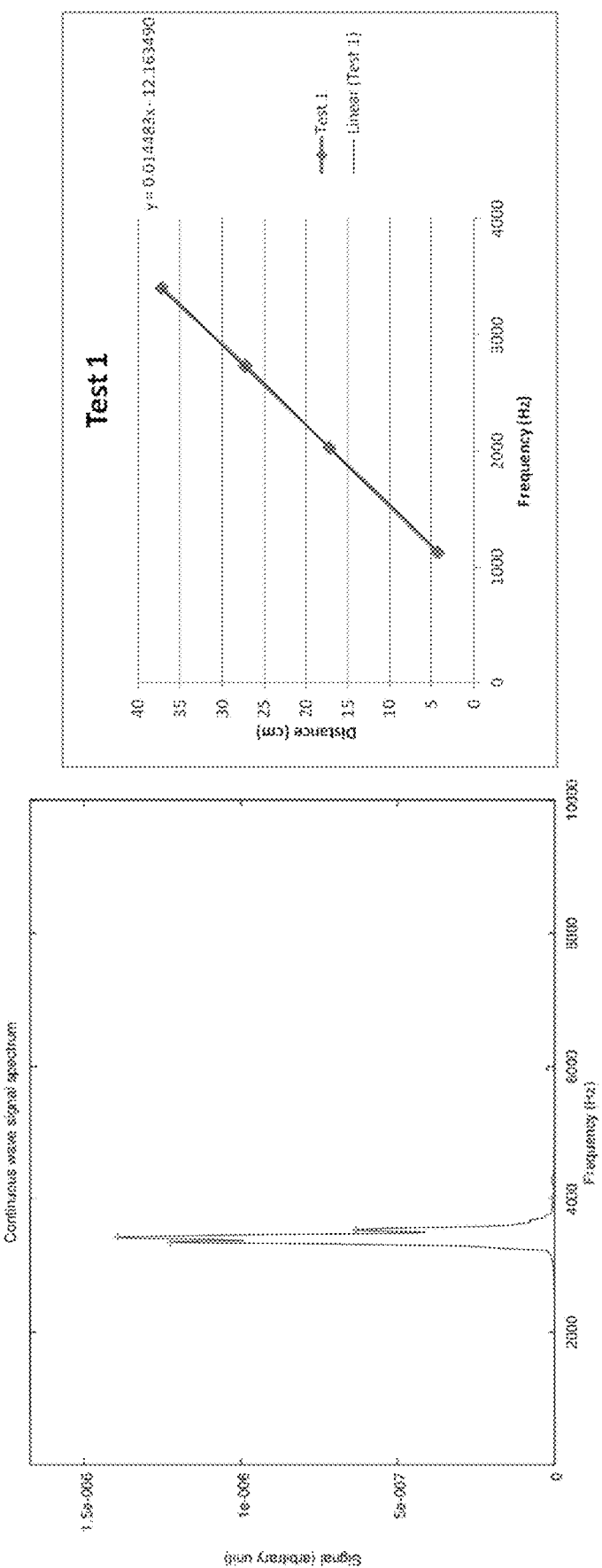
FIG. 56 is a plot showing continuous wave signal in the frequency domain for the SS pipe speed measurement test.
FIG. 57 is a plot showing distance versus peak frequencies for the wave speed measurement test on the SS pipe (Test 1)

A typical frequency domain signal is presented in FIG. 56. There are three peaks in FIG. 56, which can be attributed to multiple mode excitations due to the lower starting sweep frequency. The main peaks were used in the wave speed computation in this case. The measurement results are presented in Table 5, FIG. 57 and FIG. 58.

TABLE 5

Peak Frequencies for Test 1 (2 Hz per 100 Ns) and Test 2 (1 Hz per 200 Ns)

| Separation | Peak Frequencies (Hz) for Test 1 | | | | Peak Frequencies (Hz) for Test 2 | | | |
|---|---|---|---|---|---|---|---|---|
| Distance (cm) | Rep 0 | Rep 1 | Rep 2 | Average | Rep 0 | Rep 1 | Rep 2 | Average |
| 4.206 | 1129.6 | 1128.4 | 1128.4 | 1128.8 | 283.7 | 281.9 | | 282.8 |
| 17.206 | 2026.5 | 2027.1 | 2024.2 | 2025.9 | 506.6 | 506.0 | 504.3 | 505.6 |
| 27.206 | 2725.1 | 2729.7 | 2726.3 | 2727.0 | 673.4 | 679.1 | 677.4 | 676.6 |
| 37.206 | 3415.8 | 3404.3 | 3390.0 | 3403.4 | 843.0 | 844.7 | 855.6 | 847.8 |

Note that the peak frequencies for Test 1 are much larger than those of Test 2 because the sweep rate is faster for Test 1 ($\Delta f_1 = 2 \times 10$ Hz/s) as compared to Test 2 ($\Delta f_2 = 5 \times 10^6$ Hz/s). It can be seen that: $d/v = f_{R1}/\Delta f_1 = f_{R2}/\Delta f_2$ and hence, $f_{R1}/f_{R2} = \Delta f_1/\Delta f_2$.

Therefore, for the same separation distance (d), there should be a ratio of $\Delta f_1/\Delta f_2 = 4$ between the corresponding test peaks. The wave speed may be deduced as the product of the slope of the curves in FIG. 53 and the sweep rate ($v = c \cdot \Delta f$). The slopes are $c_1 = 0.014483$ cm/Hz and $c_2 = 0.058415$ cm/Hz, for Tests 1 and 2, respectively. The resulting wave speeds are $v_1 = 2.90$ km/s and $v_2 = 2.92$ km/s, which are within 3% of the nominal value (2.99 km/s). Note that the measured wave speed for this SS pipe is in agreement with the measurement of the SS plate (2.92 km/s).

Figure 58:
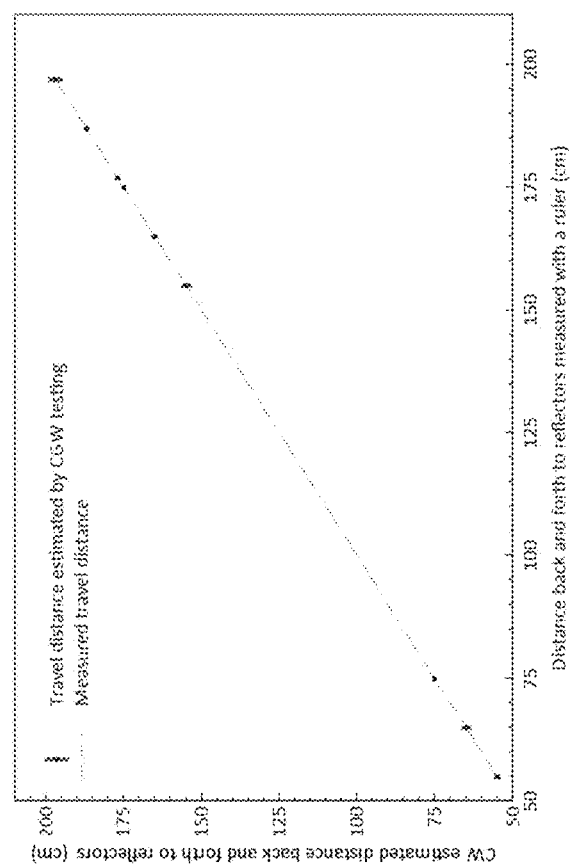
FIG. 58 is a plot showing distance versus peak frequencies for the wave speed measurement test on the SS pipe (Test 2)

The time delay at zero separation distance, resulting from the wave travel inside the wedge and shoe, can be deduced from FIG. 57 and FIG. 58. The time delay can be computed as $T_0 = f_0/\Delta f$, where $f_0$ is the extrapolated peak frequency at zero separation distance. From FIGS. 57 and 58 $f_0 = 893.9$ Hz and 210.9 Hz, which gives 44.7 us and 42.2 us for Tests 1 and 2, respectively. The average value of 43.4 us was used as an offset value for the rest of the SS pipe testing. Thus the Rayleigh-Lamb wave can be generated on a hollow cylindrical body in a similar way as in plates.

Another experiment was conducted focused on notch detection on piping. In this experiment, the transducers were orientated in the same direction and attached near one end of the pipe, as shown in FIG. 46. In this configuration, three reflections are expected: i) from the mid notch, ii) from the far notch and iii) from the far end. The continuous wave signal was swept from 1.2 MHz to 3.2 MHz at a sweep rate of 2 Hz per 100 ns. Data acquisition and sampling parameters are the same as in the speed measurement test.

The transducers were mounted such that the front transducer was transmitting while the rear one was acting as the receiver. Each transducer was mounted such that the rear of the wedge lined up with the rear edge of the UT shoe. In all tests, the rear edge of the rear transducer was positioned 14.0 cm from the near end of the pipe. The separation distance (translational) between transducer wedges was varied during the experiment. Three test cases were considered with transducer spacing equal to 10 cm, 20 cm and 30 cm, respectively.

Figure 47:
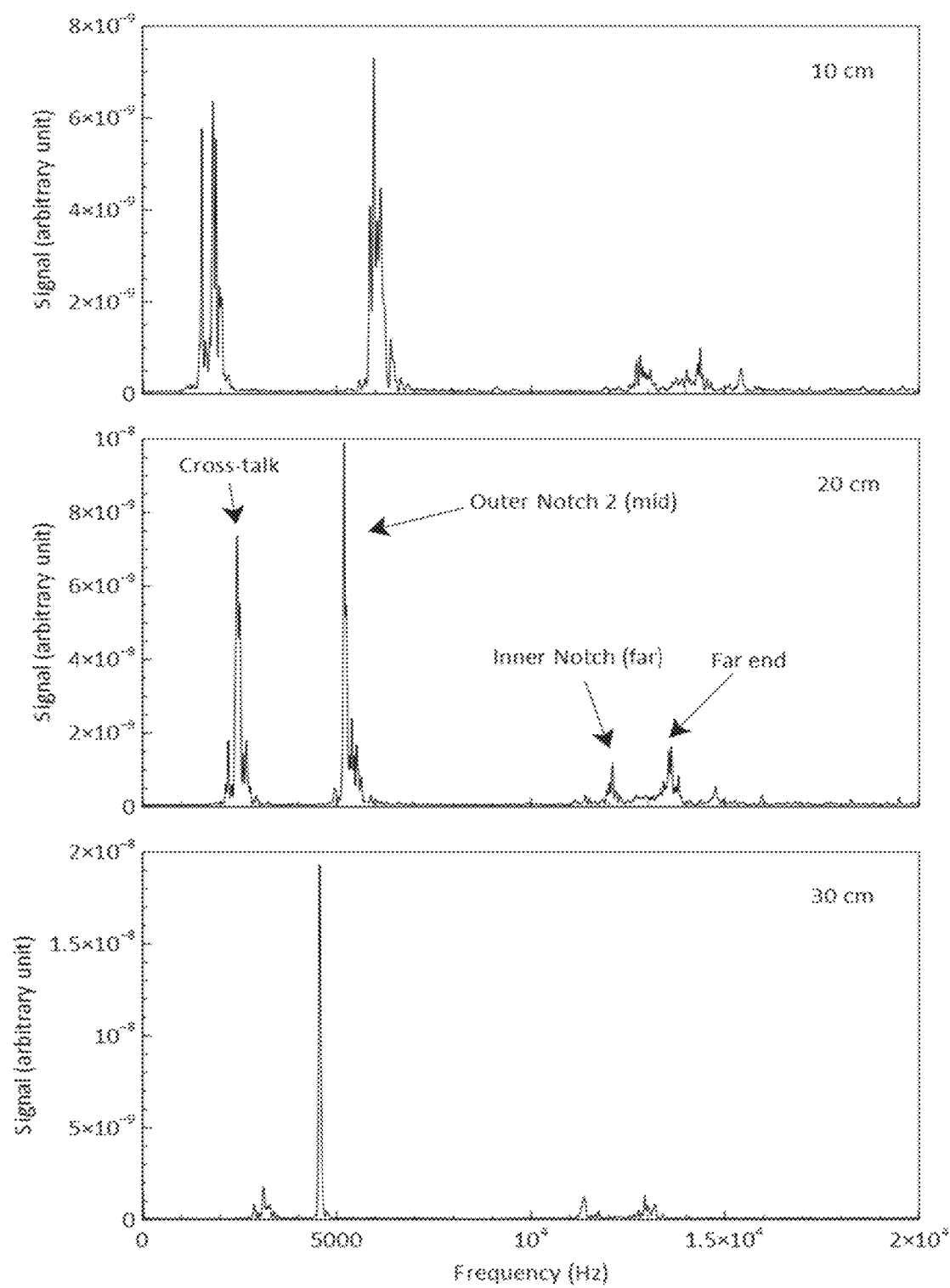
FIG. 47 is a plot showing a frequency domain signal for an experiment conducted using the apparatus of FIGS. 45 and 46.

The frequency domain signals for the three transducer-separation-distances are shown in FIG. 47. The peaks associated with the reflections from Outer Notch 204, Inner Notch 206, and pipe end, are indicated on FIG. 47. The peak frequency was noted to be generally proportional to the wave travel distance. The cross-talk peaks between the two transducers are also indicated in FIG. 47. The significant amount of cross-talk in the present experimental embodiment may be at least partially attributed to the fact that the Acrylic shoes lacked dents at their front faces that may have helped dissipate the reflected waves. Therefore, the incident waves may have bounced, possibly multiple times, in the Acrylic shoes and may be reflected to the receiver 108, which may contribute to the formation of multiple peaks associated with this cross-talk.

When the axial spacing between transducers 104 and 108 was increased, it was observed that:
a) the frequency of the cross-talk peak increased, which may be at least partially due to an increased distance between the two transducers;
b) The frequency of the three peaks (Outer Notch 204, Inner Notch 206, and pipe end) were slightly shifted to the left, which may be at least partially due to the decrease of the travel distance.
c) The frequency separation from the Outer Notch 204 peak to the Inner Notch 206 peak and to the pipe-end peak remained substantially constant since the distance did not change;
d) The magnitude of the cross-talk peak decreased while that of the Outer Notch 204 peak increased, which may be because the spacing between transducers increased and the front transducer got closer to the Outer Notch 204; and
e) The multiple reflections inside the Acrylic shoes were the most probable cause of multiple peaks in the cross-talk region, and in the reflections from Outer Notch #2, Inner Notch, and pipe end.

Results of the three transducer separation distance tests are summarized in Table 6. For each case, the peak frequencies associated with each of the three reflectors (Outer Notch 204, Inner Notch 206, and pipe end) are averaged over three repetitions. The wave travel distance, back and forth, to the reflectors was computed using Equation 14, with a wave velocity equal to 2920 m/s and sweep rate equal to $2\times10^7$ Hz/s. Note that the peak frequencies were corrected to remove the systemic time delay 43.4 us which generally corresponds to 869 Hz. As can be seen, in these cases the error in determining the distance was less than 3%, and in most cases, was 2% or less. The accuracy may be improved by accurately determining the wave speed in the structure, using precisely designed transducer mounts and accurately positioning the transducers on the structures.

TABLE 6

| Transducer Separation | | Peak Frequencies (Hz) | | | | Distance given by CGW Testing | Expected Distance | Distance Error |
|---|---|---|---|---|---|---|---|---|
| (cm) | Flaw | Rep 1 | Rep 2 | Rep 3 | Average | (cm) | (cm) | (%) |
| 10 | 1 | 5957.0 | 5957.6 | 5957.0 | 5957.2 | 74.3 | 74.9 | 0.8% |
|  | 2 | 12799.0 | 12799.5 | 12799.5 | 12799.3 | 174.2 | 174.9 | 0.4% |
|  | 3 | 14368.2 | 14371.0 | 14370.4 | 14369.9 | 197.1 | 196.9 | 0.1% |
| 20 | 1 | 5197.1 | 5198.2 | 5198.2 | 5197.8 | 63.2 | 64.9 | 2.6% |
|  | 2 | 12088.9 | 12090.6 | 12089.4 | 12089.6 | 163.8 | 164.9 | 0.6% |
|  | 3 | 13627.1 | 13626.5 | 13627.1 | 13626.9 | 186.3 | 186.9 | 0.3% |
| 30 | 1 | 4548.9 | 4550.6 | 4549.4 | 4549.6 | 53.7 | 54.9 | 2.0% |
|  | 2 | 11360.4 | 11367.9 | 11369.6 | 11366.0 | 153.3 | 154.9 | 1.0% |
|  | 3 | 12921.0 | 12919.9 | 12920.5 | 12920.5 | 176.0 | 176.9 | 0.5% |

For simplicity, the examples described herein have been illustrated with respect to an ultrasound embodiment, but an analogous system and method could be utilized with acoustic signals (acoustic, or sound, signals may have frequencies up to 20 kHz, while ultrasound waves may tend to be understood as having frequencies above 20 kHz).

Figure 59:
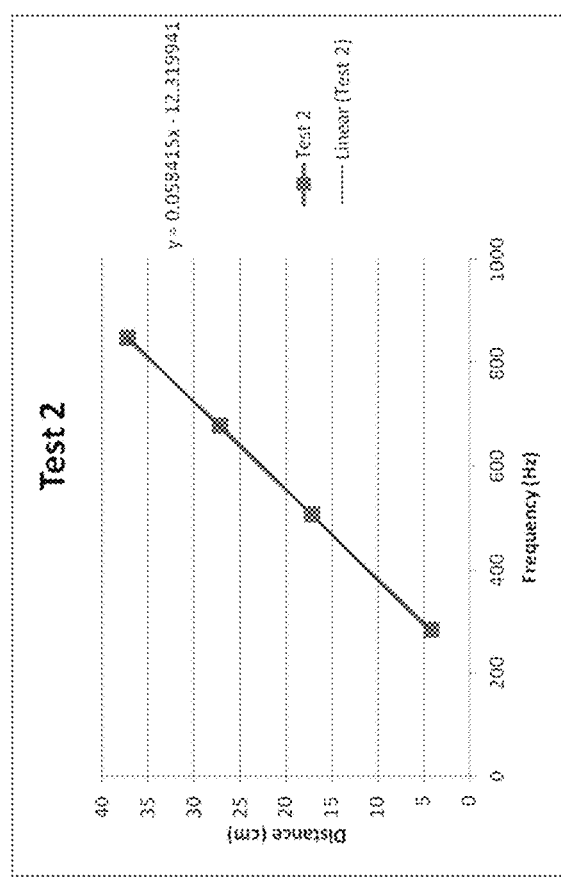
FIG. 59 is a plot showing distance back and forth to the reflectors (notches and far end) given by the continuous guided wave (CGW) testing, versus the travel distance measured with a ruler.

FIG. 59 plots the wave travel distance back and forth to the reflectors versus the travel distance, as measured by a ruler. The first three data points correspond to the mid-notch, the second three to the far notch and the last three to the far end. As shown in Table 6 and FIG. 59, the notches and pipe end were localized with good accuracy (less than 3% error).

A second experiment was also conducted where the two transducers were mounted near the inner notch. The results of this experiment are reported in Table 7 showing a comparable level of accuracy to the previous test.

TABLE 7

Notch Detection Data for Continuous Wave Pipe Testing
(Transducers Mounted Near the Inner Notch)

| Separation Distance | Re- | Peak Frequencies | | | | Measured Distance | Actual Distance | Localization Error |
|---|---|---|---|---|---|---|---|---|
| (cm) | flectors | Rep 1 | Rep 2 | Rep 3 | Average | (cm) | (cm) | (%) |
| 10 cm | 1 | 5954.2 | 5952.4 | — | 5953.3 | 74.2 | 74.9 | 0.8% |
|  | 2 | 12830.5 | — | 12835.1 | 12832.8 | 174.7 | 174.9 | 0.1% |
|  | 3 | 14514.3 | 14512.6 | 14512.6 | 14513.2 | 199.2 | 196.9 | 1.2% |

Tests conducted on the stainless steel tube described above showed that flaw detection on hollow cylindrical bodies was possible using continuous guided waves. In these experiments the length of the pipe was about 1.2 m. An addition test was conducted using a longer Inconel steam-generator tube 200A.

In this example, the tube was 4.63 m long; its outer diameter was ¾" (19.05 mm) and its thickness ¹⁄₁₆ " (1.59 mm). The tube material was Inconel 690 ($v_L$=5.82 km/s, $v_T$=3.02 km/s and Poisson ratio=0.289). The computed Rayleigh wave speed was 2.81 km/s. This gives approximately 72.5° of incidence angle for acrylic wedges and shoes.

Figure 54:
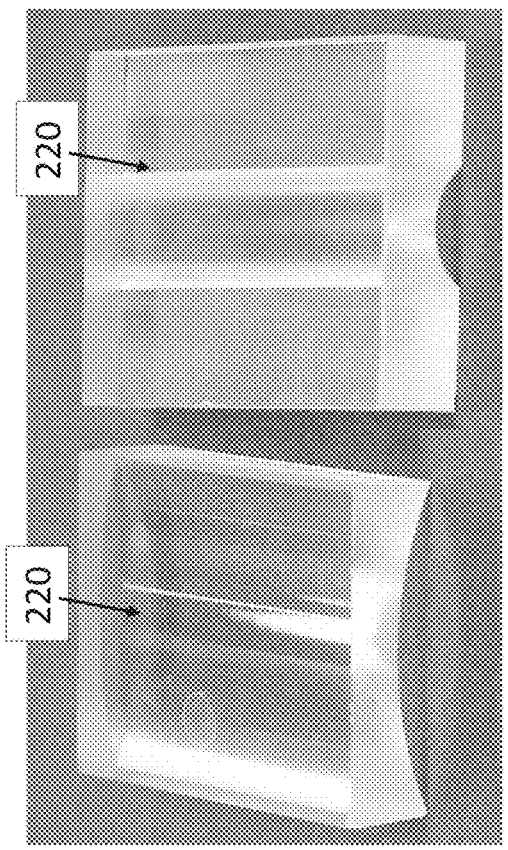
FIG. 54 is a photo showing acrylic shoes used in experiments described herein.

The purpose of this experiment is to see whether or not a reflection from the end of the tube could be detected. A tube end reflection is generally similar to notch or flaw reflection, and so no notch was made on this tube. Although signal reflection is similar for both surface flaw and tube end, the UT signal is likely to be weaker in the case of a flaw because the flaw size is only a small percentage of the structure wall thickness (FIG. 54). A smaller portion of the UT energy is reflected by a surface flaw as compared to the tube end. Nonetheless, this provided information on the range of guided wave testing in laboratory conditions.

In this experiment the continuous wave signal was swept from 1 MHz to 4 MHZ (frequency thickness product of 1.6 MHz-mm to 6.4 MHZ-mm). The frequency thickness product was clearly outside the non-dispersive region of the Rayleigh wave (≥ 6.5 MHZ-mm). Thus, multiple-mode excitation is to be expected. The transducers were mounted on the Inconel tube by attaching them to the acrylic wedges and shoes as shown in FIG. 61.

Using this set-up, speed measurement tests were first conducted, during which the two transducers were mounted facing one another. A typical frequency domain signal for these tests is presented in FIG. 62. Plots of peak frequency versus transducer separation distance are presented in FIGS. 63 and 64 for two repetitions (Tests 1 and 2). The sweep rate was 2 Hz per 100 ns in both tests. The wave speed was estimated to be 3.08 km/s and 3.17 km/s for Tests 1 and 2, respectively. The systemic time delay (at zero separation distance) was estimated from FIGS. 63 and 64 to be 43.2 us and 44.7 us for Tests 1 and 2, respectively.

It was discovered that the systemic time delay is approximately the same as for the stainless tube test, which may be related to the fact that the wedges are identical and the acrylic shoes used had approximately the same dimensions. The wave speed is slightly higher than the expected Rayleigh wave speed (2.81 km/s). This may be because the frequency range was outside the Rayleigh wave frequency range. The group velocity of the excited wave is expected to be different from that of the Rayleigh wave.

An end reflection test was also conduced. For the end reflection test, the rear edge of the rear transducer was positioned at 30.0 cm from the near end of the tube. The front transducer was transmitting while the rear one was acting as the receiver. Tests were conducted for transducer spacings (distance between rear edges of the wedges) of 20 cm, 30 cm and 40 cm. The continuous wave signal was swept from 1 MHz to 4 MHz at a sweep rate of 1 Hz per 500 ns. Note that the sweep rate was relatively small as compared to all previous tests because the distance of interest here is large; so reducing the sweep rate also helps reduce the peak frequency to a desired, comparable level. The low pass filter cutoff frequency was set to 20 KHz for this experiment. The resolution of the picoscope was 10 ms/div. Time history data were saved by batches of 100 ms at a sampling rate of approximately $10^9$ samples per second.

Representative frequency domain signals from the experiments conducted are presented in FIG. 65. Reflection from the end of the tube can be clearly seen. However, the peak is not as narrow as for the stainless steel pipe testing. There are three small peaks which can be attributed to multiple modes propagating, each, at slightly different group speed than that of the fundamental mode. The wave travel distance was estimated for each of the peaks, assuming that they travelled at the same speed (3.12 km/s) as measured in the previous experiment. The results are reported in Table 8. The results of the middle peaks are the closest to the distance travelled back and forth to the tube end. Clearly, the speed of the other two peaks is different.

In these experiments, the angle beam method was used to generate guided Lamb waves in steel plates. The experimental setup in these examples included stainless steel (SS 304) plates, two variable angle wedges, two standard UT transducers, and an electronic system for signal generation and data acquisition. FIG. 66 shows a photograph of the two transducers 304 and 308 and variable angle wedges 310 used these experiments. The variable angle wedges 310 were made of acrylic (Lucite) whose longitudinal wave speed is $v_L$=2.68 km/s and transverse wave speed is vr=1.84 km/s. The wedges 311 in this case were manufactured by Olympus and their model number was ABWX-2001. Other suitable wedges or other types of mounting and supporting structures could be used in other experiments or applications of the teaching herein.

The UT transducers 304 and 308 used in this experiment were also manufactured by Olympus and their frequency range was centered at 5 MHz. Due to the frequency-shifting effect of the acrylic material, the actual optimal frequency of the transducers when mounted on the wedges was around 3 MHz. The model number for the UT transducers was V405-SB.

Referring also to FIG. 67 another example of a continuous wave frequency-modulated ultrasound inspection system 3100 is generally analogous to the continuous wave frequency-modulated ultrasound inspection system 100, with like features annotated using like reference characters indexed by 3000. This embodiment is generally similar to the others described herein but has been configured to include relatively more powerful amplifiers which help facilitate use of the system 3100 for waveguide measurements. In this example, the signal generator 3102 is combined in the same unit as the controller 3131, along with the low pass filter, DAQ, processor and other components described herein. In the specific experiments described the experimental set-up included:

A computer running 32 bit Windows XP operating system.
A signal generator and data acquisition device (Picoscope 5000 series).

TABLE 8

Peak Frequency Data for Inconel Tube end Reflection Testing

| Separation Distance (cm) | Peaks | Peak frequencies (Hz) | | | | Distance Given by CW Testing (cm) | Distance Measured Using a Ruler (cm) | Localization Error (%) |
| --- | --- | --- | --- | --- | --- | --- | --- | --- |
| | | Rep 1 | Rep 2 | Rep 3 | Average | | | |
| 20 cm | 2 | 5019.6 | 5018.5 | 5016.4 | 5018.1 | 758.9 | 836.9 | |
| | 3 | 5529.4 | 5533.7 | 5610.3 | 5557.8 | 840.1 | | 0.4% |
| | 4 | 5834.9 | 5827.4 | 5829.5 | 5830.6 | 881.2 | | |
| 30 cm | 2 | 5082.4 | — | 4969.5 | 5025.9 | 760.1 | 826.9 | |
| | 3 | 5476.2 | 5470.9 | 5465.5 | 5470.9 | 827.1 | | 0.02% |
| | 4 | 5818.9 | 5823.2 | 5814.6 | 5818.9 | 879.4 | | |
| 40 cm | 2 | 4920.6 | 4946.1 | 4903.5 | 4923.4 | 744.7 | 816.9 | |
| | 3 | 5350.6 | 5519.8 | | 5435.2 | 821.7 | | 0.6% |

This test shows that the continuous guided wave method can be used for testing a tube up to a range of 4.6 m. The wave travel distance was more than 8 m.

In addition to the testing on the pipes/tubes described herein, further experiments were conducted to test the techniques for guided Lamb wave generation in a plate, the application of the continuous wave method to guided waves in plates and to use guided waves for flaw localization on the surface of a plate.

A power amplifier 325LA.
A signal amplifier for the transmitted signal (ZHL-6A+).
A signal amplifier for the received signal (ZFL-500LN)
A signal splitter (ZFDC-10$^{-6}$+).
A signal mixer (ZAD-6+).
Three SS 304 plates of thickness 0.105"±0.005" (2.67 mm±0.13 mm), 0.120"±0.005" (3.05 mm±0.13 mm), and 0.180"±0.005" (4.57 mm±0.13 mm) were available. Unless otherwise specified, all tests discussed in the following were conducted with the 2.67 mm thick plate. During the testing, only one face of each plate was polished. This created asymmetry in surface finish, which may help simulate real life situations where one face would generally be more corroded or scratched than the other.

Tests were generally performed using either the continuous wave or the pulse wave method. The continuous wave method was implemented using the frequency-modulated continuous wave reflectometry technique. FIG. 67 shows the diagram of the signal routing for the continuous wave testing in a wave speed measurement configuration. The signal generated by the signal generator 3102 was split by splitter 3140 and sent to both the transmitting transducer 3104 and the mixer 3128. Signals going to or coming from the transducers were amplified. The mixer 3128 was used to multiply the transmitted and received signals. The result is filtered and FFT-processed by the picoscope (in controller 3131) to give the peak frequency from which the time delay between the two signals is computed.

Comparative tests were also conducted using pulse-echo testing techniques in which the transmitted and received signals were acquired directly by the computer and superimposed in the graph of the signal generator software.

The target was the Rayleigh-Lamb wave over a range of frequencies where the phase velocity was substantially constant. As explained in previously, this may occur in steel plates for $f_d \geq 6.7$ MHz-mm³. For a plate of thickness 2.67 mm (0.105"), this corresponds to a frequency of 2.42 MHz. In this application of the continuous wave method, the frequency was generally swept from around 2.5 MHz to around 6.5 MHz, within this non-dispersive region. In the pulse-echo method, tone bursts of 3 MHz and 20 cycles per burst, spaced by 300 µs, were generated and sent to the transducers.

In both CW and PE methods tested, the amplitude of the generated signal was approximately 800 mV, which was reduced to slightly less than 200 mV by the splitter before being sent to the amplifier. Knowing that the gain of the amplifier is around ×170 for a frequency range of 4-10 MHz, the output signal sent to the UT transducer was approximately 30 V.

The angle of the wedge was computed to generate a wave of speed equal to the Rayleigh Lamb wave $v_R$=2.99 km/s. Knowing the wave speed in the wedge material, the angle of the wedge could be computed using Snell's law as follows:

$$\theta_{wedge} = \sin^{-1}\left(\frac{v_{Lucite}}{v_R}\right)$$

where, $\theta_{wedge}$ is the angle of incidence of the transmitted wave and $v_{Lucite}$ is the longitudinal wave speed of the wedge material. The computed value of the incidence angle was $\theta_{wedge}$=63.7".

Referring to FIG. 68, in this experiment, the two transducers 3104 and 3108 were positioned face to face (through transmission) at known distances on the surface of a plate 3150 and the travel time estimated using either the direct time delay measurement (pulsed wave method) or time delay reflectrometry technique (continuous wave method). In this setup, the signal travels once from the transmitter to the receiver (see FIG. 67).

To do this, the receiving transducer 3108 was positioned at four locations and the time delay (travel time) measured directly using pulse superposition, or indirectly through the peak frequency of the continuous signal spectrum. The wave velocity was computed afterwards from those data. The speed is assumed to be only dependent on the material properties. The surface finish is expected to have an attenuation effect, reducing the wave amplitude rather than modifying its speed. For example, if the wave speed of the "coarse face" were different from that of the polished face, the reflection from the notches or plate-end would be duplicated into two distinct pulses (in the pulse echo tests) or two distinct frequency peaks (in the CW tests). This was not observed in the pulse echo results.

For the CW testing on the other hand, there were instances of multiple frequency peaks. The double-peaks may be due to the excitation of two distinct modes: S0 and A0 at the beginning of the sweep. It was realized after the tests that in fact, the non-dispersive region starts at a slightly higher frequency than 2.5 MHz. The discussions with regards to the results of the tests conducted in the range 2.5-6.5 MHz remain valid but this finding sheds light on some of the results such as the double-peaks and the slightly lower than expected Rayleigh wave speed.

FIG. 69 shows the signals for various separation distances between the transducers 3104 and 3018 (distances are measured from the front of the wedge). The spectra of the continuous wave signals are shown in the left column where the peak frequencies can be clearly identified. Note that the peak frequency (hence the time delay) is not zero for 0 separation distance. This may be due to the systemic time delay inherent to the transducers, resulting from their manufacturing process, and to the non-zero travel time of the wave throughout each of the two acrylic wedges. Nonetheless, there is a generally a linear relation between peak frequencies and travel times or equivalently travel distances. This is shown in FIG. 70 where the travel distance is plotted against the peak frequencies. The slope of this curve was computed as c=0.1458 mm/Hz using linear curve fitting. The travel distance can be expressed as $d=(v/\Delta f)\cdot f_R = c\cdot f_R$, from which the wave velocity can be deduced as $v=c\cdot\Delta f$. In the current test, the time increment was taken as tinc=100 ns and the frequency increment finc=2 Hz per step; hence the sweep rate is $\Delta f$=finc/tinc=2×10⁷ Hz/s. The wave group velocity is, therefore, v=2.92 km/s, which is within 2.35% of the nominal value ($v_R$=2.99 km/s). Wave travel time computed from the peak frequencies and is also reported in Table 9.

The results of the pulse method are also shown in the right column of FIG. 69. Three tone bursts at a frequency of 3 MHz with 20 cycles per burst were generated and sent to the transmitter. The received signal (lower-green) was acquired and superimposed on the transmitted signal (top-red). Note that both signals were amplified. Therefore the values indicated in FIG. 69 do not correspond to the actual voltage that excited the transmitter or was generated by the receiver. The time delay between the two signals was estimated by taking the first drop of the signal below 50% of the minimum for each signal and computing the delay between the two instants.

FIG. 71 plots the travel distance directly against the travel time for the pulse method. A linear curve fitting technique was used to estimate the slope of the curve (2.88 km/s) which corresponds to the wave group velocity. In comparison with the nominal value (2.99 km/s), the wave group velocity estimate is good but less than for the continuous wave method (2.92 km/s). Both methods work, although it can be seen in FIG. 69 that the SNR deteriorates with distance when using the pulse echo method. For instance, the strength of the received signal decreased from around 20 mV to around 6 mV when the separation distance was increased from 0 to 0.457 m. This decrease in signal strength did not affect significantly the SNR in the continuous wave method where the signal was still 15-20 dB above the noise level. As shown in Table 9, the accuracy of the pulse wave method decreases with distance due to reduced SNR.

TABLE 9

Peak Frequencies and Travel Time Given By the CW and Pulse Wave Methods

| Separation | Continuous Wave Method | | |
| --- | --- | --- | --- |
| Distance between Transmitter and Receiver | Peak frequency (Hz) | Travel time computed using Eq. (7) (µs) | Pulse Wave Method Travel time (µs) |
| 0.0 | 810.8 | 40.5 | 40.7 |
| 152.4 | 1866.0 | 93.3 | 92.9 |
| 304.8 | 2911.3 | 145.6 | 145.5 |
| 457.2 | 3947.1 | 197.4 | 199.0 |

Experiments were also conducted that were focused on the use of guided waves for detection of defects on the surface of a plate 3150. In this experiment, two parallel notches 3152 of 0.5 mm wide×0.5 mm deep were made on the 2.67 mm thick SS304 plate 3150. In this experiment, the transducers 3104 and 3108 were orientated in the same direction as illustrated in FIGS. 72 and 73, in contrast with the previous experiment where transmitter 3104 and receiver 3108 were facing one another. The waves generated by the transmitter 3104 are expected to be reflected by both a notch 3152 and end of the plate 3150 and travel back to the receiver 3108 where the reflections may be detected. The notches were made on the non-polished face of the plate 3150.

Considering the front end of the back wedge as the origin of position for measuring length, the front end of the front wedge was located at 9.8 cm, while a notch 3152 was at 25 cm and the end of the plate was at 40.3 cm. The total distance travelled by the wave back and forth between transmitter wedge and receiver wedge would be 2×25 cm−9.8 cm=40.2 cm for the notch, and 2×40.3 cm−9.8 cm=70.8 cm for the end of the plate 3150.

In the continuous wave method, the frequency was swept from 2.5 MHz to 6.5 MHz with a time increment tinc=100 ns and frequency increment finc=2 Hz per step. It was realized during one experiment that the FFT feature of the picoscope was not working properly. The filtered signal could be seen as periodic in the time domain while there was no peak in the frequency domain so it was decided to save the time history of the filtered signal and perform the FFT afterwards using a custom script developed in Matlab. The total time necessary for the signal to achieve a single sweep of 4 MHz wide (2.5 MHz to 6.5 MHZ) is $1=4$ MHz/$\Delta f$=(4× $10^6$ Hz)/(2×$10^7$ Hz/s)=0.2 s, where $\Delta f$=finc/tinc=2×$10^7$ Hz/s. The time history of the filtered signal was saved by batches of 200 ms long (the duration of a single sweep).

A Matlab script was written to perform the Fourier analysis. Noise reduction was achieved using the Welch algorithm with 50% overlap. Spectral leakage was also reduced using a Hamming window, which is known to preserve frequency resolution at the expense of amplitude accuracy. This was deemed a reasonable choice since the goal was to locate the peaks rather than to compute accurately their amplitudes. Pulse-echo tests were also performed for comparison.

Results of this experiment are presented in FIG. 74 and Tables 10 to 12 for a configuration where the transducers 3104 and 3108 were placed on the same face as the notch 3152, with the front transducer acting as the transmitter. Peaks associated with reflections from the notch and end of the plate are shown in FIG. 74. It can also be seen in FIG. 74 that the noise is considerably reduced by the Welch-overlapping method as compared to the processing of the picoscope.

Table 10 reports the values of the peak frequencies for several repetitions. The results were substantially consistent across the repetitions. Note that the results presented in Table 10 include the systemic frequency associated with the wave travel time inside the transducers and wedges, while those presented in Table 11 were corrected to remove this offset frequency. The travel distance of the wave as it goes from the transmitter wedge to the reflector and back to the receiver wedge (back-and-forth) is computed from the peak frequencies of Table 11 and reported in Table 12. A comparison between travel distances predicted by the CW testing and that measured with a ruler is presented in Table 12, showing an error of 0.5% and 1.8% for the notch and end of the plate, respectively. This experiment has demonstrated the capability of the CW method for defect localization using guided waves.

The transmitted and received pulse-echo signals are shown in FIG. 75. The expected time delay for the notch and end of plate, computed using a wave speed of 2.92 km/s and time delay offset of 40.6 µs, are 178 us and 283 µs, respectively. In this arrangement the noise is such that the reflections could not be readily identified. Note that the only noise reduction technique employed in the pulse-echo method is a low-pass filtering of 4 MHz cuttoff, the frequency of the pulse being 3 MHz. Note also that the voltage of the transmitted pulse-echo signal after amplification is about 30 V as mentioned in herein. If higher voltage pulses (e.g. 400 V) and improved noise reduction techniques were used, the SNR could possibly be improved and the signal could possibly have been seen.

TABLE 10

Uncorrected Peak Frequencies Given by the CW Method

| | Repetition 1 | Repetition 2 | Repetition 3 | Average |
| --- | --- | --- | --- | --- |
| First peak (kHz) | 3.5119 | 3.5155 | 3.5149 | 3.5141 |
| Second peak (kHz) | 5.4586 | 5.4646 | 5.4687 | 5.464 |

TABLE 11

Corrected Peak Frequencies Given by the CW Method

| | Repetition 1 | Repetition 2 | Repetition 3 | Average |
| --- | --- | --- | --- | --- |
| First peak (kHz) | 2.7011 | 2.7047 | 2.7041 | 2.7033 |
| Second peak (kHz) | 4.6478 | 4.6538 | 4.6579 | 4.6532 |

TABLE 12

Reflector Locations Predicted by the CW Method

|  | Repetition 1 | Repetition 2 | Repetition 3 | Average | Actual Location | Error |
|---|---|---|---|---|---|---|
| Distance back and forth to the notch | 40.3 | 40.4 | 40.4 | 40.4 | 40.2 | +0.5% |
| Distance back and forth to the end of the plate | 69.4 | 69.5 | 69.5 | 69.5 | 70.8 | −1.8% |

Additional experiments were conducted where the rear transducer was plugged to the signal generator 3102 so that it operates as the transmitter. The results of this experiment are presented in FIG. 76 and Tables 13 and 14. The reflectors were localized as in the previous experiment with almost the same accuracy. However, the signal strength is reduced as compared to FIG. 74. The vertical scale in FIG. 76 was made identical to that of FIG. 74 for comparison purposes.

Based on this the inventors discovered that the transmitted signal was attenuated by the couplant as it passed the receiver to reach the reflectors. This may have contributed to a weak reflected signal. However, it is also noted that in the opposite configuration (transmitter on the front); the reflected signal may be attenuated by the couplant under the transmitter before it reaches the receiver. So the signal may be attenuated by the couplant in both cases but for some unknown reason the best configuration is to have the transmitter on the front. To reduce the attenuation induced by the couplant, a dual transducer, where both transmitter and receiver would be mounted on the same wedge, could be utilized.

TABLE 13

Uncorrected Peak Frequencies Given by the CW Method

|  | Repetition 1 | Repetition 2 | Repetition 3 | Average |
|---|---|---|---|---|
| First peak (kHz) | 3.5048 | 3.4958 | 3.5006 | 3.5004 |
| Second peak (kHz) | 5.4443 | 5.4413 | 5.4479 | 5.4445 |

TABLE 14

Reflector Locations Predicted by the CW Method

|  | Repetition 1 | Repetition 2 | Repetition 3 | Average | Actual Location | Error |
|---|---|---|---|---|---|---|
| Distance back and forth to the notch | 40.2 | 40.1 | 40.1 | 40.1 | 40.2 | 0.2% |
| Distance back and forth to the end of the | 69.2 | 69.1 | 69.2 | 69.2 | 70.8 | 2.3% |

Another experiment was conducted with transducers on one face of a plate to remotely detect a defect on the opposite face. This was investigated in this test, where the transducers were set up as shown in FIG. 77, on the opposite face of the plate. In this example, the transducers 3104 and 3108 were positioned on the polished face of the plate 3150 while the notch 3152 was on the opposing "coarse" face.

FIG. 78 shows the continuous wave spectrum for a configuration where the front transducer is acting as the transmitter. Tables 15 and 16 summarize the uncorrected and corrected peak frequencies, respectively. In addition to the reflections from the notch and end of the plate that can be seen in FIG. 78, there are also two peaks near the lower end of the frequency spectrum. The second peak was identified as induced by the wave that travelled backward from the transmitter (front transducer) to the receiver (back transducer). This is proved by the results of Table 17 showing that this peak is originated 9.9 cm from the receiver, which correspond to the location of the front transducer (9.8 cm). The phenomenon of backward travelling wave was not seen on the unpolished face (previous experiment) because of the high attenuation associated with the surface roughness.

TABLE 15

Uncorrected Peak Frequencies Given by the CW Method (Transmitter on the Front)

|  | Repetition 1 | Repetition 2 | Average |
|---|---|---|---|
| First peak (kHz) | 0.9131 | 0.9161 | 0.9146 |
| Second peak (kHz) | 1.4734 | 1.477 | 1.4752 |
| Third peak (kHz) | 3.5977 | 3.5864 | 3.5921 |
| Fourth peak (kHz) | 5.6237 | 5.5206 | 5.5721 |

TABLE 16

Corrected Peak Frequencies Given by the CW Method (Transmitter on the Front)

|  | Repetition 1 | Repetition 2 | Average |
|---|---|---|---|
| First peak (kHz) | 0.1023 | 0.1053 | 0.1038 |
| Second peak (kHz) | 0.6626 | 0.6662 | 0.6644 |
| Third peak (kHz) | 2.7869 | 2.7756 | 2.7813 |
| Fourth peak (kHz) | 4.8129 | 4.7098 | 4.7613 |

TABLE 17

Reflector Locations Predicted by the CW Method
(Transmitter on the Front)

|  | Repetition 1 | Repetition 2 | Average | Actual Location | Error |
| --- | --- | --- | --- | --- | --- |
| Unidentified reflection | — | — | — | — | — |
| Separation distance between the two | 9.9 | 9.9 | 9.9 | 9.8 | 1.0% |
| Distance forth and back to the notch(cm) | 41.6 | 41.4 | 41.5 | 40.2 | 3.2% |
| Distance forth and back to the end of the plate(cm) | 71.8 | 70.3 | 71.1 | 70.8 | 0.4% |

The pulse-echo signals for this test are plotted in FIG. 80, where the lowest trace is the received signal while the other is the transmitted signal. Although the received signal was noisy, the reflections could be identified. Note that when the transducers were mounted on the opposite face (coarse surface), the reflection could not be seen due to high noise.

What has been described above has been intended to be illustrative of the invention and non-limiting and it will be understood by persons skilled in the art that other variants and modifications may be made without departing from the scope of the invention as defined in the claims appended hereto.

We claim:

1. A method of determining a distance to a discontinuity within an object using a guided wave, the method comprising:
   a) generating a continuous, frequency modulated input signal having a predetermined frequency range and a frequency ramping speed using a signal generator and splitting the input signal into at least a test signal and a reference signal;
   b) generating an input guided wave based on the test signal using a guided wave transducer, wherein the frequency range is limited to frequencies for which a phase velocity of the input guided wave is substantially constant;
   c) continuously introducing the input guided wave into the object using the guided wave transducer, and simultaneously receiving a reflected sound wave reflected by a discontinuity within the object and generating a corresponding return signal using a receiver;
   d) determining a frequency difference value based on a comparison of the reference signal and the return signal using a controller; and
   e) automatically determining a distance from the transmitter to the discontinuity within the object based on at least the frequency difference value and the frequency ramping speed using the controller.

2. The method of claim 1, wherein the guided wave transducer comprises an angle beam transducer and the input guided wave is generated using an angle beam method.

3. The method of claim 2, wherein the angle beam transducer generates the input guided wave at an angle of incidence relative to the object and wherein the angle of incidence remains constant during steps b) and c).

4. The method of claim 1, wherein the input guided wave comprises a Rayleigh-Lamb wave.

5. The method of claim 1, wherein step d) comprises:
   f) multiplying the return signal with the reference signal using a signal multiplier to provide a multiplied output signal,
   g) filtering the multiplied output signal using a low-pass filter to filter out at least some of the frequencies in the multiplied output signal and provide a filtered output signal; and
   h) digitizing the filtered output signal using a data acquisition apparatus to provide a digitized output signal; and
   i) determining the frequency difference value by applying a fast Fourier transform to the digitized output signal to provide a FFT spectrum and identifying the frequency difference value as a peak on the FFT spectrum.

6. The method of claim 5, wherein step e) further comprises determining the distance based on the frequency difference, the frequency ramping speed and a speed of sound within the object.

7. The method of claim 6, wherein the distance is determined using the function $$d_i = \frac{v \cdot f_R}{2 \cdot \Delta f},$$

where $d_i$ is the distance (mm), $v$ is speed of sound within the object (mm/s), $f_R$ is the frequency difference (MHz) and $\Delta f$ is the frequency ramping speed (MHz/s).

8. The method of claim 1, wherein the frequency ramping speed is between about 0.01 and 1000 MHz/sec.

9. The method of claim 8, wherein the frequency ramping speed is about 20 MHz/sec.

* * * * *